(12) United States Patent
Vainstein et al.

(10) Patent No.: US 10,883,111 B2
(45) Date of Patent: Jan. 5, 2021

(54) NUCLEIC ACID CONSTRUCTS FOR GENOME EDITING

(71) Applicant: Danziger Innovations Ltd., Moshav Mishmar HaShiva (IL)

(72) Inventors: Alexander Vainstein, Rechovot (IL); Ira Marton, Rechovot (IL); Arik Honig, Rehovot (IL); Elena Marhevka, Rechovot (IL)

(73) Assignee: Danziger Innovations Ltd., Moshav Mishmar HaShiva (IL)

(*) Notice: Subject to any disclaimer, the term of this patent is extended or adjusted under 35 U.S.C. 154(b) by 185 days.

(21) Appl. No.: 15/531,436

(22) PCT Filed: Nov. 26, 2015

(86) PCT No.: PCT/IL2015/051150
§ 371 (c)(1),
(2) Date: May 28, 2017

(87) PCT Pub. No.: WO2016/084084
PCT Pub. Date: Jun. 2, 2016

(65) Prior Publication Data
US 2017/0260536 A1 Sep. 14, 2017

Related U.S. Application Data

(60) Provisional application No. 62/085,292, filed on Nov. 27, 2014.

(51) Int. Cl.
*C12N 15/82* (2006.01)

(52) U.S. Cl.
CPC ..... *C12N 15/8213* (2013.01); *C12N 15/8203* (2013.01); *C12N 15/8216* (2013.01); *C12N 15/8271* (2013.01); *C12N 15/8274* (2013.01); *C12N 15/8279* (2013.01); *C12N 2310/20* (2017.05)

(58) Field of Classification Search
CPC ............ C12N 2310/20; C12N 15/8273; C12N 15/8279
See application file for complete search history.

(56) References Cited

U.S. PATENT DOCUMENTS

| | | | |
|---|---|---|---|
| 5,316,931 A | 5/1994 | Donson et al. | |
| 5,530,191 A | 6/1996 | Maliga | |
| 5,811,653 A | 9/1998 | Turpen | |
| 6,300,133 B1 | 10/2001 | Lindbo et al. | |
| 6,610,545 B2 | 8/2003 | Dujon et al. | |
| 6,911,575 B1 | 6/2005 | Baszczynski et al. | |
| 7,229,829 B2 | 6/2007 | Dinesh Kumar et al. | |
| 7,309,605 B1 | 12/2007 | Dujon et al. | |
| 8,791,324 B2 * | 7/2014 | Vainstein ............ | C12N 15/8289 800/278 |
| 2003/0182684 A1 | 9/2003 | Dinesh Kumar et al. | |
| 2005/0009012 A1 | 1/2005 | Holzberg et al. | |
| 2005/0026157 A1 | 2/2005 | Baltimore et al. | |
| 2006/0292682 A1 | 12/2006 | Hawkins et al. | |
| 2007/0134796 A1 | 6/2007 | Holmes et al. | |
| 2008/0182332 A1 | 7/2008 | Cai et al. | |
| 2012/0210461 A1 | 8/2012 | Vainstein et al. | |
| 2014/0273235 A1 * | 9/2014 | Voytas ...................... | C12N 9/16 435/469 |
| 2014/0331360 A1 | 11/2014 | Vainstein et al. | |
| 2017/0022499 A1 * | 1/2017 | Lu ........................... | C12N 15/63 |

FOREIGN PATENT DOCUMENTS

| | | |
|---|---|---|
| CN | 1118609 | 3/1996 |
| IL | 208819 | 7/2013 |
| WO | WO 2007/137788 | 12/2007 |
| WO | WO 2007/139982 | 12/2007 |
| WO | WO 2008/148559 | 12/2008 |
| WO | WO 2009/130695 | 10/2009 |
| WO | WO 2011/048600 | 4/2011 |
| WO | WO-2013192278 A1 * | 12/2013 ......... C12N 15/8203 |
| WO | WO 2015/189693 | 12/2015 |
| WO | WO 2016/084084 | 6/2016 |

OTHER PUBLICATIONS

Zhang, Yong, et al. "Transcription activator-like effector nucleases enable efficient plant genome engineering." Plant physiology 161.1 (2013): 20-27. (Year: 2013).*
Belhaj, Khaoula, et al. "Plant genome editing made easy: targeted mutagenesis in model and crop plants using the CRISPR/Cas system." Plant methods 9.1 (2013): 39 (Year: 2013).*
Kabadi, Ami M., et al. "Multiplex CRISPR/Cas9-based genome engineering from a single lentiviral vector." Nucleic acids research 42.19 (2014): e147-e147 (Year: 2014).*
Kay, Robert, et al. "Duplication of CaMV 35S promoter sequences creates a strong enhancer for plant genes." Science 236.4806 (1987): 1299-1302. (Year: 1987).*
Swanson, M., H. Barker, and S. A. MacFarlane. "Rapid vascular movement of tobraviruses does not require coat protein: evidence from mutated and wild-type viruses." Annals of applied biology 141.3 (2002): 259-266. (Year: 2002).*
Communication Pursuant to Article 94(3) EPC dated Feb. 28, 2019 From the European Patent Office Re. Application No. 1582422.1. (5 Pages).
Swanson et al. "Rapid Vascular Movement of Tobraviruses Does Not Require Coat Protein: Evidence From Mutated and Wild-Type Viruses", Annals of Applied Biology, XP055559973,141(3): 259-266, Dec. 2002.

(Continued)

Primary Examiner — Weihua Fan

(57) ABSTRACT

A nucleic acid construct is provided. The construct comprises a tobacco rattle virus (TRV) sequence and a nucleic acid sequence encoding a single guide RNA (sgRNA) that mediates sequence-specific cleavage in a target sequence of a genome of interest, wherein the TRV sequence is devoid of a functional 2b sequence. Also provided are plant cells comprising the construct and uses of the construct in gene editing.

21 Claims, 15 Drawing Sheets
(15 of 15 Drawing Sheet(s) Filed in Color)
Specification includes a Sequence Listing.

(56) References Cited

OTHER PUBLICATIONS

Hearing Notice Dated Aug. 3, 2017 From the Government of India, Patent Office, Intellectual Property Building Re: Application No. 2235/MUMNP/2010. (2 Pages).
Advisory Action Before the Filing of an Appeal Brief dated Apr. 8, 2013 From the US Patent and Trademark Office Re. U.S. Appl. No. 12/988,636.
Communication Pursuant to Article 94(3) EPC dated Feb. 4, 2014 From the European Patent Office Re. Application No. 09734624.1.
Communication Pursuant to Article 94(3) EPC dated Aug. 9, 2016 From the European Patent Office Re. Application No. 15165891.1.
Communication Pursuant to Article 94(3) EPC dated Mar. 12, 2013 From the European Patent Office Re. Application No. 09734624.1.
European Search Report and the European Search Opinion dated Aug. 7, 2015 From the European Patent Office Re. Application No. 15165891.1.
Examination Report dated Oct. 14, 2015 From the Government of India, Patent Office, Intellectual Property Building Re. Application No. 2235/MUMNP/2010.
Examination Report dated Feb. 22, 2012 From the Intellectual Property Office of New Zealand Re. Application No. 588767.
Examination Report dated Mar. 28, 2011 From the Intellectual Property Office of New Zealand Re. Application No. 588767.
International Preliminary Report on Patentability dated May 3, 2012 From the International Bureau of WIPO Re. Application No. PCT/IL2010/000874.
International Preliminary Report on Patentability dated Nov. 4, 2010 From the International Bureau of WIPO Re. Application No. PCT/IL2009/000432.
International Preliminary Report on Patentability dated Jun. 8, 2017 From the International Bureau of WIPO Re. Application No. PCT/IL2015/051150. (6 Pages).
International Search Report and the Written Opinion dated Jun. 2, 2010 From the International Searching Authority Re. Application No. PCT/IL09/00432.
International Search Report and the Written Opinion dated Feb. 16, 2016 From the International Searching Authority Re. Application No. PCT/IL2015/051150.
International Search Report and the Written Opinion dated Mar. 25, 2011 From the International Searching Authority Re. Application No. PCT/IL2010/000874.
Office Action and Search Report dated May 20, 2016 From the State Intellectual Property Office of the People's Republic of China Re. Application No. 201410331456.6 and Its Translation Into English.
Office Action dated Feb. 4, 2017 From the State Intellectual Property Office of the People's Republic of China Re. Application No. 201410331456.6 and Its Translation Into English. (17 Pages).
Office Action dated Jun. 4, 2012 From the Israel Patent Office Re. Application No. 208819 and Its Translation Into English.
Office Action dated Aug. 13, 2015 From the Israel Patent Office Re. Application No. 225584.
Office Action dated Jan. 13, 2014 From the State Intellectual Property Office of the People's Republic of China Re. Application No. 200980123518.1 and Its Translation Into English.
Office Action dated Oct. 22, 2014 From the Israel Patent Office Re. Application No. 225584 and Its Translation Into English.
Office Action dated Mar. 29, 2016 From the Israel Patent Office Re. Application No. 225584 and Its Translation Into English.
Official Action dated May 1, 2015 From the US Patent and Trademark Office Re. U.S. Appl. No. 14/341,999.
Official Action dated Nov. 4, 2014 From the US Patent and Trademark Office Re. U.S. Appl. No. 14/341,999.
Official Action dated Sep. 17, 2015 From the US Patent and Trademark Office Re. U.S. Appl. No. 13/502,532.
Official Action dated Oct. 18, 2016 From the US Patent and Trademark Office Re. U.S. Appl. No. 14/341,999.
Official Action dated Sep. 21, 2015 From the US Patent and Trademark Office Re. U.S. Appl. No. 14/341,999.
Official Action dated Apr. 24, 2017 from the US Patent and Trademark Office Re. U.S. Appl. No. 14/341,999.
Official Action dated Mar. 27, 2012 From the US Patent and Trademark Office Re. U.S. Appl. No. 12/988,636.
Official Action dated Apr. 28, 2016 From the US Patent and Trademark Office Re. U.S. Appl. No. 14/341,999.
Official Action dated Nov. 30, 2012 From the US Patent and Trademark Office Re. U.S. Appl. No. 12/988,636.
Requisition—Sequence Listing Dated Mar. 6, 2012 From the Canadian Intellectual Property Office Re. Application No. 2,721,372.
Restriction Official Action dated Apr. 6, 2015 From the US Patent and Trademark Office Re. U.S. Appl. No. 13/502,532.
Restriction Official Action dated Dec. 21, 2011 From the US Patent and Trademark Office Re. U.S. Appl. No. 12/988,636.
Supplementary European Search Report and the European Search Opinion dated Oct. 19, 2011 From the European Patent Office Re. Application No. 09734624.1.
Translation dated Aug. 30, 2015 of Office Action dated Aug. 13, 2015 From the Israel Patent Office Re. Application No. 225584.
Translation of Office Action dated May 3, 2012 From the State Intellectual Property Office of the People's Republic of China Re. Application No. 200980123518.1.
Translation of Office Action dated Jul. 23, 2013 From the State Intellectual Property Office of the People's Republic of China Re. Application No. 200980123518.1.
Translation of Office Action dated Mar. 25, 2013 From the State Intellectual Property Office of the People's Republic of China Re. Application No. 200980123518.1.
Translation of Search Report dated Mar. 25, 2013 From the State Intellectual Property Office of the People's Republic of China Re. Application No. 200980123518.1.
Beumer et al. "Efficient Gene Targeting in Drosophila With Zinc-Finger Nucleases", Genetics, 172(4): 2391-2403, 2006.
Canto et al. "A Cucumber Mosaic Virus (CMV) RNA 1 Transgene Mediates Suppression of the Homologous Viral RNA 1 Constitutively and prevents CMV Entry Into the Phloem", Journal of Virology, XP002558409, 75(19): 9114-9120, Oct. 2001. Fig.2, p. 9115, 1-h Col., Para 5.
Carette et al. "Cowpea Mosaic Virus 32- and 60-Kilodalton Replication Proteins Target and Change the Morphology of Endoplasmic Reticulum Membranes", Journal of Virology, XP055205027, 76(12): 6293-6301, Jun. 15, 2002. Fig. 1.
Chapman et al. "Potato Virus X as a Vector for Gene Expression in Plants", The Plant Journal, 2(4): 549-557, 1992.
Dolja et al. "Isolation and Stability of Histidine-Tagged Proteins Produced in Plants Via Potyvirus Gene Vectors", Virology, 252(1): 269-274, 1998.
Dolja et al. "Tagging of Plant Potyvirus Replication and Movement by Insertion of Beta-Glucuronidase Into the Viral Polyprotein", Proc. Natl. Acad. Sci. USA, 89: 10208-10212, 1992.
Donson et al. "Systemic Expression of a Bacterial Gene by a Tobacco Mosaic Virus-Based Vector", Proc. Natl. Acad. Sci. USA, 88(16): 7204-7208, 1991.
Feng et al. "Efficient Genome Editing in Plants Using a CRISPR/Cas System", Cell Research, 23: 1229-1232, Published Online Aug. 20, 2013.
Gallie et al. "The 5'-Leader Sequence of Tobacco Mosaic Virus RNA Enhances the Expression of Foreign Gene Transcripts In Vitro and In Vivo", Nucleic Acids Research, 15(8): 3257-3273, Dec. 31, 1987. Abstract.
Gao et al. "Self-Processing of Ribozyme-Flanked RNAs Into Guide RNAs In Vitro and In Vivo for CRISPR-Mediated Genome Editing", Journal of Integrative Plant Biology, 56(4): 343-349, Apr. 2014.
Gao et al. "Specific and Heritable Gene Editing in *Arabidopsis*", Proc. Natl. Acad. Sci. USA, PNAS, 111(12): 4357-4358, Mar. 25, 2014. p. 4357, Last Para, p. 4358, Middle Col., First Para.
Gleba et al. "Engineering Viral Expression Vectors for Plants: the 'Full Virus' and the 'Deconstructed Virus' Strategies", Current Opinion in Plant Biology, 7: 182-188, 2004.
Gleba et al. "Viral Vectors for the Expression of Proteins in Plants", Current Opinion in Biotechnology, 18: 134-141, 2007.
Goldbach et al. "Plant Viruses as Gene Vectors", Methods in Plant Biochemistry, 106: 103-120, 1997.

(56) References Cited

OTHER PUBLICATIONS

Goulden et al. "Pea Early Browning Virus (Isolate TPA56) RNA2 Complete Sequence, Encoding Coat Protein, 9kDa Protein and 23kDa Protein", GenBank FASTA, GenBank: X78455.1, GenBank Accession No. X78455, Aug. 30, 1995.
Goulden et al. "The Complete Nucleotide Sequence of PEBV RNA2 Reveals the Presence of a Novel Open reading Frame and Provides Insights Into the Structure of Tobraviral Subgenomic Promoters", Nucleic Acids Research, EMBL Accession No. X51828, 18(15); 4507-4512, 1990. Abstract, p. 4510.
Greenboim-Wainberg et al. "Cross Talk Between Gibberellin and Cytokinin: The *Arabidopsis* GA Response Inhibitor SPINDLY Plays a Positive Role in Cytokinin Signaling", Plant Cell, XP002623000, 17(1): 92-102, Jan. 2005.
Hernandez et al. "Sequence of RNA 2 of a Nematode-Transmissible Isolate of Tobacco Rattle Virus", Journal of General Virology, XP002973633, 76(Pt.11): 2847-2851, Jan. 1995.
Hernandez et al. "Tobacco Rattle Virus Genes for Coat Protein, 28.7 kDa & 32.8 kDa Proteins, Genomic RNA", GenBank NCBI [Online], GenBank: Z36974.2, GenBank Accession No. Z36974, Oct. 21, 2003.
Isalan "Zinc-Finger Nucleases: How to Play Two Good Hands", Nature Method 9(1):32-34, Jan. 2012.
Jiang et al. "Demonstration of CRISPR/Cas9/SgRNA-Mediated Targeted Gene Modification in *Arabidopsis*, Tobacco, Sorghum and Rice", Nucleic Acid Research, 41(20): e188-1-e188-12, Published Online Sep. 2, 2013.
Li et al. "Multiplex and Homologous Recombination-Mediated Genome Editing in *Arabidopsis* and Nicotiana Benthamiana Using Guide RNA and Cas9", Nature Biotechnology, 31(8): 688-691, Aug. 2013.
Liu et al. "Functional Replacement of the Tobacco Rattle Virus Cysteine-Rich Protein by Pathogenicity Proteins From Unrelated Plant Viruses", Virology, XP002222989, 298(2): 232-239, Jul. 5, 2002. Fig.1, Notes of Fig.1.
Liu et al. "Tobacco Rattle Virus RNA2-Based VIGS Vector pTRV2, Complete Sequence", Database NCBI [Online], GenBank Accession No. AF406991.1, Database Accession No. AF406991, Nov. 13, 2003.
Liu et al. "Tobacco Rattle Virus Segment RNA1, Complete Sequence", Database NCBI [Online], GenBank Accession No. AF406990.1, Database Accession No. AF406990, Jun. 11, 2002.
Lloyd et al. "Targeted Mutagenesis Using Zinc-Finger Nucleases in *Arabidopsis*", Proc. Natl. Acad. Sci. USA, PNAS, XP055008257, 102(6): 2232-2237, Feb. 8, 2005.
MacFarlane et al. "Efficient Expression of Foreign Proteins in Roots From Tobravirus Vectors", Virology, XP004436150, 267(1): 29-35, Feb. 1, 2000. Fig.1, p. 30, 1-h Col., Last Para.
Mao et al. "Application of the CRISPR-Cas System for Efficient Genome Engineering in Plants", Molecular Plant, 6(6): 2008-2011, Advance Access Publication Aug. 12, 2013.
Marton et al. "Nontransgenic Genome Modification in Plant Cells", Plant Physiology, 154: 1079-1087, Nov. 2010.
Miao et al. "Targeted Mutagenesis in Rice Using CRISPR-Cas System", Cell Research, 23: 1233-1236, Published Online Sep. 3, 2013.
Moehle et al. "Targeted Gene Addition Into a Special Occasion in the Human Genome Using Designed Zinc Finger Nucleases", Proc. Natl. Acad. Sci. USA, 104: 3055-3060, 2007.
Nekrasov et al. "Targeted Mutagenesis in the Model Plant Nicotiana Benthamiana Using Cas9 RNA-Guided Endonuclease", Nature Biotechnology, 31(8): 691-693, Aug. 2013.
Papworth et al. "Designer Zinc-Finger Proteins and Their Applications", Gene, XP005282076, 366(1): 27-38, Jan. 17, 2006. Para [06.3], Fig.4.
Pogue "Making an Ally From an Enemy: Plant Virology and the New Agriculture", Annual Reviews in Phytopathology, 40: 45-74, 2002.
Puchta et al. "Two Different but Related Mechanisms Are Used in Plants for the Repair of Genomic Double-Strand Breaks by Homologous Recombination", Proc. Natl. Acad. Sci. USA, 93(10): 5055-5060, 1996.
Ratcliff et al. "Gene Silencing Without DNA: RNA-Mediated Cross-Protection Between Viruses", The Plant Cell, XP000827858, 11: 1207-1215, Jul. 1999. Fig.1, p. 1208, r-h Col.
Ratcliff et al. "Tobacco Rattle Virus as a Vector for Analysis of Gene Function by Silencing", The Plant Journal, XP002184551, 25(2): 237-245, Jan. 2001.
Salomon et al. "Capture of Genomic and T-DNA Sequences During Double-Strand Break Repair in Somatic Plant Cells", The EMBO Journal, 17(20): 6086-6095, 1998.
Senthil-Kumar et al. "Tobacco Rattle Virus-Based Virus-Induced Gene Silencing in Nicotiana Benthamiana", Nature Protocols, 9(7): 1549-1562, Published Online Jun. 5, 2014. Abstract, p. 1550, Last Para—p. 1551, First Para, Suppl. Fig.1.
Shan et al. "Targeted Genome Modification of Crop Plants Using CRISPR-Cas System", Nature Biotechnology, 31(8): 686-688, Aug. 2013.
Tang et al. "Application of Gene Silencing Induced by Tobacco Rattle Virus in Plant Gene Function Study", Chemistry of Life, 26(4): 360363, Aug. 31, 2006. English Abstract.
Tzfira et al. "Agrobacterium T-DNA Integration: Molecules and Models", Trends in Genetics, 20(8): 375-383, 2004.
Tzfira et al. "Site-Specific Integration of Agrobacterium Tumefaciens T-DNA Via Double-Stranded Intermediate", Plant Physiology, 133(3): 1011-1023, 2003.
Vassilakos et al. "Tobravirus 2b Protein Acts in Trans to Facilitate Transmission by Nematodes", Virology, XP055205048, 279(2): 478-487, Jan. 2001. Fig.5.
Vellios et al. "Immunogold Localization of Tobravirus 2b Nematode Transmission Helper Protein Associated With Virus Particles", Virology, 300: 118-124, 2002.
Xie et al. "RNA-Guided Genome Editing in Plants Using a CRISPR-Cas System", Molecular Plant, 6(6): 1975-1983, Advance Access Publication Aug. 17, 2013.
Zhang et al. "A Narcissus Mosaic Viral Vector System for Protein Expression and Flavonoid Production", Plant Methods 9(28):1-13, Jul. 13, 2013.
Supplementary European Search Report and the European Search Opinion dated Apr. 19, 2018 From the European Patent Office Re. Application No. 15862422.1. (9 Pages).
Zahir et al. "Activity and Specificity of TRV-Mediated Gene Editing in Plants", Plant Signaling & Behavior, XP055465491, 10(10): e1044191-1-e1044191-5, Oct. 2015. Abstract, p. 2, col. 1, Para 1.
Zaidi et al. "Viral Vectors for Plant Genome Engineering", Frontiers in Plant Science, XP055465212, 8(Art.539): 1-6, Apr. 11, 2017. p. 4, col. 2, Para 2—p. 5, col. 1, Para 1, Table 1.
Communication Pursuant to Article 94(3) EPC dated Nov. 29, 2019 From the European Patent Office Re. Application No. 1582422.1. (4 Pages).
Communication Pursuant to Article 94(3) EPC dated Aug. 4, 2020 From the European Patent Office Re. Application No. 1582422.1. (4 Pages).

\* cited by examiner

Map of TRV RNA2-Ribozyme-NptII-sgRNA ribozyme :DsRed construct:

Map of TRV RNA2-Ribozyme-PDS-sgRNA ribozyme:-DsRed construct:

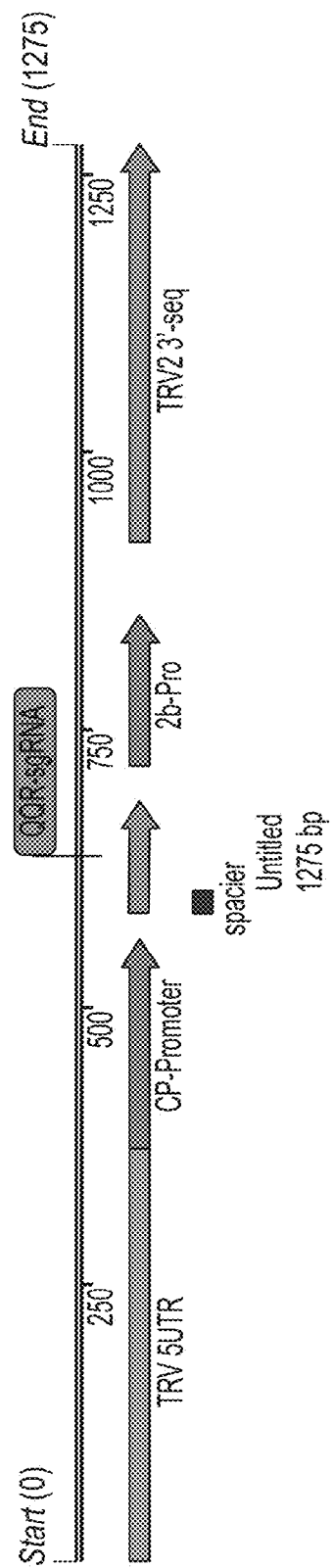
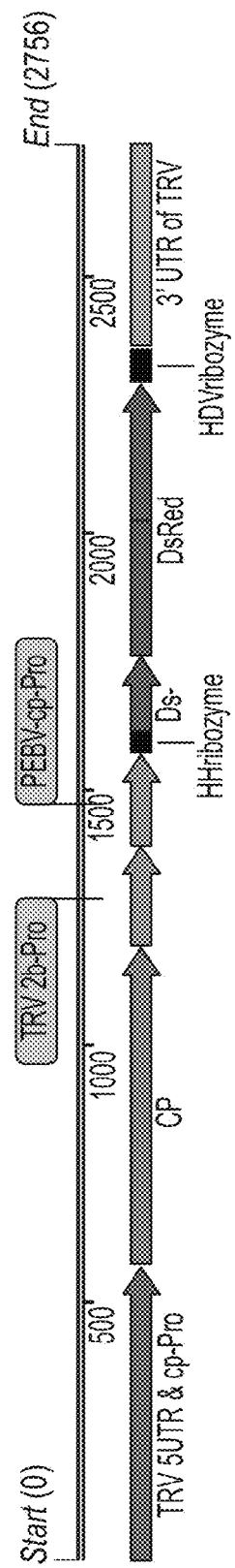
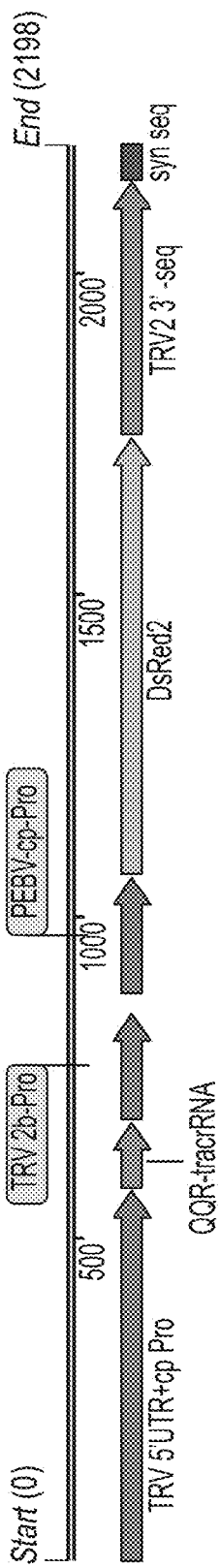
Figure 1C
Map of RNA2-CP-sgP-QQR-sgRNA construct (no ribosyme):
Figure 1D
Map of TRV RNA2 expressing DsRed2 flanked by ribozymes
Figure 1E
Map of TRV RNA2 expressing both QQR-sgRNA and DsRed Map of pK7WGF2-hCas9 a binary vector for expression of hCas9

Figure 3A

| | | |
|---|---|---|
| wt | atgccgccgtgttccggctgtcagcgcagggcgccggttctttttgtcaagaccgacctgtccggtgccct | (SEQ ID NO: 29) |
| -8bp | ATGCCGCCGCCGTGTTCCGGCTGTCAGCGC-------CCGGTTCTTTTTGTCAAGACCGACCTGTCCGGTGCCCT | (SEQ ID NO: 30) |
| -8bp | ATGCCGCCGCCGTGTTCCGGCTGTCAGCGCA------CGGTTCTTTTTGTCAAGACCGACCTGTCCGGTGCCCT | (SEQ ID NO: 31) |
| -2bp | ATGCCGCCGCCGTGTTCCGGCTGTCAGCGCAGGGGC--CCGGTTCTTTTTGTCAAGACCGACCTGTCCGGTGCCCT | (SEQ ID NO: 32) |
| +1bp | ATGCCGCCGCCGTGTTCCGGCTGTCAGCGCAGCGCAGGGGCGCCGGTTCTTTTTGTCAAGACCGACCTGTCCGGTGCCCT | (SEQ ID NO: 33) |
| +1bp | ATGCCGCCGCCGTGTTCCGGCTGTCAGCGCAGGGGCTGCCGGTTCTTTTTGTCAAGACCGACCTGTCCGGTGCCCT | (SEQ ID NO: 34) |
| -10bp | ATGCCGCCGCCGTGTTCCGGCTGTCAGCGCGTC----------GCCGGTTCTTTTTGTCAAGACCGACCTGTCCGGTGCCCT | (SEQ ID NO: 35) |
| +1bp | ATGCCGCCGCCGTGTTCCGGCTGTCAGCGCAGCGCAGGGGCAGCCGGTTCTTTTTGTCAAGACCGACCTGTCCGGTGCCCT | (SEQ ID NO: 36) |
| +1bp | ATGCCGCCGCCGTGTTCCGGCTGTCAGCGCAGGGGGAGCCGGTTCTTTTTGTCAAGACCGACCTGTCCGGTGCCCT | (SEQ ID NO: 37) |
| -1bp | ATGCCGCCGCCGTGTTCCGGCTGTCAGCGCAGGGG-GCCCGGTTCTTTTTGTCAAGACCGACCTGTCCGGTGCCCT | (SEQ ID NO: 38) |
| +1bp | ATGCCGCCGCCGTGTTCCGGCTGTCAGCGCAGGGGAGCCGGTTCTTTTTGTCAAGACCGACCTGTCCGGTGCCCT | (SEQ ID NO: 39) |
| +1bp | ATGCCGCCGCCGTGTTCCGGCTGTCAGCGCAGGGGCGCCGGTTCTTTTTGTCAAGACCGACCTGTCCGGTGCCCT | (SEQ ID NO: 40) |
| -8bp | ATGCCGCCGCCGTGTTCCGGCTGTCAGCGC--------CCGGTTCTTTTTGTCAAGACCGACCTGTCCGGTGCCCT | (SEQ ID NO: 41) |

Figure 3B

| | | |
|---|---|---|
| WT | TAAAATGCCCCAAAATTGGACTTGTTTCTGCCGTTAATTCAGCTTATCTTTGGAGC | (SEQ ID NO: 42) |
| +1bp | TAAAATGCCCCAAAATTGGACTTGTTTCTGCCGTTAATTCAGCTTATCTTTGGAGC | (SEQ ID NO: 43) |
| +1bp | TAAAATGCCCCAAAATTGGACTTGTTTCTGCCGTTAATTCAGCTTATCTTTGGAGC | (SEQ ID NO: 44) |
| -3bp | TAAAATGCCCCAAAATGGACTTGTTTCGCCGTTAATTCAGCTTATCTTTGGAG | (SEQ ID NO: 45) |

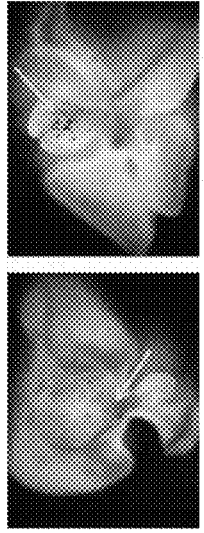

```
ctgcagtcgacggtaccatgtgttcttcccctcctgaggggaagaattacgtcctgtagaaaccccaacccgtga   WT (SEQ ID NO: 46)
gacgtcagctgccatggtacaagaagggagactcccttcttaatgcaggacatctttggggttgggcact   (SEQ ID NO: 108)
                                       sgRNA QCR 3325
                                  PAM ctgcagtcgacggtaccatgtgttcttcccctcctgaggggaagaattacgtcctgtagaaaccccaacccgtga   WT         (SEQ ID NO: 46)
CTGCAGTCGACGGTACCATGTGTTCTTCCCTC----GGGGAAGAATTACGTCCTGTAGAAACCCAACCCGTGA    -4bp       (SEQ ID NO: 47)
CTGCAGTCGACGGTACCATGTGTTCTTCCCTCCaAGAGGGGAAGAATTACGTCCTGTAGAAACCCCAACCCGTGA  -1+1bp     (SEQ ID NO: 48)
```

Figure 7A   Figure 7B

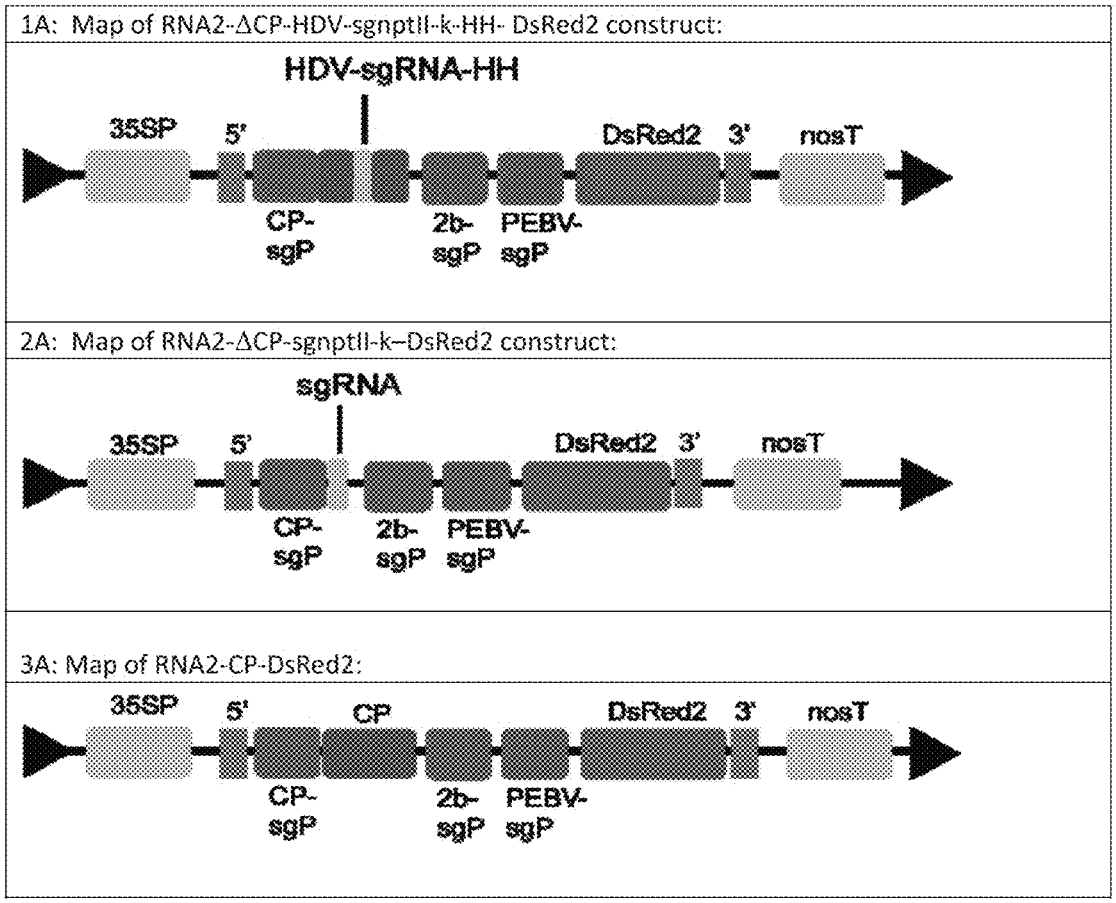
Figure 8
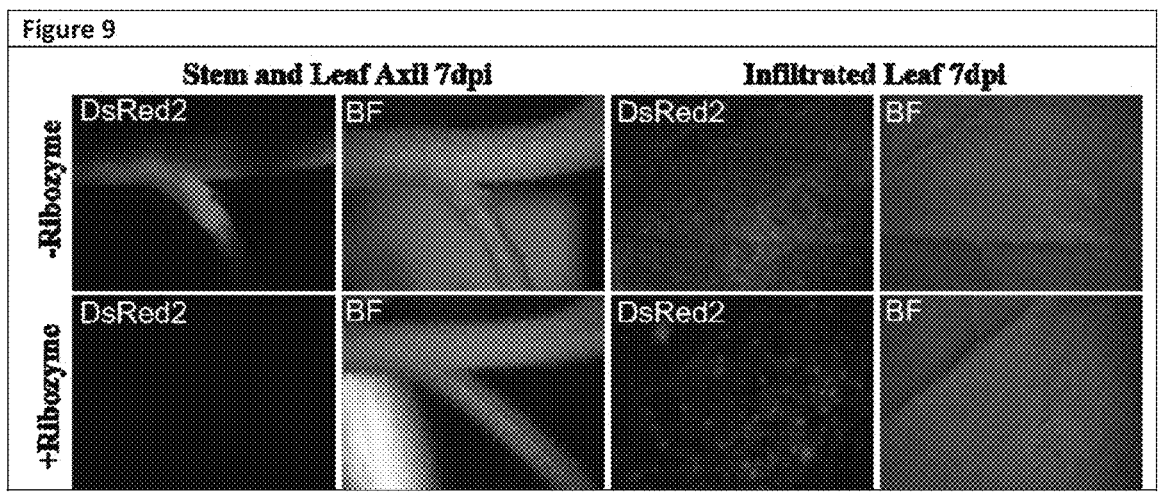

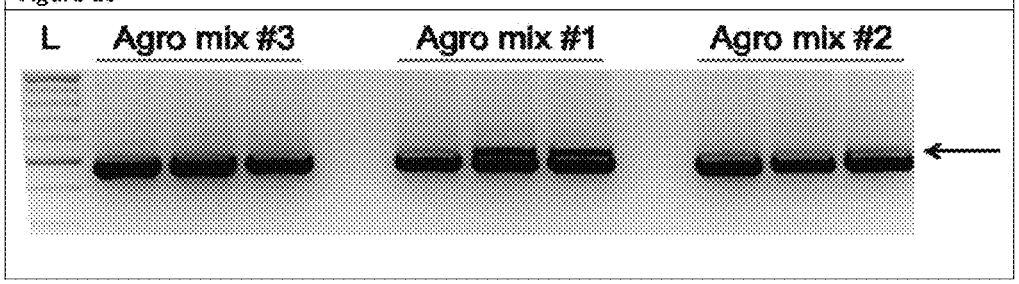

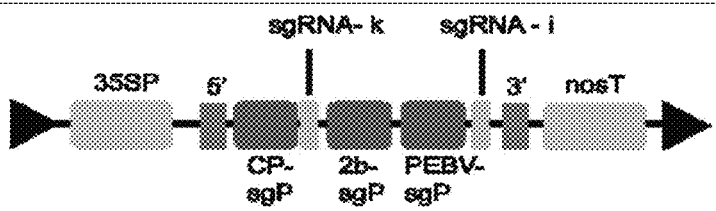
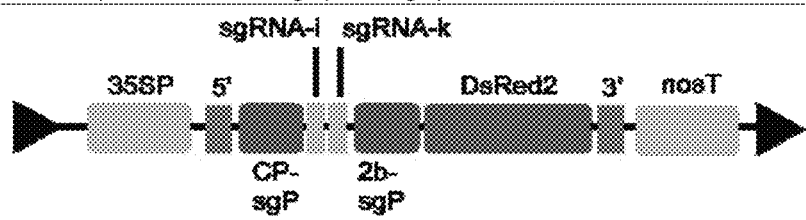
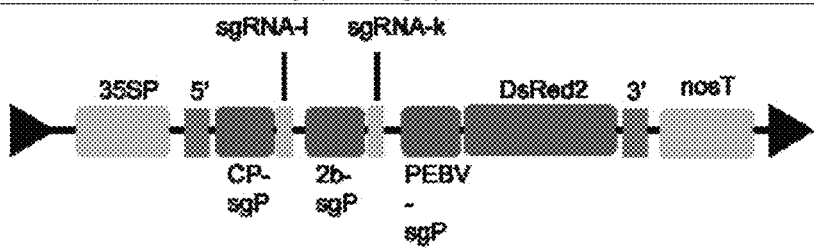
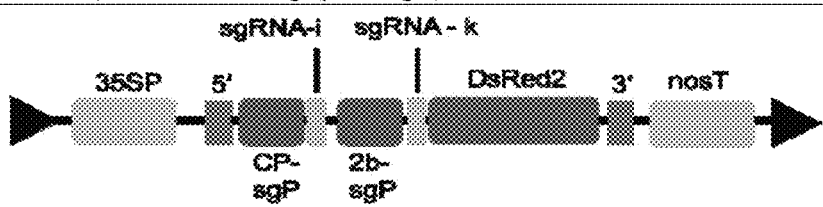
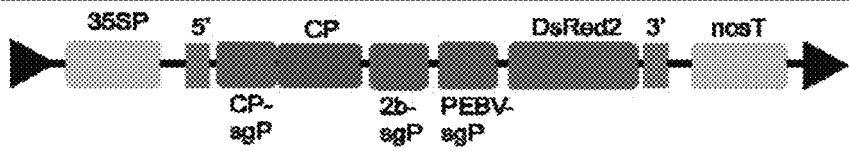
Figure 12

Figure 13

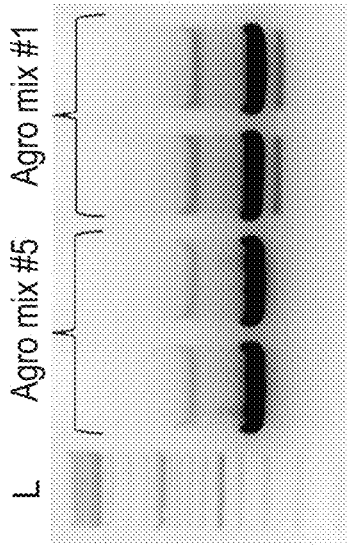

Figure 14

| | | |
|---|---|---|
| NptII.WT<br>NptII.Del | AGACAATCGGCTGCTCTGATGCCGCCGTGTTCCGGCTGTCAGCCAGGGCGGCTT<br>AGACAATCGGCTGCTCTGATGCCGCCGCGTGTTCCGGCTGTCAAGCCAGGGC------<br>********************************************** | (SEQ ID 58)<br>(SEQ ID 60) |
| NptII.WT<br>NptII.Del | CTTTTTGTCAAGACCGACCTGTCCGGTGCCCTGAATGAACTGCAGGAGGAGGCGG<br>-------------------------------------------------------<br> | (SEQ ID 58) cont.<br>(SEQ ID 60) cont. |
| NptII.WT<br>NptII.Del | GCTATCGTGGCTGGCCACGACGGGCGTTCCTTGCGCAGCTGTGCTCGACGTTGTCACTG<br>-------------------------------------------------------<br> | (SEQ ID 58) cont.<br>(SEQ ID 60) cont. |
| NptII.WT<br>NptII.Del | AAGCGGAAGGGAC<br>AACCCCAACCCAC<br>********** | (SEQ ID 58) cont.<br>(SEQ ID 60) cont. |

Figure 15

Deletions:

```
CAGACAATCGGCTGCTCTGATGCCGCGTGTTCCGGTGTGTCAGCGCAGGGGCGCCGGTTCTTTTTGTCAAGAC WT   (SEQ ID 110)
         ATCGGCTGCTCTGATGCCGCCG..............................................  150bp (SEQ ID 64)
AGACAATCGGCTGCTCTGATGCCGCGTGTTCCGGTGTCAGCGCAGGGGC..............................  126bp (SEQ ID 60)
AGACAATCGGCTGCTCTGATGCCGCGTGTTCCGGTGTTCCGGCTG................................... 139bp (SEQ ID 62)
AGACAATCGGCTGCTCTGATGCCGCGTGTTCCGGTGTCAGCGCAGGGGC..............................  126bp (SEQ ID 60)
AGACAATCGGCTGCTCTGATGCCGCCGTGTTC................................................ 145bp (SEQ ID 63)
AGACAATCGGCTGCTCTGATGCCGCCGTGTTCCGGCTGT.......................................... 138bp (SEQ ID 61)

GGGCGTTCCTTGGCGCAGCTGTGCTGTCGACGTTGTCACTGAAGGGGAAGGGGACTGGCTGCTGCTATTGGGCGAAGTGC WT (SEQ ID 111)
................................AAGCGGGAAGGGGACTGGCTGCTGCTATTGGGCGAAGTGC 150bp (SEQ ID 64 cont.)
.......................................AAGCGGGAAGGGGACTGGCTGCTGCTATTGGGCGAAGTGC 126bp (SEQ ID 60 cont.)
................................................CTATTGGGCGAAGTGC 139bp (SEQ ID 62 cont.)
.......................................AAGCGGGAAGGGGACTGGCTGCTGCTATTGGGCGAAGTGC 126bp (SEQ ID 60 cont.)
.......................................AAGCGGGAAGGGGACTGGCTGCTGCTATTGGGCGAAGTGC 145bp (SEQ ID 63 cont.)
.......................................AAGCGGGAAGGGGACTGGCTGCTGCTATTGGGCGAAGTGC 138bp (SEQ ID 61 cont.)
```

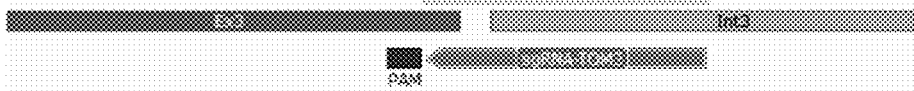

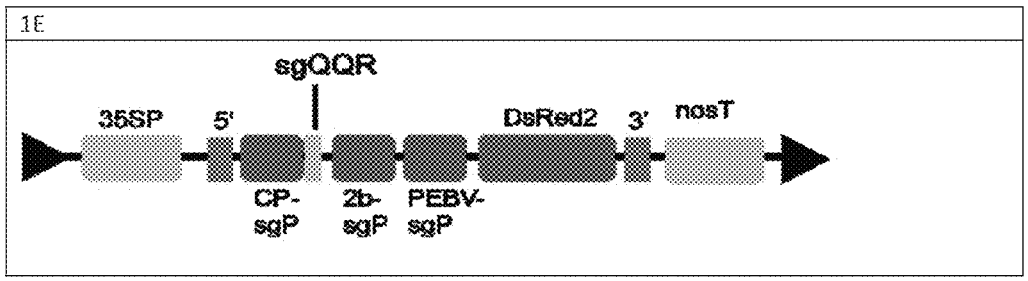
Figure 22
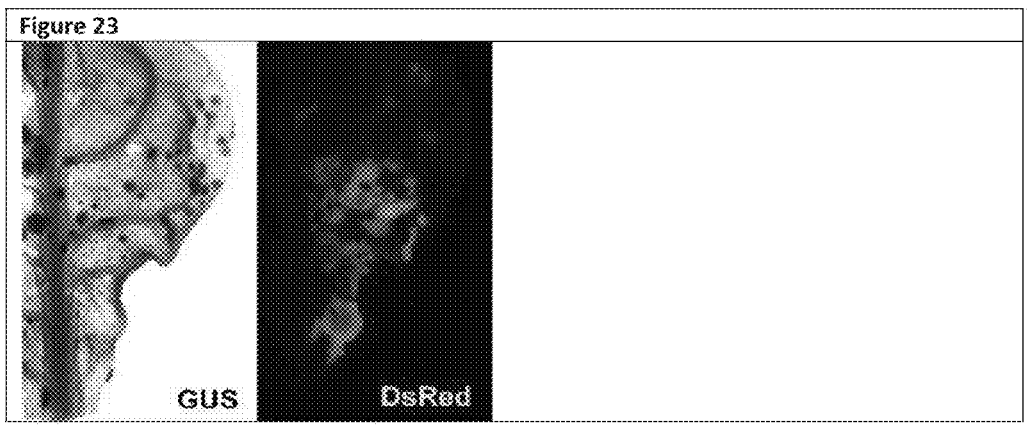
Figure 23
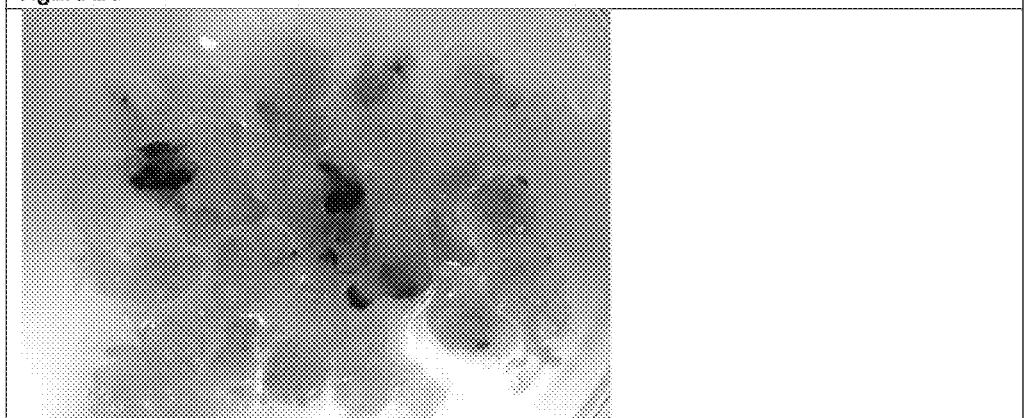
Figure 24
Figure 25

Figure 26

Figure 27

| Plant 5C: (-1bp) SEQ ID 69 | |
|---|---|
| WT catgttcttccctcctgaggggaagaattacgtcctgtagaaacccaacccgtgaaatcaaaaaact | (SEQ ID NO: 116) |
| T0 CATGTTCTTCCCCTC_TGAGGGGAAGAATTACGTCCTGTAGAAACCCCAACCCGTGAAATCAAAAAACT | (SEQ ID NO: 69) |
| T1 CATGTTCTTCCCCTC_TGAGGGGAAGAATTACGTCCTGTAGAAACCCCAACCCGTGAAATCAAAAAACT | (SEQ ID NO: 69) |
| Plant 5F: (-1bp) SEQ ID 70 | |
| WT taccatgttcttccctcctgaggggaagaattacgtcctgtagaaacccaacccgtgaaatcaaaaaact | (SEQ ID NO: 116) |
| T0 TACCATGTTCTTCCCCTC_TGAGGGGAAGAATTACGTCCTGTAGAAACCCCAACCCGTGAAATCAAAAAACT | (SEQ ID NO: 70) |
| T1 TACCATGTTCTTCCCCTC_TGAGGGGAAGAATTACGTCCTGTAGAAACCCCAACCCGTGAAATCAAAAAACT | (SEQ ID NO: 70) |
| Plant 5H: (-1bp) SEQ ID 71 | |
| WT taccatgttcttccctcctgaggggaagaattacgtcctgtagaaacccaacccgtgaaatcaaaaaac | (SEQ ID NO: 116) |
| T0 TACCATGTTCTTCCCCTC_TGAGGGGAAGAATTACGTCCTGTAGAAACCCCAACCCGTGAAATCAAAAAAC | (SEQ ID NO: 71) |
| T1 TACCATGTTCTTCCCCTC_TGAGGGGAAGAATTACGTCCTGTAGAAACCCCAACCCGTGAAATCAAAAAAC | (SEQ ID NO: 71) |
| Plant 6A: (-4bp) SEQ ID 72 | |
| WT taccatgttcttccctcctgaggggaagaattacgtcctgtagaaacccaacccgtgaaatcaaaaaact | (SEQ ID NO: 116) |
| T0 TACCATGTTCTTCCCCTC____GGGAAGAATTACGTCCTGTAGAAACCCCAACCCGTGAAATCAAAAAACT | (SEQ ID NO: 72) |
| T1 TACCATGTTCTTCCCCTC____GGGAAGAATTACGTCCTGTAGAAACCCCAACCCGTGAAATCAAAAAACT | (SEQ ID NO: 72) |
| Plant 7B: (+1bp) SEQ ID 73 | |
| WT catgttcttccctc ctgaggggaagaattacgtcctgtagaaacccaacccgtgaaatcaaaaaac | (SEQ ID NO: 116) |
| T0 CATGTTCTTCCCCTC_TGAGGGGAAGAATTACGTCCTGTAGAAACCCCAACCCGTGAAATCAAAAAAC | (SEQ ID NO: 73) |
| T1 CATGTTCTTCCCCTC_TGAGGGGAAGAATTACGTCCTGTAGAAACCCCAACCCGTGAAATCAAAAAAC | (SEQ ID NO: 73) |
| Plant 8A: (-16bp) SEQ ID 74 | |
| WT taccatgttcttccctcctgaggggaagaattacgtcctgtagaaacccaacccgtgaaatcaaaaaac | (SEQ ID NO: 116) |
| T0 TACCATGTTCTTCCC_____CCCAACCCGTGAAATCAAAAAAC | (SEQ ID NO: 74) |
| T1 TACCATGTTCTTCCCCTC_____GTCCTGTAGAAACCCCAACCCGTGAAATCAAAAAAC | (SEQ ID NO: 74) |

…

NUCLEIC ACID CONSTRUCTS FOR GENOME EDITING

RELATED APPLICATIONS

This application is a National Phase of PCT Patent Application No. PCT/IL2015/051150 having International filing date of Nov. 26, 2015, which claims the benefit of priority under 35 USC § 119(e) of U.S. Provisional Patent Application No. 62/085,292 filed on Nov. 27, 2014. The contents of the above applications are all incorporated by reference as if fully set forth herein in their entirety.

SEQUENCE LISTING STATEMENT

The ASCII file, entitled 70201SequenceListing.txt, created on May 28, 2017, comprising 109,777 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to nucleic acid constructs for genome editing and more specifically to tobacco rattle virus (TRV) based nucleic acid constructs which express elements of an oligonucleotide-enzyme complex for targeted genome alternations, e.g., the CRISPR/Cas9 system.

The CRISPR/Cas9 system (Clustered Regularly Interspaced Short Palindromic Repeats/CRISPR-associated endonuclease9) has been shown to mediate efficient genome editing in a wide range of organisms including, human, yeast, zebra fish nematodes, drosophila and plants as well as in several other organisms.

CRISPR provides a simple approach for targeted gene disruption and targeted gene insertion. The major elements for gene disruption include the Cas9 protein that contains the nuclease domain and the guide RNA (sgRNA) that provides sequence specificity to the target RNA (Johnson et. al. Comparative assessments of CRISPR-Cas nucleases' cleavage efficiency in planta. 2014. Plant Mol Biol. November 18.). The first 20 nucleotide sequence at the 5'-end of the sgRNA is complementary to the target sequence and it provides specificity for the CRISPR/Cas9 system. The 3' portion of the sgRNA forms secondary structures required for Cas9 activities. The sgRNA brings the Cas9 nuclease to the specific target and subsequently Cas9 generates double-stranded breaks in the target DNA at the protospacer-adjacent motif (PAM) site. Non-homologous end-joining repair of the double-stranded breaks often leads to deletions or small insertions (indels) that disrupt the target gene.

Methods for stable modification of plant genomes using the CRISPR/Cas9 are still under development.

Additional Background Art Includes:
US20140273235;
(i) Nekrasov V, Staskawicz B, Weigel D, Jones J D, Kamoun S: Targeted mutagenesis in the model plant *Nicotiana benthamiana* using Cas9 RNA-guided endonuclease. *Nat Biotechnol* 2013, 31:691-693;
(ii) Shan Q, Wang Y, Li J, Zhang Y, Chen K, Liang Z, Zhang K, Liu J, Xi J J, Qiu J L, Gao C: Targeted genome modification of crop plants using a CRISPR-Cas system. *Nat Biotechnol* 2013, 31:686-688;
(iii) Li J F, Norville J E, Aach J, McCormack M, Zhang D, Bush J, Church G M, Sheen J: Multiplex and homologous recombination-mediated genome editing in *Arabidopsis* and *Nicotiana benthamiana* using guide RNA and Cas9. *Nat Biotechnol* 2013, 31:688-691;
(iv) Feng Z, Zhang B, Ding W, Liu X, Yang D L, Wei P, Cao F, Zhu S, Zhang F, Mao Y, Zhu J K: Efficient genome editing in plants using a CRISPR/Cas system. *Cell Res* 2013, 23:1229-1232;
(v) Mao Y, Zhang H, Xu N, Zhang B, Gao F, Zhu J K: Application of the CRISPR-Cas system for efficient genome engineering in plants. *Mol Plant* doi:10.1093/mp/sst121 (Aug. 20, 2013);
(vi) Xie K, Yang Y: RNA-guided genome editing in plants using a CRISPR-Cas system. *Mol Plant* doi:10.1093/mp/sst119 (Aug. 17, 2013);
(vii) Miao J, Guo D, Zhang J, Huang Q, Qin G, Zhang X, Wan J, Gu H, Qu L J: Targeted mutagenesis in rice using CRISPR-Cas system. *Cell Res* 2013, 23:1233-1236;
(viii) Jiang W, Zhou H, Bi H, Fromm M, Yang B, Weeks D P: Demonstration of CRISPR/Cas9/sgRNA-mediated targeted gene modification in *Arabidopsis*, tobacco, sorghum and rice. *Nucleic Acids Res* doi:10.1093/nar/gkt780 (Sep. 2, 2013).

SUMMARY OF THE INVENTION

According to an aspect of some embodiments of the present invention there is provided a nucleic acid construct comprising a tobacco rattle virus (TRV) sequence and a nucleic acid sequence encoding a single guide RNA (sgRNA) that mediates sequence-specific cleavage in a target sequence of a genome of interest, wherein the TRV sequence is devoid of a functional 2b sequence.

According to some embodiments of the invention, the TRV is devoid of a functional coat protein.

According to some embodiments of the invention, the TRV comprises a heterologous enhancer sequence.

According to some embodiments of the invention, the heterologous enhancer sequence comprises an Ω enhancer.

According to some embodiments of the invention, the nucleic acid sequence encoding the sgRNA is flanked by ribozyme sequences.

According to some embodiments of the invention, the ribozyme sequences are non-identical.

According to some embodiments of the invention, the sgRNA comprises at least two sgRNAs.

According to some embodiments of the invention, the at least two sgRNAs are directed to a single target gene.

According to some embodiments of the invention, the at least two sgRNAs are directed to different target genes.

According to some embodiments of the invention, transcription of the at least two sgRNAs is by a single promoter.

According to some embodiments of the invention, the nucleic acid construct further comprises an additional nucleic acid sequence encoding a nuclease which binds the sgRNA to cleave genomic DNA in a sequence specific manner.

According to some embodiments of the invention, the nuclease is Cas9 or RISC.

According to some embodiments of the invention, the target sequence is endogenous to the genome of interest.

According to some embodiments of the invention, the target sequence is exogenous to the genome of interest.

According to some embodiments of the invention, transcription of the sgRNA and the nuclease is regulated by two separate promoters.

According to some embodiments of the invention, the TRV comprise a TRV1 and TRV2.

According to some embodiments of the invention, the TRV comprise a TRV2.

According to an aspect of some embodiments of the present invention there is provided a nucleic acid construct system comprising the nucleic acid construct; and a nucleic acid construct encoding a nuclease which binds the sgRNA to cleave genomic DNA in a sequence specific manner.

According to some embodiments of the invention, the nuclease is Cas9 or RISC.

According to an aspect of some embodiments of the present invention there is provided a cell comprising the nucleic acid construct or construct system.

According to some embodiments of the invention, the cell is a plant cell.

According to an aspect of some embodiments of the present invention there is provided a plant comprising the plant cell.

According to an aspect of some embodiments of the present invention there is provided a plant part of the plant.

According to some embodiments of the invention, the plant part is a meristem.

According to an aspect of some embodiments of the present invention there is provided a method of generating genotypic variation in a genome of a plant, the method comprising introducing into the plant the nucleic acid construct or the nucleic acid construct system, wherein the (sgRNA) mediates sequence-specific cleavage in a target sequence of the plant, thereby generating genotypic variation in the genome of the plant.

According to some embodiments of the invention, the variation is selected from the group consisting of a deletion, an insertion and a point mutation.

According to an aspect of some embodiments of the present invention there is provided a method of generating a herbicide resistant plant, the method comprising introducing into the plant the nucleic acid construct or the nucleic acid construct system, wherein the (sgRNA) mediates sequence-specific cleavage in a target sequence of a gene of the plant conferring sensitivity to herbicides, thereby generating the herbicide resistant plant.

According to an aspect of some embodiments of the present invention there is provided a method of generating a pathogen resistant plant, the method comprising introducing into the plant the nucleic acid construct or the nucleic acid construct system, wherein the (sgRNA) mediates sequence-specific cleavage in a target sequence of a gene of the plant conferring sensitivity to a pathogen, thereby generating the pathogen resistant plant.

According to an aspect of some embodiments of the present invention there is provided a method of generating a pathogen resistant plant, the method comprising introducing into the plant the nucleic acid construct or the nucleic acid construct system, wherein the (sgRNA) mediates sequence-specific cleavage in a target sequence of a gene of the pathogen, thereby generating the pathogen resistant plant.

According to an aspect of some embodiments of the present invention there is provided a method of generating a plant with increased abiotic stress tolerance, the method comprising introducing into the plant the nucleic acid construct or the nucleic acid construct system, wherein the (sgRNA) mediates sequence-specific cleavage in a target sequence of a gene of the plant conferring sensitivity to abiotic stress, thereby generating the plant with increased abiotic stress tolerance.

According to some embodiments of the invention, the plant is a dicotyledonous plant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
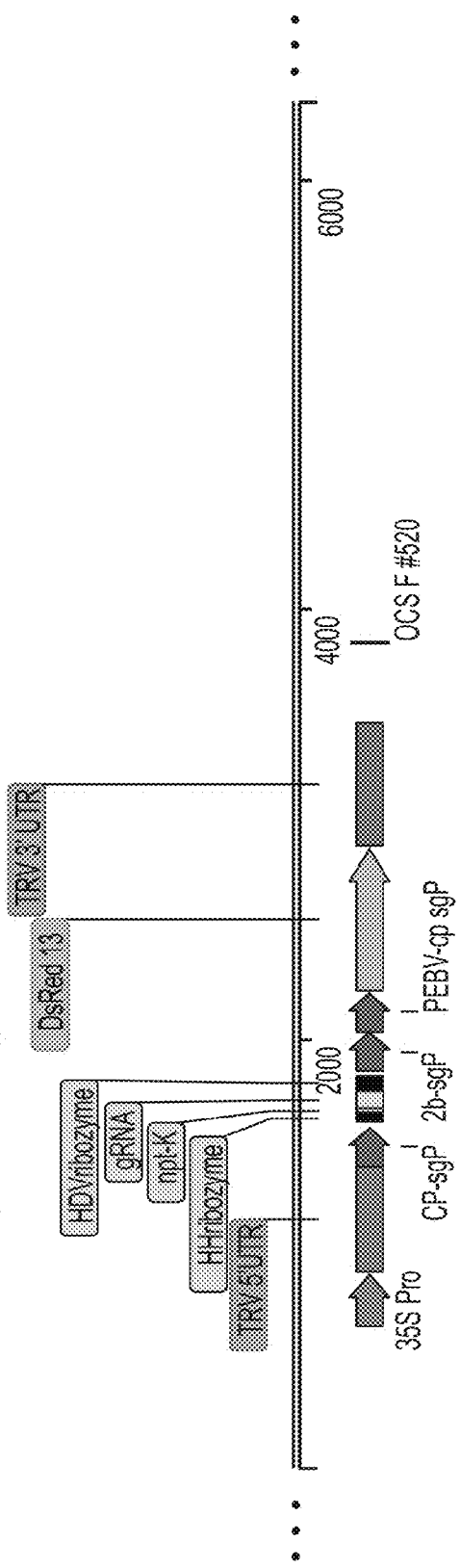
Figure 1B:
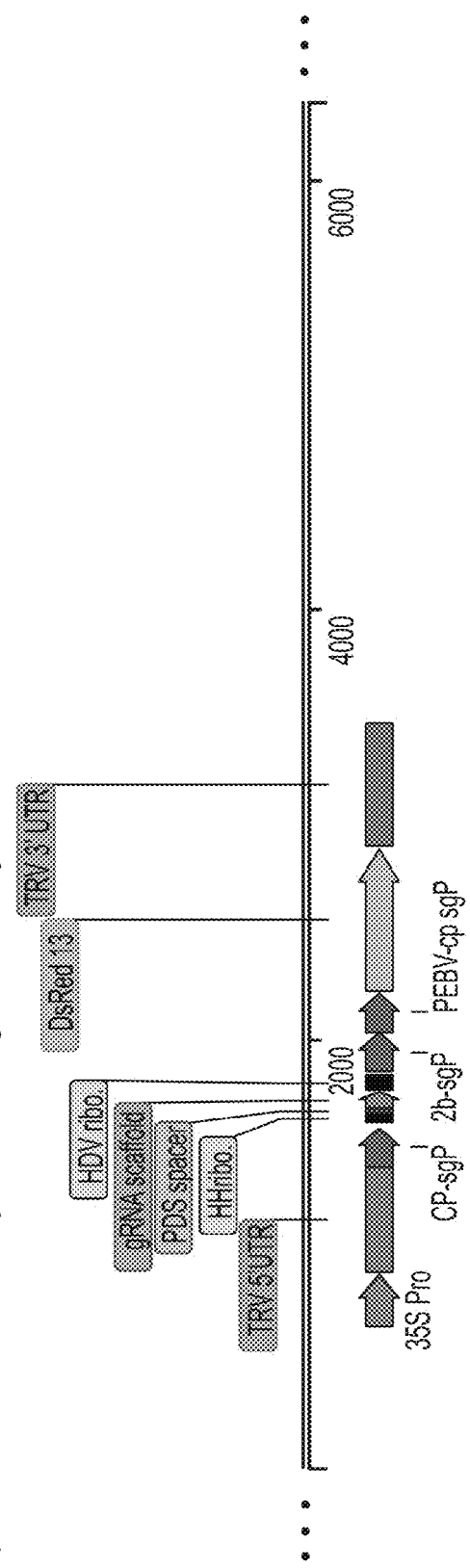
Figures 1F, 2:
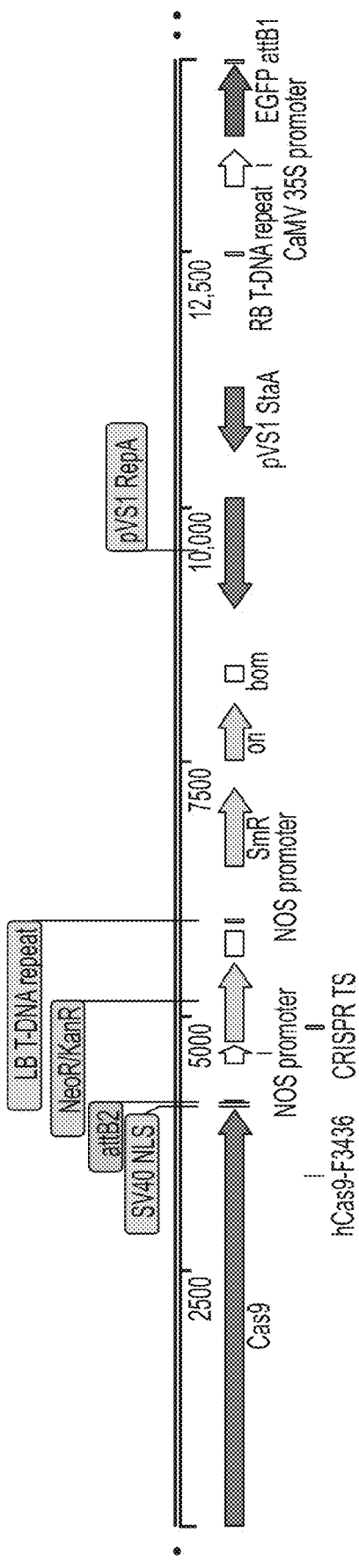

FIGS. 1A-F are maps of the TRV vectors with the guide RNA. FIG. 1A is a map of TRV RNA2-ribozyme—NptII-sgRNA ribozyme:DsRed construct, also shown in SEQ ID NO: 7; FIG. 1B—Map of TRV RNA2-Ribozyme—PDS-sgRNA ribozyme:—DsRed construct, also shown in SEQ ID NO: 8; FIG. 1C—Map of RNA2-CP-sgP—QQR-sgRNA construct (no ribozyme) also shown in SEQ ID NO: 6; FIG. 1D—Map of TRV RNA2 expressing DsRed2 flanked by ribozymes; FIG. 1E—Map of TRV RNA2 expressing both QQR-sgRNA and DsRed, also shown in SEQ ID NO: 18; FIG. 1F—Map of pk7WGF2-hCas9 a binary vector for expression of hCas9;

FIG. 2 shows *N. benthamiana* infected with a vector of TRV DsRed flanked by Ribozymes (FIG. 1D). DsRed was detected in plant parts remote of the infiltration site 6 and 10 days after inoculation (dpi).

Figures 4A, 4B, 4C:
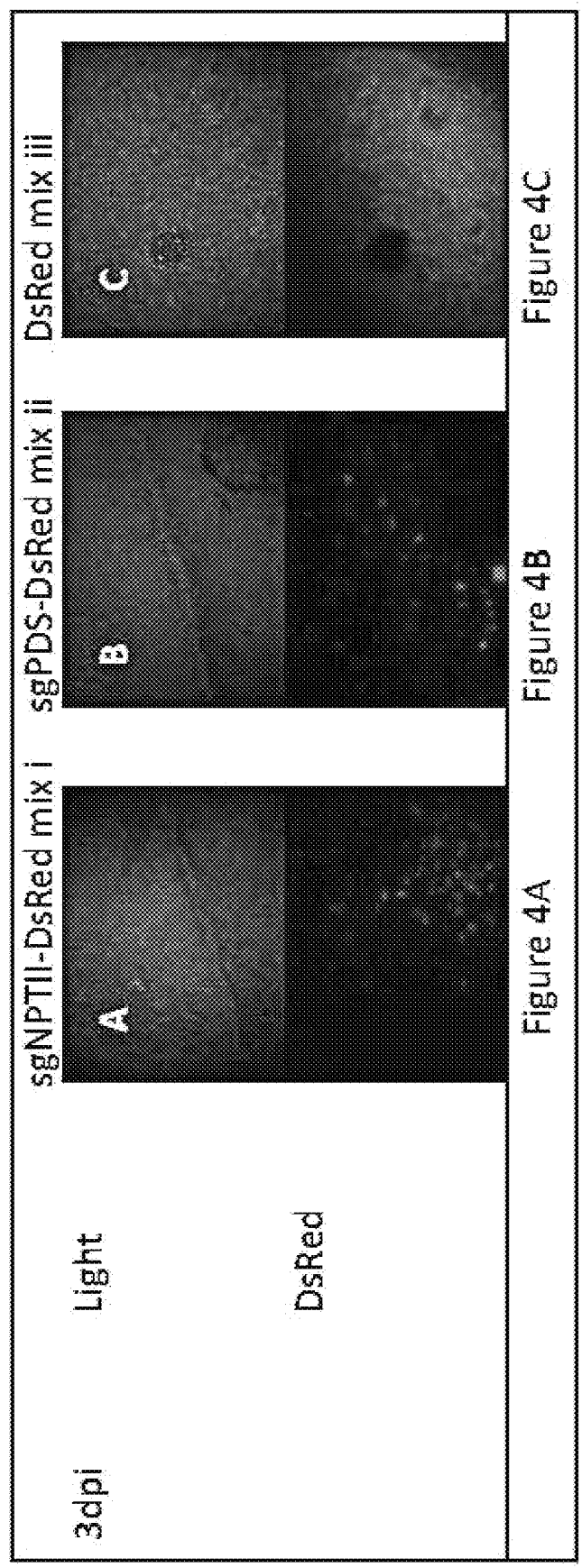

FIGS. 3A-B show indels at the target site detected in the *N. benthamiana* target genes NptII (FIG. 3A) or PDS (FIG. 3B) when inoculated with concomitantly with a binary vector plasmids expressing Cas9 transiently and TRV expressing the appropriate sgRNA (FIGS. 1A-B). In this experiment the sgRNAs were cleaved into their right size due to the presence of flanking Ribozymes. Enrichment for target (by digesting the genomic DNA of the treated tissue with restriction enzyme recognizing a target at the sgRNA site) was performed in FIG. 3A and not in 3B. FIG. 3A—*N. benthamiana* inoculated with mix i (Table 2, below). FIG. 3B—*N. benthamiana* inoculated with mix ii (Table 2, below);

FIGS. 4A-C shows detection of DsRed in inoculated leaves 3 dpi.

FIG. 5 shows GUS activation. GUS activation is visible in double transgenic plants that carry both the Cas9 and a gene in which GUS has been silenced by inserting a stop codon in frame with the ATG codon of the GUS coding sequence. The GUS reporter was reactivated when these plants were infected with construct 1c (FIGS. 1A-F, Table 1);

FIG. 6 shows DNA Sequences of a fragment of the mGUS gene, targeted by the pTRV2*QQR-sgRNA (#3325, SEQ ID NO: 6).

FIGS. 7A-B are images showing *N. benthamiana* and *Petunia*, respectively systemically expressing both DsRed and—QQR-sgRNA from pTRV2 ΔCP (the construct drawing 1E #3337, SEQ ID NO: 18).

FIG. 8 is a schematic presentation vectors aimed at analyzing the contribution of ribozyme flanking the gRNA to the efficiency of genome editing.

FIG. 9 shows DsRed2 signal detected 7 days post inoculation with viral vectors with (1A of FIG. 8) or without (2A of FIG. 8) ribozymes. DsRed2—Red fluorescence, BF—Bright field FIG. 10 is an image showing gene editing using various sgRNA expressing viral vectors. Arrow indicates the 525 bp restriction resistant nptII gene PCR product.

FIG. 11 shows individually edited sequences taken from treatment 1 library (upper image, Mix 1) and from treatment 2 library (lower image, Mix 2). Indels are highlighted in red boxes.

FIG. 12 is a schematic presentation of multiplexing vectors and their control vectors (as in Tables 3-4 below).

FIG. 13 is an image showing multiplexing using dual sgRNA expressing viral vectors (as in Tables 3-4 below).

FIG. 14 shows the precise deletion of DNA fragment using virally-delivered dual sgRNA sequences. Comparison between the non mutated nptII sequence segment (upper sequence) to the mutated nptII sequence segment (lower sequence). CRISPR/Cas9 target sites are highlighted in Yellow. PAM's are highlighted in green.

FIG. 15 shows deletions of DNA fragments using virally-delivered dual sgRNA sequences. Six representative sequences from the *E. coli* library created using the mutated nptII PCR product. 2 out of 6 sequences show the precise 126 bp deletion that represents the majority of the events, as expected according to the CRISPR/Cas9 DNA cleavage machinery. Other sequences shown are larger than 126 bp deletions that were also detected in the library. Due to software limitations and deletion size, only the beginning and the end of the deleted sequence compare to non mutated nptII are presented.

Figure 16:
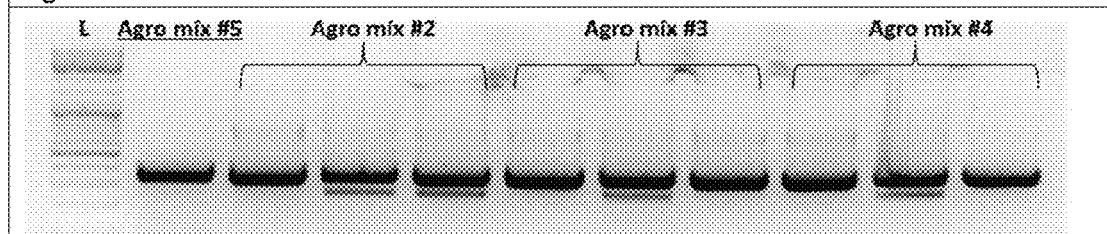

FIG. 16 is an image showing multiplexing using dual sgRNA and DsRed2 expressing viral vectors.

Figure 17:
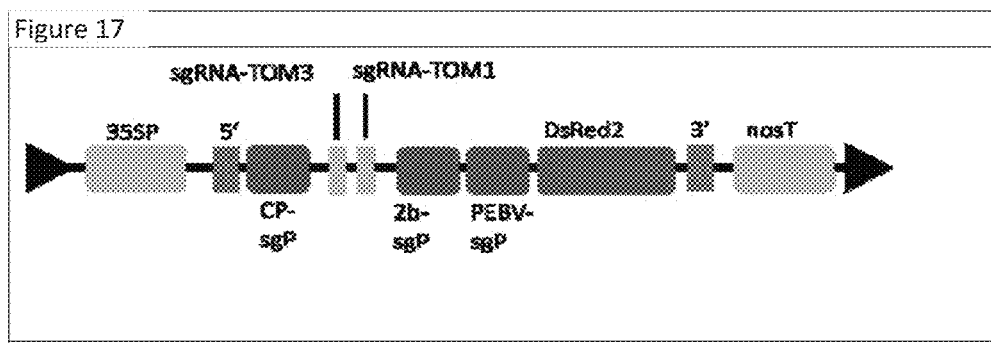

FIG. 17 is a scheme showing a TRV vector map with two guide RNA for the endogenous TOM1 and TOM3 (SEQ ID 80, 81) *petunia* genes.

Figure 18:
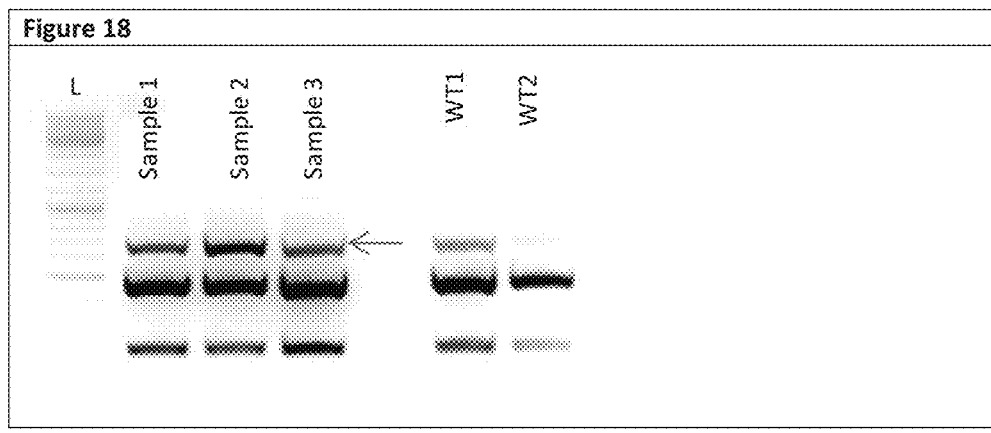

FIG. 18 is an image showing TOM1 target site modification using Multiplex dual sgRNA expressing viral vector.

Figure 19:
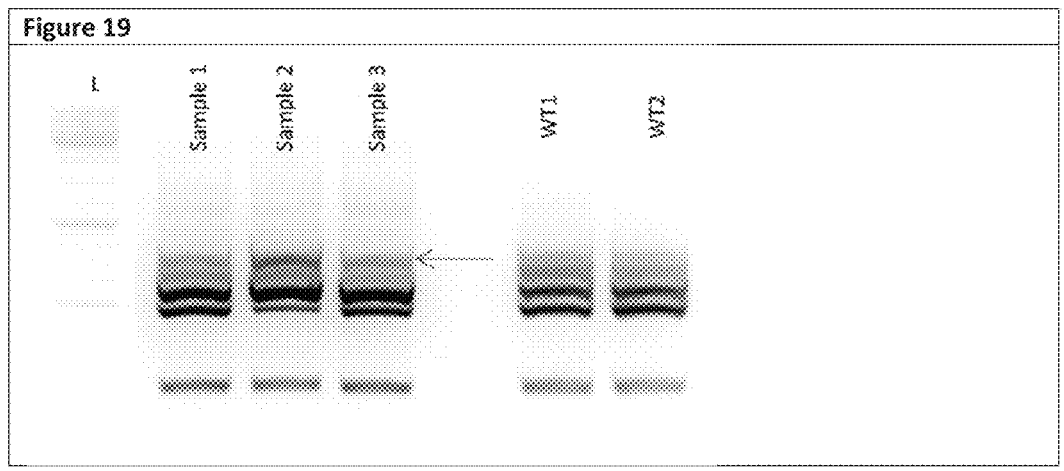

FIG. 19 is as image showing TOM3 target site modification using Multiplex dual sgRNA expressing viral vector.

FIG. 20 shows TOM1 mutated target site using Multiplex dual sgRNA expressing viral vector.

FIG. 21 shows TOM3 mutated target site using Multiplex dual sgRNA expressing viral vector.

FIG. 22: is a mMap of RNA2-ΔCP-sgQQR-DsRed2 construct.

FIG. 23 shows efficient editing of the mGUS target site in Cas9/mGUS transgenic tobacco leaf.

FIG. 24 shows efficient editing of the mGUS target site in Cas9/mGUS transgenic tobacco calli.

FIG. 25 shows the sequencing results of mGUS edited sequences extracted from Tobacco calli from FIG. 24. A partial sequence of the mGUS gene is given. sgQQR target site is highlighted in Yellow, PAM is highlighted in green. Mutated sequences are called del1 and del2, and possess 4 bp and 11 bp deletions, respectively.

FIG. 26 shows chimeric GUS staining in leaf of 3G plant.

FIG. 27 shows a sequencing result comparison of the modified mGUS alleles between the mother plants (T0) and their progeny (T1). ATG codon is underlined in green, TGA codon is underlined in red. WT is the original mGUS sequence present in the transgenic Tobacco plants. Indels are marked with red boxes.

DESCRIPTION OF SPECIFIC EMBODIMENTS OF THE INVENTION

The present invention, in some embodiments thereof, relates to nucleic acid constructs for genome editing and more specifically to tobacco rattle virus (TRV) based nucleic acid constructs which express elements of a oligonucleotide-enzyme conjugate for targeted genome alternations, e.g., the CRISPR/Cas9 system.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The ability to precisely modify genome sequence and regulate gene expression patterns in a site-specific manner holds much promise in plant biotechnology.

Whilst reducing the present invention to practice, the present inventors have introduced a sgRNA/nuclease complex using a TRV-based system into tobacco plants and *petunia* and proved the successful insertion and deletion of nucleotides in a sequence specific manner in a target gene of interest. The present inventors were able to show that the modification can be on an endogenous or an exogenous target sequence, more than one gene can be targeted while using a single TRV vector which contains a plurality of sgRNAs in multiplex manner and moreover the variation is stable for at least 2 generations.

The TRV promoter was found to mediate transcription of the sgRNA in an efficient manner. The phenotype was observed already in viral infected cells/plants rendering selection of plants more efficient and suggests that the use of transient expression systems as efficient in conferring genomic variation.

The present modification tool is thus a next-generation genome-editing platform, which can be used in the production of designer plants to address the needs of agriculture, horticulture and basic plant biology.

Thus, according to an aspect of the invention there is provided a nucleic acid construct comprising a tobacco rattle virus (TRV) sequence and a nucleic acid sequence encoding a single guide RNA (sgRNA) that mediates sequence-specific cleavage in a target sequence of a genome of interest, wherein said TRV sequence is devoid of a functional 2b sequence.

As used herein "a nucleic acid construct", or a "vector" refers to a DNA or RNA vector.

As used herein a "tobacco rattle virus" or "TRV" or "pTRV" refers to a vector or vectors that comprise TRV nucleic acids.

TRV is a positive strand RNA virus with a bipartite genome, meaning that the genome is divided into two positive-sense, single-stranded RNAs, that may be separately encapsidated into viral particles. The two TRV genomic RNAs are referred to as TRV-RNA1 (TRV1 or pTRV1) and TRV-RNA2 (TRV2 or pTRV2). RNA1 encodes polypeptides that mediate replication and movement in the host plant, while RNA2 encodes coat protein and elements related to the nematode transfer of the virus between plants, including 2b (SEQ ID NO: 27).

A TRV-RNA1 replicon typically comprises a replication start site, one or more TRV replicases, such as 134 kDa and 194 kDa replicases, a movement protein, and a cysteine-rich protein, such as a TRV 16 kDa cysteine-rich protein.

A TRV-RNA2 replicon comprises a replication start site, a viral coat protein, such as a TRV viral coat protein and a heterologous sequence. The pTRV coat protein typically functions to for transmission from plant to plant. The 2b is one of the elements related to the nematode transfer of the virus between plants.

As discussed hereinbelow, non-essential structural genes may be replaced by a heterologous nucleic acid sequence such as for providing multiple cloning site for gene expression and/or encoding an expression product(s) of interest.

According to another specific embodiment, the pTRV2 is devoid of a functional coat protein, thus allowing the TRV2 to function as a satellite vector.

Alternatively or additionally, the nucleic acid sequence of TRV (e.g., pTRV2) is devoid of a functional 2b sequence (e.g., SEQ ID NO: 27). According to a specific embodiment, the 2b sequence is deleted such that it does not contain an ATG that may lead incorrect open reading frame translation. Thus the sequence includes less than 300 bp or 200 bp sequences of the 2b sequence or even a complete deletion of the 2b sequence. The deletion of the 2b sequence functions to provide efficient expression in meristematic tissues and expression of long nucleic acid sequences/polypeptide products thereof e.g., above at least 2 kb bases or 633 amino acids.

Thus, according to a specific embodiment, the nucleic acid construct comprises a TRV cDNA which includes at least one cis acting element permitting transcription of said cDNA; for example a promoter (e.g., subgenomic promoter, e.g., SEQ ID NO: 23) operably linked to a sequence encoding a heterologous nucleotide sequence which is foreign to said virus, in this case, the sgRNA.

As used herein a "heterologous nucleotide sequence" is a sequence that is not a naturally occurring part of a naturally occurring TRV and/or is not in a native orientation on the native TRV genome.

The deleted ORFs may be replaced by a heterologous nucleotide sequence (e.g., sgRNA) upstream to the untranslated region (UTR).

In certain embodiments, the vector is a DNA vector. Accordingly it comprises a plant active promoter situated so as to stimulate transcription of (operably linked to) a TRV-RNA1 or TRV-RNA2 replicon. For example, a plant active promoter may be situated at the 5'-end of a TRV-RNA1 or TRV-RNA2 replicon.

The term "plant active promoter" refers to a promoter that functions in a host plant that is infected/transformed with the TRV vector or with other plant expressible vectors.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
| --- | --- | --- |
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An, et al, Plant J. 10(1); 107-121, 1996 |

TABLE II

Exemplary seed-preferred promoters for use in the performance of some embodiments of the invention

| Gene Source | Expression Pattern | Reference |
| --- | --- | --- |
| Seed specific genes | seed | Simon, et al., Plant Mol. Biol. 5. 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al., Plant Mol Biol, 143). 323-32 1990 |
| napA | seed | Stalberg, et al., Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albani et al., Plant Cell, 9: 171-184, 1997 |
| wheat a, b and g gliadins | endosperm | EMBO3: 1409-15, 1984 |
| Barley ltr1 promoter barley B1, C, D hordein | endosperm endosperm | Theor Appl Gen 98: 1253-62, 1999; Plant J 4: 343-55, 1993; Mol Gen Genet 250: 750-60, 1996 |
| Barley DOF | endosperm | Mena, et al., The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu, et al., Plant Cell Physiology 39(8) 885-889, 1998 |
| rice -globulin Glb-1 | endosperm | Wu, et al., Plant Cell Physiology 398) 885-889, 1998 |

TABLE II-continued

Exemplary seed-preferred promoters for use in the performance of some embodiments of the invention

| Gene Source | Expression Pattern | Reference |
|---|---|---|
| rice OSH1 | emryo | Sato, et al., Proc. Nati. Acad. Sci. USA, 93: 8117-8122 |
| rice alpha-globulin REB/OHP-1 | endosperm | Nakase, et al., Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorghum gamma-kafirin | endosperm | PMB 32: 1029-35, 1996 |
| KNOX | emryo | Postma-Haarsma, et al., Plant Mol. Biol. 39: 257-71, 1999 |
| rice oleosin | Embryo and aleuton | Wu, et al, J. Biochem., 123: 386, 1998 |
| sunflower oleosin | Seed (embryo and dry seed) | Cummins, et al., Plant Mol. Biol. 19: 873-876, 1992 |

TABLE III

Exemplary flower-specific promoters for use in the performance of the invention

| Gene Source | Expression Pattern | Reference |
|---|---|---|
| AtPRP4 | flowers | salus(dot) medium(dot)edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala- 3 | flowers | |

TABLE IV

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl- CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |

TABLE IV-continued

Alternative rice promoters for use in the performance of the invention

| PRO # | gene | expression |
|---|---|---|
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha- globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PRO0228 | BLZ-2_long (barley) | |

In certain embodiments, a TRV-RNA1 or TRV-RNA2 is operably linked to two or more plant active promoters. In certain embodiments, it may be desirable to include an additional plant active promoter or promoters to drive additional expression of the heterologous nucleic acid(s). Thus for example, each sgRNA is operably linked to a plant promoter, likewise the nuclease is also operably linked to a plant promoter.

In certain embodiments, the heterologous nucleic acid sequence (e.g., encoding sgRNA) is expressed from a subgenomic RNA, transcription of which is stimulated by an endogenous TRV subgenomic promoter. An exemplary sequence of a subgenomic promoter is provided in SEQ ID NO: 23.

In certain embodiments, a transcriptional terminator may be positioned at the 3'-end of an RNA transcript to limit readthrough of the transcript. For example, a transcriptional terminator may be positioned at the 3'-end of a TRV-RNA1 or TRV-RNA2 replicon. A commonly used plant transcriptional terminator is a nopaline synthase terminator (NOSt, SEQ ID NO: 24).

In certain embodiments, modification to pTRV1 or pTRV2 vector comprises addition of an enhancer. Any enhancer can be inserted into the viral expression vector to enhance transcription levels of genes. For example, an OMEGA enhancer (SEQ ID NO: 25) can be cloned into the pTRV1 or pTRV2 vectors of the present invention.

Any TRV based vector is included under the embodiments of the invention.

According to a specific embodiment, the two TRV genomic RNA vectors used by the present invention are referred to herein as pTRV1 (GeneBank Accession No: AF406990) and pTRV2 (GeneBank Accession No: AF406991), wherein pTRV1 encodes polypeptides that mediate replication and movement in the host plant while pTRV2 encodes coat proteins.

Alternatively, the viral vector of the present invention may be based on TRV related viruses (e.g. tobacco rattle virus strain N5, HMV, or tobacco rattle virus strain TCM).

Examples of other TRV-RNA1 and RNA2 vectors may be found, for example, in Ratcliff, F. Martin-Hernandez, A. M. and Baulcombe, D. C. (2001) Tobacco rattle virus as a vector for analysis of gene function by silencing. Plant J. 25, 237-245. and Hernandez et al., 1997; Ratcliffe et al. U.S. Pat. No. 6,369,296; Dinesh et al. U.S. Patent Appl. No. 20030182684 as well as in U.S. Pat. No. 8,791,324.

As used herein "a single guide RNA" or "sgRNA" refers to a chimeric RNA molecule which is composed of a CRISPR RNA (crRNA) and trans-encoded CRISPR RNA (tracrRNA). The crRNA defines a site-specific targeting of the Cas9 protein. The sequence is 19-22 nucleotides long e.g., 20 consecutive nucleotides complementary to the target and is typically located at the 5' end of the sgRNA molecule. The crRNA may have 100% complementation with the target sequence although at least 80%, 85%, 90%, and 95% global homology to the target sequence are also contemplated according to the present teachings.

The tracrRNA is 100-300 nucleotides long and provides a binding site for the nuclease e.g., Cas9 protein forming the CRISPR/Cas9 complex.

According to a specific embodiment the target sequence is endogenous to the genome of interest. That is it is present at the same copy number and genomic location in the genome as that of the wild type genome.

According to a specific embodiment, the target sequence is exogenous to the genome of interest. Also referred to herein as heterologous. In such a case, it may be a gene that is present in the genome but in a different location or it may be a completely foreign gene, i.e., absent from the genome comprising the target sequence.

According to a specific embodiment a plurality of gRNAs are provided to the plant cell that are complementary to different target nucleic acid sequences and the nuclease e.g., Cas9 enzyme cleaves the different target nucleic acid sequences in a site specific manner. The plurality of gRNBAs may be encoded from a single or a plurality of TRV vectors as described herein. The use of a plurality of sgRNAs allows multiplexing.

According to a specific embodiment, a plurality of sgRNAs to a single target gene (e.g., vector B2) or a plurality of target genes (e.g., FIG. 17) are present in the construct. Such a plurality (e.g., more than 1, more than 2, more than 3, more than 4, more than 5, e.g., 2-5, 2-4, 2-3) of sgRNAs are positioned under a single promoter. The sgRNAs may be or may not be separated from each other by a spacer.

It will be appreciated that such a multiplex configuration i.e., under a single subgenomic promoter can be applied in any genome editing method which employs the CRISPR/Cas9 system. Accordingly, there is provided a nucleic acid construct comprising at least 2 sgRNAs under a single promoter.

Such nucleic acid constructs can be for any cell be it prokaryotic or eukaryotic, e.g., mammalian (e.g., human), plant, insect and yeast.

According to a specific embodiment, the nucleic acid sequence encoding the sgRNA is flanked by ribozyme sequences to generate a ribozyme-sgRNA-ribozyme (RGR) sequence (e.g., SEQ ID NOs: 21 and 22). It is suggested that primary transcripts of RGR undergo self-catalyzed cleavage to release the sgRNA. It is also contemplated, that the RGR configuration broadens the scope of promoters which can be used for the sgRNA transcription, although it has been found herein that the use of TRV subgenomic promoter allows for an efficient transcription of the sgRNA even without the flanking ribozymes. The RGR strategy guarantees that if the whole viral replicon is fully transcribed, any expression product of interest (e.g., reporter, agriculturally valuable trait e.g., stress resistance etc.) is expressed in the inoculated tissue, and guide RNA is also created in the same tissue.

Thus in the RGR configuration, the sgRNA is fused on the 5' to a first ribozyme sequence and on the 3' to a second ribozyme sequence. Each of these ribozyme sequences is a self-cleaving ribozyme.

According to a specific embodiment, the ribozyme is a hammerhead ribozyme.

Methods of designing ribozyme sequences are well known in the art and are also taught in Lincoln T A, Joyce G F (February 2009). "Self-sustained replication of an RNA enzyme". Science 323 (5918): 1229-1232.

According to a specific embodiment, the first and second ribozyme sequences are non-identical.

According to a specific embodiment, the first and second ribozyme sequences are identical.

Specific examples of hammerhead ribozymes are provided in SEQ ID NOs: 4 and 5. Specific examples of RGR sequences are provided in SEQ ID NOs: 21 and 22.

As mentioned, the TRV sequence (e.g., TRV2) encodes at least one single guide RNA (e.g., 2, 3 or more).

Thus, according to a specific embodiment, the sgRNA comprises at least two sgRNAs targeting a plurality of target sequences in the plant genome. The plurality of sgRNAs can be transcribed from a single TRV replicon or from a plurality of TRV constructs. According to a specific embodiment, each of these sgRNAs is under the regulation of a plant promoter e.g., subgenomic promoter of TRV.

In order to mediate cleavage, the nucleic acid construct may further comprise a nucleic acid sequence encoding the nuclease e.g., Cas9 or RISC.

As used herein "a nuclease" refers to an enzyme that binds the sgRNA to cleave genomic DNA in a sequence specific manner, specificity which is conferred by the crRNA.

Examples of such enzymes are Cas9 and RISC.

Alternatively or additionally, the Cas9 may be encoded from another nucleic acid construct and thus the CRISPR-Cas9 complex is encoded from a nucleic acid construct system.

According to a specific embodiment, the Cas9 is as set forth in SEQ ID NO: 9 or 10 although sequences modification may be applied to improve plant expression e.g., SEQ ID NOs: 9 and 10 and at least 60%, 65%, 70%, 75%, 80%, 85%, 90%, 95%. Homology and identity are also contemplated herein (e.g., using Blast(N)/(P) with default parameters).

Cas9 is a monomeric DNA nuclease guided to a DNA target sequence adjacent to the protospacer adjacent motif (PAM). The Cas9 protein comprises two nuclease domais homolgouys to RuvC and HNH nucleases. The HNH nuclease domain cleaves the complementary DNA strand whereas the RuvC-like domain cleaves the non-complementary strand and, as a result, a blunt cut is introduced in the target DNA.

RISC enzymes are taught in Martinez J, Tuschl T. RISC is a 5' phosphomonoester-producing RNA endonuclease. Genes Dev. 2004; 18:975-980. Also contemplated are sequence modifications to improve plant expression i.e., homologs that are at least 60%, 65%, 70%, 75%, 80%, 85%, 90%, 95%. Homology and identity are also contemplated herein (e.g., using Blast(N)/(P) with default parameters).

Thus, the present teachings refer to naturally occurring as well as synthetic and codon optimized versions of the nuclease e.g., RISC and Cas9.

Nucleic acid sequences of the polypeptides of some embodiments of the invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot)or(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

In order to ensure nuclear localization, the nuclease coding sequence may be translationally fused to a nuclear localization domain which may be endogenous or heterologous to the naturally occurring Cas9 sequence. According to a specific embodiment, the NLS is of SV40.

Since the present teachings relate to plant genome modifications, the nuclease e.g., Cas9 or RISC may also be directed to other genome containing organelles such as the mitochondria and the chloroplast, using a mitochondria localization signal, or chloroplast modification signal, respectively.

Any of a plurality of coding sequences on a given vector may be transcribed via a promoter such as a subgenomic promoter (sgP, SEQ ID NO: 23).

Thus, according to a specific embodiment, transcription of said sgRNA and said nuclease is regulated by two separate sub genomic promoters (sgPs).

Alternatively, the Cas9 is encoded by a different vector, such as a pTRV-based vector as taught in WO2009/130695, T-DNA binary vector e.g., pGREEN, pBIN19, pK7WGF2 and pPVP or via another viral based vector such as a Geminivirus-based vector e.g., those taught in WO2007/141790 and WO2010/004561.

As mentioned, the TRV nucleic acid sequence and the coding sequence for the nuclease (e.g., Cas9 or RISC) is part of a vector. Generally, a vector is a nucleic acid construct that is designed to facilitate propagation and introduction into a host cell. In certain embodiments, the vector is a DNA vector designed for use with *Agrobacterium*-mediated transformation and contains T DNA sequences flanking the TRV1, TRV2 and/or nuclease replicon. The flanking T DNA sequences mediate insertion of the replicon into the genome of a host plant cell. Vectors for use with *Agrobacterium* are referred to as binary transformation vectors, and many are known in the art, such as pGreen, PBIN19, pK7WGF2 or pCASS2. In certain embodiments, a vector is designed to be maintained in *E. coli*, and such a vector will generally include an *E. coli* origin of replication and a selectable marker, such as an antibiotic resistance gene. In certain embodiments, a vector may include a plant selectable marker. A vector may also be designed, for example, for introduction by particle bombardment, e.g. by using a gun equipped to deliver tungsten microparticles coated with vector or by exposing cells to silicon whiskers. See, e.g. Taylor and Fauquet, 2002, DNA and Cell Biology 21:963-77. In the case of such delivery systems, the vector may be RNA or DNA and need not contain any specific sequences to facilitate transfer to a plant chromosome. Other methods of introduction of nucleic acid sequences into plant cells are described hereinbelow.

In certain embodiments, the invention provides cells comprising the construct or nucleic acid construct system of the invention. A cell may be a bacterial cell, such as an *E. coli* cell or an *Agrobacterium tumefaciens* cell.

A cell comprising the construct or nucleic acid construct system of the invention may also be a plant cell. In certain embodiments, the invention provides a plant cell comprising both a TRV-RNA1 vector and a TRV-RNA2 vector. In many instances, a vector is not itself retained in a cell, but the replicon portion is retained, and accordingly in certain embodiments, the invention provides a plant cell comprising a TRV-RNA1 replicon and a TRV-RNA2 replicon. Alternatively or additionally, the plant cell comprises the genetic modification which is resultant of the activity of the CRISPR/nuclease activity without any remnants of the TRV replicon or the construct. Alternatively or additionally, the cell comprises the replicon or construct encoding the nuclease.

Plant cells of the invention may be in culture, as in the case of cell suspensions or cells in the process of forming callus, e.g., tissue culture. Plant cells may also be situated in a living or dead plant or in a plant product.

In a further embodiment, the present invention provides a virus or viral particle including, preferably encapsulating, a TRV-RNA1 and/or TRV-RNA2 replicon of the invention.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

According to a specific embodiment, the plant is a dicotyledonous plant.

According to a specific embodiment, the plant is a crop plant.

According to a specific embodiment, the plant is of a horticultural value.

According to some embodiments of the invention, the plant comprises a *Petunia hybrida*.

According to some embodiments of the invention, the plant comprises a *Nicotiana tabacum*.

According to some embodiments of the invention, the plant in selected from the group consisting of an *Arabidopsis thaliana*, an *Artemisia* sp., a *Artemisia annua*, a *Beta vulgaris*, a *Solanum tuberosum*, a *Solanum pimpinellifolium*, a *Solanum lycopersicum*, a *Solanum melongena*, a *Spinacia oleracea*, a *Pisum sativum*, a *Capsicum annuum*, a *Cucumis sativus*, a *Nicotiana benthamiana*, a *Nicotiana tabacum*, a

*Zea mays*, a *Brassica napus*, a *Gossypium hirsutum* cv. Siv'on, a *Oryza sativa* and a *Oryza glaberrima*.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant.

Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050 and 5,693,507, which are incorporated herein by reference. A polypeptide can thus be produced by the protein expression system of the chloroplast and become integrated into the chloroplast's inner membrane.

Using the present constructs it is possible to generate a variation in a plant genome of any DNA containing organelle.

Interestingly, the present inventors have identified that such genetic variability is inherited (following crossing) and thus is stable for at least 2 generations.

As used herein the phrase "genotypic variation" refers to a process in which a nucleotide or a nucleotide sequence (at least 2 nucleotides) is selectively altered or mutated at a predetermined genomic site, also termed as mutagenesis. The genomic site may be coding or non-coding (e.g., promoter, terminator, splice site, polyA) genomic site. This alteration can be a result of a deletion of nucleic acid(s), a randomized insertion of nucleic acid(s), introduction of a heterologous nucleic acid carrying a desired sequence, or homologous recombination following formation of a DNA double-stranded break (DSB) in the target gene. Genotypic variation according to the present teachings may be transient or stable. Genotypic variation in accordance with the present teachings is typically effected by the formation of DSBs, though the present invention also contemplates variation of a single strand. Genotypic variation may be associated with phenotypic variation. The sequence specific or site directed nature of the present teachings thus may be used to specifically design phenotypic variation.

It will be appreciated that two plant expression vectors may be introduced into the same plant cell. These plant expression vectors may be introduced in the plant cell concomitantly or at separate times. Such expression vectors may comprise nucleic acid sequences encoding different heterologous sequences. For example, an expression vector comprising a nucleic acid sequence encoding the sgRNA (pTRV2) a pTRV1 and a nucleic acid vector encoding Nuclease (e.g., Cas9 or RISC). The three expression vectors can be introduced concomitantly, as for example at a 1:1:1 ratio, to enable expression of heterologous genes in plant cells.

The following section provides non-limiting applications for generating such a variation.

Thus, the CRISPR/Nuclease (e.g., Cas9 or RISC) complexes of some embodiments of the present invention may be used to generate a signature of randomly inserted nucleic acids in a sequence-specific manner, also referred to herein as tagging. This signature may be used as a "genetic mark". This term is used herein distinctively from the common term "genetic marker". While the latter term refers to naturally occurring genetic variations among individuals in a population, the term genetic mark as used herein specifically refers to artificial (man generated), detectable genetic variability, which may be inherited.

The DSB is typically directed into non-coding regions (non open reading frame sequence) so as not to affect the plant's phenotype (e.g. for tagging). However, tagging can also be directed to a coding region. A high quality genetic mark is selected unique to the genome of the plant and endures sequence variation which may be introduced along the generations.

For some, e.g., regulatory, purposes it may be desired to mark commercially distributed plants with publicly known marks, so as to enable regulatory authorities to readily identify the mark, so as to identify the manufacturer, distributor, owner or user of the marked organism. For other purposes secrecy may be advantageous. The latter is true, for example, for preventing an attempt to genetically modify the genetic mark of a supreme event protected by intellectual property laws.

An intellectual property protected organism which is also subject to regulation will therefore be, according to a useful embodiment of the present invention, genetically marked by (a) at least one unique DNA sequence which is known in public; and (b) at least one unique DNA sequence that is unknown, at least not as a genetic mark, in public.

To introduce a heterologous sequence (e.g., coding or non-coding), DSBs will first be generated in plant DNA as described herein. It is well known those of skill in the art that integration of foreign DNA occurs with high frequency in these DNA brake sites [Salomon et al., EMBO J (1998) 17: 6086-6095; Tzfira et al., Plant Physiol (2003) 133: 1011-1023; Tzfira et al., Trends Genet (2004) 20: 375-383, Cal et al. (2009) Plant Mol Biol. Accepted: 14 Dec. 2008]. Once present in the target cell, for example on episomal plasmids, foreign DNA may be cut out from the plasmid using the CRISPR/Nuclease (e.g., Cas9 or RISC) complex to generate DSBs in the plant DNA. The foreign DNA released from the episomal plasmid will then be incorporated into the cell DNA by plant non-homologous end joining (NHEJ) proteins. The DSBs may also lead to enhanced homologous recombination (HR)-based gene targeting in plant cells (Puchta et al. Proc Natl Acad Sci USA (1996) 93: 5055-5060).

As mentioned, the present teachings can be used to generate genotypic variation. Thus, the CRISPR/Nuclease (e.g., Cas9 or RISC) complexes can be designed to generate DSBs in coding or non-coding regions of a locus of interest so as to introduce a heterologous gene of interest. Such alterations in the plant genome may consequently lead to additions or alterations in plant gene expression (described in detail hereinabove) and in plant phenotypic characteristics (e.g. color, scent etc.).

Additionally CRISPR/Nuclease (e.g., Cas9 or RISC) complexes can be used to generate genotypic variation by knocking out gene expression. Thus CRISPR/Nuclease (e.g., Cas9 or RISC) complexes can be designed to generate DSBs in coding or non-coding regions of a locus of interest so as to generate a non-sense or mis-sense mutation. Alternatively, two pairs of CRISPR/Nuclease (e.g., Cas9 or RISC) complexes (e.g. or combinations of same) can be used to cleave out an entire sequence of the genome, thereby knocking out gene expression.

CRISPR/Nuclease (e.g., Cas9 or RISC) complexes of the present invention may also be used to generate genotypic variations in gametes and seeds of the plant. Thus, the CRISPR/Nuclease (e.g., Cas9 or RISC) complexes of the present invention may be used to generate specific or non-specific mutations in gametes which, following fertilization, will generate genotypically modified seeds and consequently modified plants.

CRISPR/Nuclease (e.g., Cas9 or RISC) complexes of the present invention may also be used to generate genotypic variations in calli of the plant. Thus, the CRISPR/Nuclease (e.g., Cas9 or RISC) complexes of the present invention may be used to generate specific or non-specific mutations in embryogenic calli cells, including in immature embryo scutella and mature embryo scutella cells, in cells of a first node driven calli, in split seedling nodes, in split seeds, in inner leaf sheathes of seedlings and in zygotes of fertilized embryo sacs.

It will be appreciated that plant calli of the invention can differentiate into a whole plant (e.g. regenerate) thereby generating plants comprising the genotypic variation.

The nucleotide (sgRNA)/Nuclease (e.g., CRISPR/Cas9 or RISC) complexes of the present invention may also be used to generate variability by introducing non-specific mutations into the plant's genome.

Additionally, the sgRNA (e.g., CRISPR/Cas9 or RISC) complexes of the present invention may be used to combat infections by plant pathogens.

Thus the present invention envisages a method of treating a plant infection by a pathogen. The method comprising generating a pathogen resistant plant, the method comprising introducing into the plant the expression vector of some embodiments of the invention, wherein the nucleic acid binding domain of the sgRNA/Nuclease (e.g., CRISPR/Cas9 or RISC) complexes mediates specific targeting of the nuclease to a gene conferring sensitivity to a pathogen, thereby generating the pathogen resistant plant.

As used herein a "plant pathogen" refers to an organism, which causes a disease in a plant. Organisms that cause infectious disease include fungi, oomycetes, bacteria, viruses, viroids, virus-like organisms, phytoplasmas, protozoa, nematodes and parasitic plants.

It is advisable to generate a plant lacking a gene which is needed for the pathogen's infection of the plant. Thus, according to one embodiment, the gene conferring sensitivity to a pathogen is knocked-out to thereby increase resistance to the pathogen.

The present invention also envisages a method of generating male sterility in a plant. The method comprising upregulating in the plant a structural or functional gene of a mitochondria or chloroplast associated with male sterility by introducing into the plant the plant expression vector of some embodiments of the invention and a nucleic acid expression construct which comprises at least one heterologous nucleic acid sequence which can upregulate said structural or functional gene of a mitochondria or chloroplast when targeted into the genome of the mitochondria or chloroplast, wherein the sgRNA of the sgRNA (e.g., CRISPR/Cas9 or RISC) complex mediates specific targeting to the genome of the mitochondria or chloroplast, thereby generating male sterility in the plant.

Thus for example, the nucleic acid expression construct comprises a coding (e.g., for a CMS associated gene) or non-coding (e.g., powerful promoter for enhancing expression of a CMS associated gene) heterologous nucleic acid sequence as well as a binding site for the sgRNA (e.g., CRISPR/Cas9 or RISC) complexes (identical to that on the mitochondria or chloroplast genome). Upon cleavage by the sgRNA/nuclease (e.g., Cas9 or RISC) complexes, the heterologous nucleic acid sequence is inserted into the predetermined site in the genome of the chloroplast or mitochondria.

As mentioned hereinabove, cytoplasmic male sterility (CMS) is associated with mitochondrial dysfunction. To this effect, the sgRNA/nuclease (e.g., CRISPR/Cas9 or RISC) complexes are designed to comprise a mitochondria localization signal (as described in detail hereinabove) and cleavage sites which are specific for the mitochondrial genome. Specific genes which may be upregulated include, but are not limited to, the *Petunia* pcf chimera that is located with close proximity to nad3 and rps12, the Rice (*Oryza sativa*) sequence which is downstream of B-atp6 gene (i.e. orf79), the Maize T-urf13 and orf221, the *Helianthus* sp. orf239 downstream to atpA, the *Brassica* sp. orfs which are upstream to atp6 (e.g. orf139 orf224 or orf138 and orf158). It will be appreciated that in order to induce CMS, these genomic sequences are typically transcribed in the plant, thus the teachings of the present invention envision targeting these sequences (e.g. by adding coding sequences) or overexpression thereof using the above described methods as to achieve CMS.

It will be appreciated that CMS phenotype, generated by the incompatibility between the nuclear and the mitochondrial genomes, is used as an important agronomical trait which prevents inbreeding and favors hybrid production.

As mentioned hereinabove, induction of CMS can also be achieved by overexpression of a chloroplast gene such as β-ketothiolase. Overexpression of β-ketothiolase via the chloroplast genome has been previously shown to induce CMS [Ruiz et al (2005) Plant Physiol. 138 1232-1246]. Thus, the present teachings also envision targeting chloroplast genes or overexpression thereof (e.g. β-ketothiolase) using the above described methods in order to achieve CMS.

The present invention further envisages a method of generating a herbicide resistant plant. The method comprising introducing into the plant the plant expression vector of some embodiments of the invention, wherein the sgRNA domain of the complex (e.g., CRISPR/Cas9 or RISC) mediates specific targeting to a gene conferring sensitivity to herbicides, thereby generating the herbicide resistant plant.

It will be appreciated that in the field of genetically modified plants, it is well desired to engineer plants which are resistant to herbicides. Furthermore, most of the herbicides target pathways that reside within plastids (e.g. within the chloroplast). Thus to generate herbicide resistant plants, the sgRNA/nuclease (e.g., CRISPR/Cas9 or RISC) complexes are designed to comprise a chloroplast localization signal (as described in detail hereinabove) and cleavage sites which are specific for the chloroplast genome. Specific genes which may be targeted in the chloroplast genome include, but are not limited to, the chloroplast gene psbA (which codes for the photosynthetic quinone-binding membrane protein $Q_B$, the target of the herbicide atrazine) and the gene for EPSP synthase (a nuclear gene, however, its overexpression or accumulation in the chloroplast enables plant resistance to the herbicide glyphosate as it increases the rate of transcription of EPSPs as well as by a reduced turnover of the enzyme).

Alternatively, herbicide resistance may be introduced into a plant by upregulating an expression of a protein (e.g. phosphinothricin acetyltransferase) which imparts resistance to an herbicide when expressed in the plant. Thus, a nucleic acid expression construct comprising a heterologous nucleic acid sequence (e.g. phosphinothricin acetyltransferase) is introduced into the plant for expression of the protein conferring herbicide resistance.

Also provided is a method of generating a plant with increased abiotic stress tolerance, the method comprising introducing into the plant the nucleic acid construct described herein, wherein said (sgRNA) mediates sequence-specific cleavage in a target sequence of a gene of the plant conferring sensitivity to abiotic stress, thereby generating the plant with increased abiotic stress tolerance.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, osmotic stress, water deprivation, drought, flooding, freezing, low or high temperature, heavy metal toxicity, anaerobiosis, nutrient deficiency (e.g., nitrogen deficiency or limited nitrogen), atmospheric pollution or UV irradiation.

The phrase "abiotic stress tolerance" as used herein refers to the ability of a plant to endure an abiotic stress without suffering a substantial alteration in metabolism, growth, productivity and/or viability.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1 pTRV2 Vectors Expressing gRNA are Capable of Efficiently Targeting Endogenous and Exogenous Genes Materials and Methods
Vectors Construction
Cloning of sgRNA into pTRV2 Vector The cloning of sgRNAs as a ribozyme-RNA-ribozyme cassette was done following the paper of Yangbin Gao and Yunde Zhao. "Self-processing of ribozyme-flanked RNAs into guide RNAs in vitro and in vivo for CRISPR-mediated genome editing". J. Integr. Plant Biol. 2014 April; 56(4): 343-9.

The RNA molecule was designed to contain a Hammerhead type ribozyme (Pley et al. 1994 (SEQ ID NO:4)) at the 5'-end, a guide RNA that targets a nptII (SEQ ID NO: 1) or PDS (SEQ ID NO: 2) genes in the middle, and a hepatitis delta virus (HDV) ribozyme (Ferre-D'Amare et al. 1998 (SEQ ID NO:5)). The ribozyme-RNA-ribozyme cassettes were ordered as linear DNA with HindIII and BglII sites at 5' and 3' ends, respectively. Cloning of the cassette into pTRV2 Δ2b:[2sgPromoter-DsRed] was effected using these restriction enzymes. The digestion by these enzymes removed the TRV coat protein (CP) gene from the viral vector construct and set the ribozyme-RNA-ribozyme instead (SEQ ID NOs: 21 and 22).

The QQR-sgRNA (QQR=24nt sequence (ttcttccctcc tgaggggaagaa, SEQ ID NO: 26) with a stop codon that was inserted into the GUS gene downstream to the ATG codon. cassette was cloned into pTRV2—Δ2b to a HindIII site at the 5' of the CP gene. Then the CP gene of TRV was completely removed by digesting with BglII and religating the plasmid without the CP gene (SEQ ID NO:6), see FIGS. 1A-F.

The TRV vector was improved to express only the sgRNA:pTRV2 ΔCP-Δ2b with the QQR-sgRNA by the addition of a reporter gene that enabled following the systemic infection of the plant by the TRV expressing both the sgRNA and the reporter concomitant and fluorescent protein. The cloning was done by inserting a PCR amplicon containing: two sub-genomic promoters (viral promoters name: TRV 2b-Pro and PEBV cp-Pro) and a DsRed2 gene (SEQ ID NO: 18). This amplicon was ligated into the sequence of pTRV2 ΔCP-Δ2b with the QQR-sgRNA previously digested by BglII and SmaI.

A binary plasmid pK7WGF2-hCas9 that carries the Cas9 protein (SEQ ID NO: 19) was used as the expression vector for Cas9 illustrated in FIG. 1F.

Plant Material and Inoculation

To achieve NptII (neomycin phosphotransferase II) over expressing *Nicotiana benthamiana* plants, wild type *N. benthamiana* leaf disks were inoculated with EHA105 *Agrobacterium* harboring the pCGN1559 vector (Ben-Zvi et al., 2008). NptII resistant plantlets were recovered, self-pollinated, and their F1 progeny was used for further TRV inoculations.

To achieve Cas9/mGUS over expressing *N. tabaccum* plants, mGUS over expressing *Nicotiana tabaccum* plants (Marton et al., 2010) were crossed with eGFP-hCas9 overexpressing plants (Nekrasov et al, 2013) to obtain the F1 progeny that were used for further TRV inoculations.

For leaf infiltration assay, NptII overexpressing *N. benthamiana* seeds were surface sterilized by the vapor-phase method, as previously described (Sugimoto and Meyerowitz 2013). Sterile seeds were then shown individually in petri plates, on quarter strength Murashige and Skoog (MS) (Caisson, USA) medium, supplemented with appropriate vitamins, 1% (w/v) sucrose, 200 mg L−1 kanamycin and 0.8% agarose. 10-d-old Kanamycin resistant plantlets were moved to pots for hardening. Plants were grown for initial 3 weeks before they were subjected to viral inoculation using the leaf infiltration assay (Sparkes et al., 2006). More specifically, *Agrobacterium* cultures were grown overnight at 28° C., 250 rpm, in Luria-Bertani (LB) medium supplemented with 40 mg L−1 kanamycin. Cells were then harvested by centrifugation and resuspended to an $OD_{600}$ of 5 in an infiltration buffer composed of 10 mM $MgCl_2$ and 100 µM acetosyringone. *Agrobacterium* harboring pTRV1 bacterial suspension was mixed with *Agrobacterium* harboring pTRV2 suspension and with *Agrobacterium* harboring binary plasmid carrying the Cas9 expression cassette suspension at a 1:1:1 ratio. The mixed cultures were then diluted 10-fold to a final $OD_{600}$ of 0.5 with infiltration buffer. The *Agrobacterium* suspension was then injected to the abaxial side of a pair of leaves in each individual *N. benthamiana* plant. The inoculated plants were grown in the greenhouse at 25° C. until sampling.

For Agro-dipping assay, F1 seeds obtained from the cross between mGUS over-expressing *N. tabaccum* plants with eGFP-hCas9 over-expressing *N. tabaccum* plants, were surface sterilized and shown individually in petri plates, on quarter strength MS medium, supplemented with appropriate vitamins, 1% (w/v) sucrose, 200 mg L−1 kanamycin and 0.8% agarose. *Agrobacterium* cultures were prepared as described above. pTRV1 bacterial suspension was mixed with pTRV2 suspension at a 1:1 ratio. The mixed cultures were then diluted 10-fold to final $OD_{600}$ of 0.5 with infiltration buffer. Approx. 150 14-d-old kanamycin resistant seedlings were submerged in the *Agrobacterium* solution, and vacuum was applied for 2 minutes. Following treatment, seedlings were moved to MS medium petri plates, supplemented with appropriate vitamins, 1% (w/v) sucrose, and 0.8% agarose, and were placed in darkness for 48 h. Then, seedlings were moved again to new MS medium petri plates, supplemented with appropriate vitamins, 1% (w/v) sucrose, 300 mg L−1 carbenicillin and 0.8% agarose, and were placed in a lighted growth room for recovery for the initial 72 h. To analyze GUS activity, 5 days post-inoculation, seedlings were transferred into 10 ml X-gluc solution (Jefferson, 1986), incubated over-night at 37° C. and washed 3 times with 70% Ethanol solution until blue GUS staining was detectable.

Imaging

A stereoscopic fluorescent microscope (MZFLIII) equipped with a DC300FX camera (Leica Microsystems Ltd.) was used for fluorescence and light imaging of infected plant tissues organs.

Molecular Analysis of Targeted Plants

Total DNA was isolated from Agro-infiltrated *N. benthamiana* leaves (approx sample size of 2 $cm^2$ from inoculated leaf section) using the CTAB extraction method (Murray and Thompson 1980). DNA samples were analyzed for indel mutations using the restriction enzyme site loss method (Marton et al., 2010) Briefly, purified *N. benthamiana* DNA samples were first digested by EheI (Fermentas) for NptII target or MlyI (SchI) (Fermentas) for PDS target. The digested *N. benthamiana* DNA was subjected to PCR amplification using the 5' AGACAATCGGCTGCTCTGAT (SEQ ID NO: 13 and 5' GGCCATTTTCCACCATGATA SEQ ID NO:14, forward and reverse primers, respectively, to amplify 525 bp region carrying NptII target sequence and with 5' GCTTTGCTTGAGAAAAGCTCTC (SEQ ID NO: 15 and 5' ACATAACAAATTCCTTTGCAAGC, SEQ ID NO: 16, forward and reverse primers, respectively, to amplify 450 bp region carrying PDS target sequence.

The amplified PCR products were treated with the appropriate restriction enzyme, and the digestion products were separated by DNA electrophoresis. Specific, restriction enzyme resistant ("un-cut") bands were excised from the gel, purified, and cloned into pGEMT easy T/A cloning vector (Promega) and randomly selected plasmids were analyzed by DNA sequencing.

Total DNA was isolated from Agro-inoculated *N. tabaccum* leaves using the CTAB extraction method (Murray and Thompson 1980). Purified *N. tabaccum* DNA samples were subjected to PCR amplification using the 5' CTATCCTTCGCAAGACCCTTCC (SEQ ID NO: 17) and 5' GTCTGCCAGTTCAGTTCGTTGTTC (SEQ ID NO: 28), forward and reverse primers, respectively, to amplify 670 bp region carrying mGUS target sequence.

The amplified PCR products were digested by Bsu36I (Fermentas), and the digestion products were separated by DNA electrophoresis. Specific, restriction enzyme resistant ("un-cut") bands were excised from the gel, purified, and cloned into pGEMT easy T/A cloning vector (Promega) and randomly selected plasmids were analyzed by DNA sequencing.

Results

Three different TRV constructs were created (FIGS. 1A-C and E). FIGS. 1A and 1B show constructs containing ribozymes flanking the sgRNAs specific to NptII or PDS respectively. The NptII gene is present in a transgenic *N. benthamiana* and the PDS gene is endogenous for *N. benthamiana*. FIG. 1C contains sgRNA cloned into the TRV vector (1C) instead the CP gene, without ribozymes. It was designed for the elimination of a stop codon at the beginning of uidA ORF and to restore expression of GUS in a transgenic *N. tobaccum* transformed with a GUS gene that has been silenced with a stop codon inserted in frame right after the ATG codon (SEQ ID NO: 26, Marton et al., 2010).

TABLE 1

Target and detection method for each of the vectors

| Vector | Target | Event | Detection |
|---|---|---|---|
| 1a | endogenous PDS gene | Deletion in gene | Sequencing |
| 1b | transgenic NptII gene | Deletion in gene | Sequencing |
| 1c | transgenic mGUS gene | In frame-deletion of stop codon | Color & Sequencing |
| 1e | transgenic mGUS gene | In frame-deletion of stop codon | Color & Sequencing |

Briefly, the Single guide RNA sequence (sgRNA) is cloned between a pair of ribozymes: Hammerhead (HH) ribozyme and HDV ribozyme, under the TRV's coat protein sub-genomic promoter. The DsRed2 marker is cloned downstream under a separate viral sub genomic promoter. The pair of ribozymes self-process the RNA molecule in a pre-defined sites, creating a mature, functional guide RNA. This cloning strategy guarantees that if the whole viral replicone is fully transcribed, DsRed2 is detected in the inoculated tissue, and guide RNA is also created in the same tissue. Co-expression of Cas9 protein together with the appropriate sgRNA in the inoculated tissue is supposed to activate the CRISPR machinery to specifically identify and cleave the target sequence.

In order to validate that a TRV vector construct in which flanking ribozymes are present will on one hand express the gene flanked by the ribozymes and on the other hand proliferate sufficiently, a construct with the DsRed reporter gene flanked by ribozymes (TRV vector 1d) was infiltrated into N. benthamiana leaves. In FIG. 2 it can be seen that the DsRed2 still expresses 6 and 10 dpi even in plant parts remote from the infiltration site.

When NptII transgenic N. benthamiana treated by infiltration with mix i or mix ii (Table 2), indels (insertion or deletions) in the respective NptII and PDS genes were observed (FIGS. 3A and B). For example, for NptII target, there were overall 24 indels out of 60 screened sequences—an efficiency of 40%.

TABLE 2

Vector mixes and their experimental purpose

| Mix | Treatment | Target | Detection |
|---|---|---|---|
| i | Binary Plasmid Cas9 + TRV1 + TRV2 – sgNPTII – DsRed (1a) | Viral with ribozyme | NPTII trans gene | Sequencing |
| ii | Binary Plasmid Cas9 + TRV1 + TRV2 – sgPDS – DsRed (1b) | Viral with ribozyme | PDS endogenous gene | Sequencing |
| iii | | | | |
| iv | Binary Plasmid Cas9 + TRV1 + TRV2 – DsRed | Positive control for infection and negative control for sgRNA activity (deletion) | Movement | Color & sequencing (no deletion) |

The system was efficient enough that indels could be detected even without having to perform enrichment as described in the materials and methods for target sites with indels. For PDS target, 3 indels out of 46 screened sequences—an efficiency of 6.5% (FIG. 3B).

FIGS. 4A-C shows that the DsRed reporter is expressed, albeit sporadically, in the plant tissues infected with the ribozyme containing constructs (FIGS. 4A and 4B) proving that despite the ribozymes activity, the virus keeps proliferating, although with less intensity than the control construct (FIG. 4C) and at the same time indels are obtained with high efficiency at the target site (FIGS. 3A and 3B).

In an additional experiment, using construct 1d (Table 1, above) a sgRNA targeting a sequence that includes a GUS repressing stop codon, was inserted into the construct under the Coat Protein (CP) sub genomic promoter. As can be seen in FIG. 5, GUS expression is restored in several cells. Taking into consideration that the indel events are somewhat random (FIGS. 3A-B), the large number of blue cells observed shows high efficiency of the system. This proves that the sgRNA does not have to be cleaved specifically by ribozymes to be functional, and that the present TRV vectors are functional in expressing sgRNA either in the presence or absence of the ribozymes. The significance of ribozyme processing is further discussed in Example 2 below.

DNA analysis on the genome of N. tabaccum (Shown in FIG. 5) treated by #3325 QQR-sgRNA expressing TRV vector (construct 1c (Table 1)) showed a deletion at the expected site of the enzyme (FIG. 6). This confirms that the visible GUS reactivation is as a result of the CRISPR Cas9 activity. The viral vector pTRV ΔCP Δ2b QQR-sgRNA 2spP-DsRed (#3337) was infiltrated into N. benthamiana as well as to Petunia hybrida. In both plants, a very strong systemic infection was observed (FIGS. 7A-B).

Example 2

Ribozyme-Flanked gRNA Increases Editing Efficiency

In order to test the efficiency of ribozyme-mediated processing for genome editing, the activity of two RNA2 designs (FIG. 8 configurations 1A (which is similar to that of the vector in FIG. 1A) and 2A) that contained the same sgRNA sequence, targeting a 20 bp site in the Neomycin phosphotransferase (nptII) gene sequence (termed "nptII-k") were tested. A third construct, 3A (see FIG. 8), was also created as a negative control. Vector 3A has the native viral coat protein and also the DsRed2 gene but no sgRNA. All constructs and their targets are described in Table 1.

The HH ribozyme sgRNA nptII-k HDV ribozyme was ordered as a synthetic sequence (SEQ ID 21). This fragment was cloned into the TRV2 sequence with HindIII and BglII instead the cot protein CDS. The final step was to clone the TRV in to binary plasmid.

TABLE 1 sgRNA vectors and targets list

| Vector # | Target | Event | Detection |
|---|---|---|---|
| 1A | transgenic nptII gene | Indels in gene | PCR and Sequencing |
| 2A | transgenic nptII gene | Indels in gene | PCR and Sequencing |
| 3A | No target | No Indels | PCR |

TABLE 2 sgRNA vectors and treatments list

| Treatment No. | Agro mix details | Infection ration | Treatment Description |
|---|---|---|---|
| 1 | Binary Plasmid with Cas9 + TRV1 + 1A vector | 1:1:1 | Binary and Viral combined |
| 2 | Binary Plasmid with Cas9 + TRV1 + 2A vector | 1:1:1 | Binary and Viral combined |
| 3 | Binary Plasmid with Cas9 + TRV1 + 3A vector | 1:1:1 | Binary and Viral combined |

Other analyses were done as described in Example 1.

Results

Transgenic *N. benthamiana* plants expressing the nptII gene were created. The nptII presence in those plants was approved by PCR and germination on Kanamycin containing growth media. Young leaves of nptII positive *N. benthamiana* plants were inoculated by *Agrobacterium* mix no. 1 or no. 2 (see Table 2 above). As control, other nptII plants were inoculated with *Agrobacterium* mix no. 3. The viral spread in the plant tissues was tested 7 days post-inoculation by monitoring the DsRed2 signal. In plants treated by RNA2 vector that included the ribozymes (configuration 1A of FIG. 8), DsRed2 signal limited to the infiltrated leaves only. No movement of the signal to the stems and shoots was detected (FIG. 9).

In plants treated by RNA2 vector without the ribozymes (2A of FIG. 8), DsRed2 signal was detected both in infiltrated leaves and in remote stems and shoots (FIG. 9). Moreover, the DsRed2 intensity was much higher in the 2A treated leaves then with 1A (FIG. 9).

These results indicate that the ribozymes may interfere with the viral replication and movement by performing continues self-digestion of the viral RNA. While releasing the mature sgRNA, they are also "suicidal", and limiting the viral infection of the whole plant tissues.

Genomic DNA (gDNA) was sampled directly from the inoculated leaves (DsRed2 positive areas) 7 days post inoculation. 3 gDNA samples were extracted from 3 separate plants (3 biological repeats). The restriction-site loss assay was used to check for gene editing activity of the CRISPR/Cas9 systems.

Briefly, the DNA was first digested with EheI restriction enzyme, which cut within the nptII-k target sequence, in order to enrich the samples with mutated sequences. Then, direct PCR amplification of the target segment of the nptII gene (525 bp; SEQ ID 55) was performed using specific primers (SEQ ID 56 and 57). The PCR product was digested with the EheI restriction enzyme, and the uncut band was monitored.

In the 3 control samples (treatment 3), only the non mutated 475 bp+50 bp digestion products were detected in the gel (FIG. 10, the 50 bp band is not visible), while in the 2 experiment samples (treatment 1 and 2), 3 bands could be detected—the non mutated 475 bp and 50 bp digestion products of 525 bp, and the putative mutated product of 525 bp, which is resistant to EheI digestion as a result of gene editing (FIG. 10). By comparing treatments 1 and 2 it was found that the intensity of the 525 bp un-digested band was mostly higher in treatment 1 than in 2, meaning that the presence of the ribozymes in the viral vector increased the amount of mutated sequences in the inoculated tissues.

To further check these results, the uncut, 525 bp PCR products, from both treatments 1 and 2 were purified and cloned to pGEM-T vectors in order to create *E. coli* libraries. 64 individual events were screened from each library and the relevant plasmids were sequenced. In both libraries, nptII-k target sequences were highly detected (FIG. 11). But, while in treatment 1 library (+ribozyme), 93% of sequenced plasmids had indels in the target sequence, in treatment 2 (−ribozyme), only 63% of the sequenced plasmids had indels in the target sequence. This difference clearly shows that the presence of ribozymes in the viral vector design improved the accurate release of the sgRNA, which in turn contribute to the more efficient editing of the target site compared to viral vector carrying the sgRNA without the ribozymes. However, the presence of ribozymes is not necessary for the sgRNA expression from viral vectors, and quite efficient gDNA editing could be detected either way.

To conclude, the addition of ribozymes to the RNA2 vector design greatly increases the gene editing percentage but eventually interferes with viral spread in planta due to self-processing of viral replicones, thus limiting the infectivity capacity of the system.

Example 3

The pTRV System is Able to Simultaneously Deliver Multiple sgRNAs to Different DNA Locations The following was done in order to show that the present TRV based system is capable of efficiently delivering at least 2 sgRNAs simultaneously (from a single RNA2 backbone) to plant cells and together with expression of a Cas9 protein to introduce specific deletions to a DNA fragment in distinct positions. These 2 (or possibly more) sgRNA's can expressed from several separate sub-genomic promoters (examples B3, B4 in FIG. 12) or can be chained one after the other under a single sub genomic promoter (example B2 in FIG. 12) and in all those cases generate indels in 2 (or possibly more) distinct locations simultaneously.

It is shown that the addition of a DsRed2 marker to the RNA2 sequence in order to monitor the viral vector spread does not interfere with the dual sgRNA DNA editing.

Materials and Methods

Design and Cloning 2 sgRNA sequences targeting the nptII gene sequence were generated and named nptII-k (see above, SEQ ID NO: 1) and nptII-l (SEQ ID NO: 53). The distance between those 2 target sequences on the nptII gene is 126 bp. The sgRNA's were cloned in various ways into RNA2 vectors, with or without DsRed2 marker, as described in FIG. 12.

TABLE 3

Multiplexing vectors and targets list

| Vector # | Target | Event | Detection |
| --- | --- | --- | --- |
| B1 | transgenic nptII gene | Indels in gene | PCR and Sequencing |
| B2 | transgenic nptII gene | Indels in gene | PCR |
| B3 | transgenic nptII gene | Indels in gene | PCR |
| B4 | transgenic nptII gene | Indels in gene | PCR |
| 3A | No target | No Indels | PCR |

TABLE 4

Multiplexing vectors and treatments list

| Treatment No. | Agro mix details | Infection ration | Treatment Description |
| --- | --- | --- | --- |
| 1 | Binary Plasmid with Cas9 + TRV1 + B1 vector | 1:1:1 | Binary and Viral combined |
| 2 | Binary Plasmid with Cas9 + TRV1 + B2 vector | 1:1:1 | Binary and Viral combined |
| 3 | Binary Plasmid with Cas9 + TRV1 + B3 vector | 1:1:1 | Binary and Viral combined |
| 4 | Binary Plasmid with Cas9 + TRV1 + B4 vector | 1:1:1 | Binary and Viral combined |
| 5 | Binary Plasmid with Cas9 + TRV1 + 3A vector | 1:1:1 | Binary and Viral combined |

B1 vector constructed first by cloning the nptII-I sgRNA Seq ID 53 into TRV2

As HpaI-XhoI after the PEBV sgP. Then using AatII and SnaBI we cut the 2sgP-nptII-I sgRNA cassette and insert it to 2A instead the DsRed cassette. For vectors B2, B3 and B4 we order a synthetic sequence (SEQ ID 96) with nptII-k sgRNA the 2b sgP and part of DsRed, ends at the PstI site. Vector B2 form by cloning the nptII-k sgRNA as XhoI-BglII fragment to the same sites adjacent to nptII-I sgRNA previously prepare exactly as 2A. To the same TRV vector with nptII-i sgRNA from exactly as 2A we add nptII-k sgRNA as AatII-Bsu36I from the synthetic sequence (SEQ ID 96) to form the B3 vector. Vector B4 form by cloning from SEQ ID 96 the nptII-k sgRNA into the 2A like vector downstream to 2b sgP and fused upstream to the DsRed. In this vector the nptII-k sgRNA and DsRed transcribe from the same promoter.

Other analyses were done as described in Example 1.

Transgenic *N. benthamiana* plants expressing the nptII gene that were described above were used. Young leaves of nptII positive *N. benthamiana* plants were inoculated by *Agrobacterium* mix No. 1 (see Table 4 above). As control, other nptII plants were inoculated with *Agrobacterium* mix No. 5. Genomic DNA (gDNA) was sampled directly from the inoculated tissues 10 days post inoculation. 2 gDNA samples were extracted from 2 separate plants. The DNA was first digested with EheI and PvuII restriction enzymes, which cut within the nptII target sequences, respectively, in order to enrich the sample with mutated sequences. Then, direct PCR amplification of the target segment of the nptII gene (390 bp; SEQ ID NO: 58) was performed using specific primers (SEQ ID NOs: 56 and 59). In the 2 control samples (treatment 5), only the non mutated 390 bp product was amplified, while in the 2 experiment samples (treatment 1), 2 bands could be detected—the non mutated 390 bp product and the putative mutated product of 264 bp (FIG. 13).

Next, the shorter, 264 bp PCR product was purified and directly sequenced (SEQ ID NO: 60) and cloned to pGEM-T vector in order to create an *E. coli* library. Direct sequencing of the purified fragment yielded an exact 126 bp deletion that represents the precise deletion of the segment between the nptII-k and nptII-I target sites (FIG. 14). Sequencing of different plasmids of the library revealed that the 264 bp fragments are more than 50% of the events. Moreover, various fragments with even bigger deletions than 126 bp (FIG. 15, SEQ ID NOs: 61-64) were also detected. Altogether, this data shows that multiplexing using TRV delivered pair of sgRNA's combined with transiently expressed Cas9 is possible and efficient.

DsRed2 was used as a marker for viral vector spread. Adding the DsRed2 to the RNA2-sgRNA enables tracking the infected and potentially mutated tissues in planta.

Thus, 3 more RNA2 constructs were created, each expressing both sgnptII-k/sgnptII-i and DsRed2 with different sub-genomic promoters (see B2, B3, B4 in FIG. 12).

Young leaves of nptII positive *N. benthamiana* plants were inoculated by *Agrobacterium* mix No. 2, mix No. 3 and mix No. 4 (see Table 4 above), each to 3 separate leaves in 3 separate plants. As control, another nptII plant was inoculated with *Agrobacterium* mix No. 5. 7 days post inoculation, the fluorescence was visualized. A high DsRed2 signal was detected in all infiltrated leaves. DsRed2 positive leaf pieces were sampled from all plants.

Genomic DNA (gDNA) was extracted from the DsRed2 positive tissues 7 days post inoculation. Totally, 10 gDNA samples were extracted from 10 separate plants. The DNA was first digested with EheI and PvuII restriction enzymes, which cut within the nptII target sequences, respectively, in order to enrich the sample with mutated sequences. Then, direct PCR amplification of the target segment of the nptII gene (390 bp; SEQ ID NO: 58) was performed. In the control samples (treatment 5), only the non mutated 390 bp product was amplified, while in each of the other 3 experiments (treatments 2, 3, 4), at least one sample that showed 2 PCR bands was detected—the non mutated 390 bp product and the putative mutated product of 264 bp (FIG. 16; SEQ ID NO: 60). There were also cases of amplification of only the non mutated product in some of the experimental repeats. Those could be explained by differences in viral stability or infection quality between samples. Nevertheless, the presence of the shorter (mutated) nptII product in each of the experiments demonstrates that the differently designed RNA2 constructs are all capable of multiplexing, and that the DsRed2 marker addition is not interfering to this ability.

Next, the approach of multiplexing was aimed to modify *petunia* endogenous genes. Indeed as shown below, the pTRV based system is capable of efficient delivering of at least 2 sgRNA's simultaneously (from a single RNA2 backbone) to introduce specific modifications on 2 endogenous *Petunia hybrida* genes (hereafter named TOM1 and TOM3, SEQ ID NOs:94 and 95). The experiments were performed with plants constitutively expressing the Cas9 protein.

Transgenic *Petunia* plants (Blue Ray variety) constitutively expressing the Cas9 gene (SEQ ID NO: 19) were used. Young leaves of Cas9 positive *petunia* plants were inoculated with *Agrobacterium* mix of TRV1 and TRV2 (1:1 ratio, FIG. 17; SEQ ID No: 75). Genomic DNA (gDNA) was sampled directly from the inoculated tissues 10 days post inoculation. The DNA was digested with Bsu36I restriction enzyme, which cuts within each of the TOM's genes target sequences, in order to enrich the sample with mutated sequences. Direct PCR amplification of the target segment of each of the genes was performed using specific primers (SEQ ID NOs: 76-77 for TOM1, SEQ ID 78-79 for TOM3), and another Bsu36I digestion. In TOM1 target site, all 3 samples showed relatively thicker uncut band compared to WT plants (FIG. 18). In TOM3 sample 2 had a significant uncut band compared to WT (FIG. 19).

Next, the uncut band of each gene was purified and cloned into pGEM-T vector in order to create 2 E. coli libraries. Plasmid sequencing of each library revealed that both TOM's target sites were modified: in TOM1's site, most common modification was insertion or deletion of 1 bp, yet a 10 bp and 11 bp deletion appeared too (FIG. 13) (SEQ ID NOs: 82-85). In TOM3's site more variable modifications appeared including insertions and deletions of several bp's (FIG. 14) (SEQ ID NOs: 86-91).

Example 4

Genomic Mutations Introduced by the pTRV System of the Present Invention are Inherited The present inventors now aimed to show that by infecting plant tissue with the viral vector carrying sgRNA in combination with stable Cas9 expression, genomic mutations (indels) are induced and these can be inherited.

To do so, transgenic Tobacco plants (Nicotiana tabacum) that constitutively express both Cas9 protein (SEQ ID NO: 9) and the mutated version of the GUS reporter gene (known as the mGUS; SEQ ID NO: 54).

mGUS has an artificial stop codon (TGA) that is located next to the ATG initiation codon, thus preventing the production of the GUS active protein, as described in Example 1. The sequence flanking the stop codon is called QQR (SEQ ID NO: 46). The first generation Cas9/mGUS Tobacco plants (T0) were self-pollinated and produced T1 seeds that were generally heterozygous for both transgenes. These seeds were used for further treatments. An RNA2 construct was prepared to transcribe a sgRNA to target 20 bp nucleotide sequence located at the QQR site (named sgQQR; in the 5' end of the mGUS, which also included the TGA stop codon). The RNA2 construct included also the DsRed2 marker protein for viral spread monitoring (SEQ ID NO: 18; construct 1E, FIG. 22). The expected outcome of CRISPR induced indel events in this part of the sequence is restoration of the GUS coding sequence at least in portion of the targeted cells in the tissues.

To check the activity of the RNA2 construct, leaves of a young Cas9/mGUS tobacco plant were inoculated with agro mix 1 (Table 5 below). The spread of the DsRed2 signal was followed for 7 days.

The signal was detected in large portions of the infiltrated leaves (FIG. 23). A DsRed2 positive leaf was then detached from the plant, and was used for GUS staining treatment. It was assumed that in part of the genomic editing events, the TGA codon will be eliminated, thus the proper coding sequence of the GUS gene will be re-gained and GUS positive blue colored staining will appear. As expected, a considerable number of GUS positive patches were detected on that leaf surface (FIG. 23). This data suggests that the viral vector together with the constitutive expression of Cas9 efficiently edited the mGUS target by the CRISPR/Cas9 machinery.

Next, Cas9/mGUS Tobacco T1 seedlings were germinated and their cotyledons infected with Agro mix 1 (Table 5).

TABLE 5 mGUS editing vectors and treatments list

| Mix No. | Agro mix details | Infection ration | Treatment |
|---|---|---|---|
| 1 | TRV1 + 1E vector | 1:1 | Viral only |

Seven days post inoculation, the DsRed2 positive cotyledons were excised and moved to plates with Tobacco regeneration media (MS media supplemented with 3% Sucrose, 1.5 µg/ml Zeatin and 0.1 µg/ml NAA—SPECIFY). Altogether, 17 cotyledons were taken that produced 17 calli. Genomic DNA was sampled from all calli, and the presence of both Cas9 and mGUS was confirmed by PCR only in 8 calli. The regeneration process was continued just with those 8 calli. Pieces of calli were sampled for GUS staining to check the CRISPR/Cas9 activity in the tissue (as explained before for the leaf sampling). Once again, patches of blue color were detected indicating a restoration of the GUS coding sequence in some areas of the infected calli tissue (FIG. 24). It should be noted here that in most cases, the mGUS editing does not result in TGA codon elimination or GUS restoration, and probably many of the non-blue calli pieces contain also many indel mutations that could be detected only by sequencing of the target site. Indeed, when gDNA was extracted and analyzed, deletion mutations in the QQR target site could be detected, as exampled in FIG. 25 (SEQ ID NOs: 65-66). 44 plantlets of the developing 8 calli were isolated. All plantlets were moved to plates with rooting media and leaves were sampled from each plant for gDNA analysis and GUS staining. In every plant, PCR was used to amplify a segment of the mGUS coding sequence that contained also the QQR target site. A restriction enzyme that cuts in the middle of the QQR target sequence (Bsu36I) was used in order to check whether it was modified (also known as the restriction site-loss method). In 29 plants (66%), all the PCR product was digested by the restriction enzyme, suggesting that they were not modified at all by the CRISPR/Cas9 system. 9 out of 44 plants (20%) showed partial digestion of the PCR product, meaning that a portion of the amplified PCR product was digested by the restriction enzyme and portion was not, suggesting that either only one mGUS copy was modified or that the plants are chimeric for the indel event. 6 out of 44 plants (13.5%) were completely resistant to digestion of the PCR product, meaning that all the amplified PCR product was not digested by the restriction enzyme. Those plants are the best candidates to transfer the modified allele to the next generation because the molecular analysis of T0 plants has not detected any "wild-type", non modified mGUS sequence. To summarize, 15 out of 44 plants (34%) showed evidence for mutated target alleles in different levels.

Interestingly, 3 out of 44 plants (7%) showed GUS staining, demonstrating recovery of the GUS reading frame as a result of indel mutation. All 3 plants (3E, 3F, 3G) originated from the same calli (Calli #3), and sequencing showed that all had the same 3 bp deletion event, that eliminated the TGA stop codon and produced a proper GUS protein (FIG. 26 and Table 6). Unfortunately, the molecular analysis and the GUS staining pattern of those plants showed that they have a chimeric nature, thus it was less probable that the active GUS allele will be inherited to the next generation (FIG. 26). Thus it was decided to grow for seeds only the 6 plants that showed in the molecular analysis complete resistance for digestion as explained above. The plants lines names and corresponding indel events and SEQ ID's of the mutated QQR target sequences are shown in Table 6, below.

TABLE 6 mGUS mutated plant lines regenerated from viral infected Tobacco calli.

| Plant line # | Indel event | Indel sequence | GUS staining | SEQ ID |
|---|---|---|---|---|
| 3E, 3F, 3G | −3 bp | −CTG | + | 68 |
| 5C | −1 bp | −C | − | 69 |
| 5F | −1 bp | −C | − | 70 |
| 5H | −1 bp | −C | − | 71 |
| 7B | +1 bp | +T | − | 72 |
| 15E | −1 bp | −C | − | 73 |
| 28A | −4 bp | −CTGA | − | 74 |

The 6 mutated plants were self-pollinated and set hundreds of seeds. Ten seeds of each plant were germinated. The young seedlings pool was used to extract gDNA. A segment of the mGUS coding sequence that contained also the QQR target site, was amplified and the restriction enzyme (Bsu36I) was applied. The PCR products of all six plants were still totally resistant to the Bsu36I enzyme, and their sequencing revealed that the exact indel mutation was inherited to the progeny in each and every line checked. A sequence comparison of the modified mGUS alleles of the mother plants (T0) and their progeny (T1) is given in FIG. 27. Those results clearly show that the sgQQR delivered to Tobacco tissue, together with the activity of Cas9 in those tissues, produced modified tobacco plants that stably inherit the mutated allele to their progeny in 100% of the cases checked. The viral vector and experimental approach presented here guarantees inheritance of modified events through the germline.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

Ben Zvi M, Florence N, Masci T, Ovadis M, Shklarman E, Ben-Meir H, Tzfira T, Dudareva N, Vainstein A (2008) Interlinking showy traits: co-engineering of scent and colour biosynthesis in flowers. Plant Biotechnology Journal 6: 403-415;

Jefferson R, Burgess S, Hirsh D (1986) BETA-GLUCURONIDASE FROM ESCHERICHIA-COLI AS A GENE-FUSION MARKER. Proceedings of the National Academy of Sciences of the United States of America 83: 8447-8451 Johnson R A, Gurevich V, Filler S, Samach A, Levy A A (2014), Comparative assessments of CRISPR-Cas nucleases' cleavage efficiency in planta. Plant Mol Biol. November 18;

Murray M, Thompson W (1980) Rapid isolation of high molecular-weight plant DNA. Nucleic Acids Research 8: 4321-4325;

Sparkes I, Runions J, Kearns A, Hawes C (2006) Rapid, transient expression of fluorescent fusion proteins in tobacco plants and generation of stably transformed plants. Nature Protocols 1: 2019-2025;

Sugimoto K, Meyerowitz E M (2013) Regeneration in Arabidopsis tissue culture. Methods Mol Biol. 959: 265-275;

Belhaj K, Chaparro-Garcia A, Kamoun S, Nekrasov V (2013) Plant genome editing made easy: targeted mutagenesis in model and crop plants using CRISPR/Cas system. Plant Methods 9, 39;

Marton I, Zuker A, Shklarman E, Zeevi V, Tovkach A, Roffe S, Ovadis M, Tzfira T and Vainstein A (2010) Non-transgenic genome modification in plant cells. Plant Physiol 154: 1079-1087.

What is claimed is:

1. A nucleic acid construct comprising or encoding a nucleic acid sequence of a tobacco rattle virus (TRV) RNA2 sequence and a single guide RNA (sgRNA) that mediates sequence-specific cleavage in a target sequence of a genome of interest, wherein said TRV RNA2 sequence is devoid of a functional 2b sequence, wherein said TRV RNA2 is devoid of a functional coat protein and wherein said nucleic acid construct replicates and spreads as an RNA virus in a plant.

2. The nucleic acid construct of claim 1, wherein said TRV comprises a heterologous enhancer sequence.

3. The nucleic acid construct of claim 1, wherein said sgRNA comprises at least two sgRNAs.

4. The nucleic acid construct of claim 3, wherein said at least two sgRNAs are directed to a single target gene.

5. The nucleic acid construct of claim 3, wherein said at least two sgRNAs are directed to different target genes.

6. The nucleic acid construct of claim 3, wherein transcription of said at least two sgRNAs is by a single promoter.

7. The nucleic acid construct of claim 1, wherein the nucleic acid construct further comprises an additional nucleic acid sequence encoding a nuclease which binds said sgRNA to cleave genomic DNA in a sequence specific manner.

8. The nucleic acid construct of claim 7, wherein said nuclease is Cas9 or RISC.

9. The nucleic acid construct of claim 1, wherein said target sequence is endogenous to the genome of interest.

10. The nucleic acid construct of claim 1, wherein said target sequence is exogenous to the genome of interest.

11. The nucleic acid construct of claim 1, wherein transcription of said sgRNA and said nuclease is regulated by two separate promoters.

12. A delivery system comprising the nucleic acid construct of claim 1 and a nucleic acid construct encoding a nuclease which binds said sgRNA to cleave genomic DNA in a sequence specific manner.

13. The delivery system of claim 12, wherein said nuclease is Cas9 or RISC.

14. A cell comprising the nucleic acid construct of claim 1.

15. The cell of claim 14 being a plant cell.

16. A method of generating genotypic variation in a genome of a plant, the method comprising introducing into the plant the delivery system of claim 12, wherein said sgRNA mediates sequence-specific cleavage in a target sequence of the plant, thereby generating genotypic variation in the genome of the plant.

17. The method of claim 16, wherein said variation is selected from the group consisting of a deletion, an insertion and a point mutation.

18. The method of claim 16, wherein said variation is stable for at least 2 generations.

19. A method of generating a herbicide resistant plant, the method comprising introducing into the plant the delivery system of claim 12, wherein said sgRNA mediates sequence-specific cleavage in a target sequence of a gene of the plant conferring sensitivity to herbicides, thereby generating the herbicide resistant plant.

20. A method of generating a pathogen resistant plant, the method comprising introducing into the plant the delivery system of claim 12, wherein said sgRNA mediates sequence-specific cleavage in a target sequence of a gene of the plant conferring sensitivity to a pathogen or wherein said sgRNA mediates sequence-specific cleavage in a target sequence of a gene of the pathogen, thereby generating the pathogen resistant plant.

21. A method of generating a plant with increased abiotic stress tolerance, the method comprising introducing into the plant the nucleic acid construct system of claim 12, wherein said sgRNA mediates sequence-specific cleavage in a target sequence of a gene of the plant conferring sensitivity to abiotic stress, thereby generating the plant with increased abiotic stress tolerance.

* * * * *

SEQUENCE LISTING

```
<160> NUMBER OF SEQ ID NOS: 116

<210> SEQ ID NO 1
<211> LENGTH: 103
<212> TYPE: DNA
<213> ORGANISM: Artificial sequence
<220> FEATURE:
<223> OTHER INFORMATION: nucleotide sequence of nptII(k)-sgRNA

<400> SEQUENCE: 1
gctgtcagcg cagggcgcc gttttagagc tagaaatagc aagttaaaat aaggctagtc      60
cgttatcaac ttgaaaaagt ggcaccgagt cggtgctttt ttt                      103

<210> SEQ ID NO 2
<211> LENGTH: 103
<212> TYPE: DNA
<213> ORGANISM: Artificial sequence
```

<220> FEATURE:
<223> OTHER INFORMATION: nucleotide sequence of PDS sgRNA

<400> SEQUENCE: 2

```
gccgttaatt tgagagtcca gttttagagc tagaaatagc aagttaaaat aaggctagtc    60
cgttatcaac ttgaaaaagt ggcaccgagt cggtgctttt ttt                     103
```

<210> SEQ ID NO 3
<211> LENGTH: 167
<212> TYPE: DNA
<213> ORGANISM: Artificial sequence
<220> FEATURE:
<223> OTHER INFORMATION: nucleotide sequence of QQR sgRNA cassette

<400> SEQUENCE: 3

```
gatatcaagc ttgttaacga ggtaattctt cccctcagga ggttttagag ctagaaatag    60
caagttaaaa taaggctagt ccgttatcaa cttgaaaaag tggcaccgag tcggtgcttt   120
ttttctcgag ggatttaagg acgtgaactc tgttgagatc ttacgta                 167
```

<210> SEQ ID NO 4
<211> LENGTH: 43
<212> TYPE: DNA
<213> ORGANISM: Artificial sequence
<220> FEATURE:
<223> OTHER INFORMATION: nucleotide sequence of Hammerhead (HH) ribozyme

<400> SEQUENCE: 4

```
ggccatctga tgagtccgtg aggacgaaac gagtaagctc gtc                      43
```

<210> SEQ ID NO 5
<211> LENGTH: 68
<212> TYPE: DNA
<213> ORGANISM: Artificial sequence
<220> FEATURE:
<223> OTHER INFORMATION: nucleotide sequence of hepatitis delta virus
      (HDV) ribozyme

<400> SEQUENCE: 5

```
ggccggcatg gtcccagcct cctcgctggc gccggctggg caacatgctt cggcatggcg    60
aatgggac                                                             68
```

<210> SEQ ID NO 6
<211> LENGTH: 1275
<212> TYPE: DNA
<213> ORGANISM: Artificial sequence
<220> FEATURE:
<223> OTHER INFORMATION: nucleotide sequence of pTRV2 CP- 2b with the
      QQR-sgRNA

<400> SEQUENCE: 6

```
ataaaacatt gcacctatgg tgttgccctg ctggggtat gtcagtgatc gcagtagaat     60
gtactaattg acaagttgga gaatacggta gaacgtcctt atccaacaca gcctttatcc   120
ctctccctga cgaggttttt gtcagtgtaa tatttctttt tgaactatcc agcttagtac   180
cgtacgggaa agtgactggt gtgcttatct ttgaaatgtt actttgggtt tcggttcttt   240
aggttagtaa gaaagcactt gtcttctcat acaaaggaaa acctgagacg tatcgcttac   300
gaaagtagca atgaaagaaa ggtggtggtt ttaatcgcta ccgcaaaaac gatggggtcg   360
ttttaattaa cttctcctac gcaagcgtct aaacggacgt ggggttttg ctagtttctt   420 tagagaaaac tagctaagtc tttaatgtta tcattagaga tggcataaat ataatacttg   480
```

```
tgtctgctga taagatcatt ttaatttgga cgattagact tgttgaacta caggttactg    540
aatcacttgc gctaatcaac aagcttaaaa gcttgttaac gaggtaattc ttcccctcag    600
gaggttttag agctagaaat agcaagttaa aataaggcta gtccgttatc aacttgaaaa    660
agtggcaccg agtcggtgct ttttttctcg agggatttaa ggacgtgaac tctgttgaga    720
tctctgtgaa attcagaggg tgggtgatac catattcact gatgccatta gcgacatcta    780
aatagggcta attgtgacta atttgaggga atttccttta ccattgacgt cagtgtcgtt    840
ggtagcattt gagtttcgaa ttctctagaa ggcctccatg gggatccggt accgagctca    900
cgcgtctcga ggcccgggca tgtcccgaag acattaaact acggttcttt aagtagatcc    960
gtgtctgaag ttttaggttc aatttaaacc tacgagattg acattctcga ctgatcttga   1020
ttgatcggta agtcttttgt aatttaattt tcttttttgat tttatttaa attgttatct   1080 gtttctgtgt atagactgtt tgagatcggc gtttggccga ctcattgtct taccataggg   1140
gaacggactt tgtttgtgtt gttatttat ttgtatttta ttaaaattct caacgatctg   1200
aaaaagcctc gcggctaaga gattgttggg gggtgagtaa gtacttttaa agtgatgatg   1260
gttacaaagg caaaa                                                    1275

<210> SEQ ID NO 7
<211> LENGTH: 2546
<212> TYPE: DNA
<213> ORGANISM: Artificial sequence
<220> FEATURE:
<223> OTHER INFORMATION: nucleotide sequence of pTRV2 CP-nptII(k)-sgRNA:
      2b:DsRed

<400> SEQUENCE: 7
ggattgatgt gatatctcca ctgacgtaag ggatgacgca caatcccact atccttcgca     60
agacccttcc tctatataag gaagttcatt tcatttggag aggatccggc gcgccataaa    120
acattgcacc tatggtgttg ccctggctgg ggtatgtcag tgatcgcagt agaatgtact    180
aattgacaag ttggagaata cggtagaacg tccttatcca acacagcctt tatccctctc    240
cctgacgagg ttttttgtcag tgtaatattt cttttttgaac tatccagctt agtaccgtac    300
gggaaagtga ctggtgtgct tatctttgaa atgttacttt gggtttcggt tctttaggtt    360
agtaagaaag cacttgtctt ctcatacaaa ggaaaacctg agacgtatcg cttacgaaag    420
tagcaatgaa agaaaggtgg tggttttaat cgctaccgca aaaacgatgg ggtcgtttta    480
attaacttct cctacgcaag cgtctaaacg gacgttgggg ttttgctagt ttctttagag    540
aaaactagct aagtctttaa tgttatcatt agagatggca taaatataat acttgtgtct    600
gctgataaga tcatttttaat ttggacgatt agacttgttg aactacaggt tactgaatca    660
cttgcgctaa tcaacaagct tgttaacgag gccatctga tgagtccgtg aggacgaaac    720
gagtaagctc gtcgctgtca gcgcaggggc gccgttttag agctagaaat agcaagttaa    780
aataaggcta gtccgttatc aacttgaaaa agtggcaccg agtcggtgct ttttttggcc    840
ggcatggtcc cagcctcctc gctggcgccg gctgggcaac atgcttcggc atggcgaatg    900
ggacctcgag gtcgacagct ggatttaagg acgtgaactc tgttgagatc tctgtgaaat    960
tcagagggtg gtgatacca tattcactga tgccattagc gacatctaaa tagggctaat   1020
tgtgactaat tgagggaat ttccttacc attgacgtca gtgtcgttgg tagcatttga    1080
gtttcgtaac tataacggtc ctaaggtagc gaacatcttg ttctgggtt tcacactatc    1140 tttagagaaa gtgttaagtt aattaagtta tcttaattaa gagcataatt atactgattt    1200
```

```
gtctctcgtt gatagagtct atcattctgt tactaaaaat ttgacaactc ggtttgctga      1260
cctactggtt actgtatcac ttacccgagt taacgagatg gcctcctccg agaacgtcat      1320
caccgagttc atgcgcttca aggtgcgcat ggagggcacc gtgaacggcc acgagttcga      1380
gatcgagggc gagggcgagg gccgccccta cgagggccac aacaccgtga agctgaaggt      1440
gaccaagggc ggccccctgc ccttcgcctg gacatcctg tcccccagt tccagtacgg       1500 ctccaaggtg tacgtgaagc accccgccga catccccgac tacaagaagc tgtccttccc      1560
cgagggcttc aagtgggagc gcgtgatgaa cttcgaggac ggcggcgtgg cgaccgtgac      1620
ccaggactcc tccctgcagg acggctgctt catctacaag gtgaagttca tcggcgtgaa      1680
cttcccctcc gacggccccg tgatgcagaa gaagaccatg ggctgggagg cctccaccga      1740
gcgcctgtac ccccgcgacg gcgtgctgaa gggcgagacc cacaaggccc tgaagctgaa      1800
ggacggcggc cactacctgg tggagttcaa gtccatctac atggccaaga agcccgtgca      1860 gctgccggc tactactacg tggacgccaa gctggacatc acctcccaca acgaggacta      1920
caccatcgtg gagcagtacg agcgcaccga gggccgccac acctgttcc tgtgagtcga     1980 ccccgaagac attaaactac ggttctttaa gtagatccgt gtctgaagtt taggttcaat      2040
ttaaacctac gagattgaca ttctcgactg atcttgattg atcggtaagt cttttgtaat      2100
ttaattttct ttttgatttt attttaaatt gttatctgtt tctgtgtata gactgtttga      2160
gatcggcgtt tggccgactc attgtcttac catagggaa cggactttgt tgtgttgtt       2220 attttatttg tattttatta aaattctcaa cgatctgaaa aagcctcgcg gctaagagat      2280
tgttgggggg tgagtaagta cttttaaagt gatgatggtt acaaaggcaa aaggggtaaa     2340
acccctcgcc tacgtaagcg ttattacgcc cgtctgtact tatatcagta cactgacgag      2400
tccctaaagg acgaaacggg aggaattctg caggagtggg gaggcacgat ggccgctttg     2460
gtcgatcgac gggatcgatc ctgctttaat gagatatgcg agacgcctat gatcgcatga      2520
tatttgcttt caattctgtt gtgcac                                         2546

<210> SEQ ID NO 8
<211> LENGTH: 2546
<212> TYPE: DNA
<213> ORGANISM: Artificial sequence
<220> FEATURE:
<223> OTHER INFORMATION: nucleotide sequence of pTRV2 CP-PDS-sgRNA:
      2b:DsRed

<400> SEQUENCE: 8
ggattgatgt gatatctcca ctgacgtaag ggatgacgca caatcccact atccttcgca       60
agacccttcc tctatataag gaagttcatt tcatttggag aggatccggc gcgccataaa      120
acattgcacc tatggtgttg ccctggctgg ggtatgtcag tgatcgcagt agaatgtact      180
aattgacaag ttggagaata cggtagaacg tccttatcca acacagcctt tatccctctc      240
cctgacgagg ttttttgtcag tgtaatattt cttttttgaac tatccagctt agtaccgtac      300
gggaaagtga ctggtgtgct tatctttgaa atgttacttt gggtttcggt tctttaggtt      360
agtaagaaag cacttgtctt ctcatacaaa ggaaaacctg agacgtatcg cttacgaaag      420
tagcaatgaa agaaaggtgg tggttttaat cgctaccgca aaaacgatgg ggtcgtttta      480
attaacttct cctacgcaag cgtctaaacg gacgttgggg ttttgctagt ttctttagag      540
aaaactagct aagtctttaa tgttatcatt agagatggca taaatataat acttgtgtct      600
gctgataaga tcatttttaat ttggacgatt agacttgttg aactacaggt tactgaatca      660
```

-continued

```
cttgcgctaa tcaacaagct tgttaacgag ggccatctga tgagtccgtg aggacgaaac      720
gagtaagctc gtcgccgtta atttgagagt ccagttttag agctagaaat agcaagttaa      780
aataaggcta gtccgttatc aacttgaaaa agtggcaccg agtcggtgct ttttttggcc      840
ggcatggtcc cagcctcctc gctggcgccg gctgggcaac atgcttcggc atggcgaatg      900
ggacctcgag gtcgacagct ggatttaagg acgtgaactc tgttgagatc tctgtgaaat      960
tcagagggtg ggtgatacca tattcactga tgccattagc gacatctaaa tagggctaat     1020
tgtgactaat ttgagggaat tccttttacc attgacgtca gtgtcgttgg tagcatttga     1080
gtttcgtaac tataacggtc ctaaggtagc gaacatcttg ttctgggggtt tcacactatc     1140 tttagagaaa gtgttaagtt aattaagtta tcttaattaa gagcataatt atactgattt     1200
gtctctcgtt gatagagtct atcattctgt tactaaaaat ttgacaactc ggtttgctga     1260
cctactggtt actgtatcac ttacccgagt taacgagatg gcctcctccg agaacgtcat     1320
caccgagttc atgcgcttca aggtgcgcat ggagggcacc gtgaacggcc acgagttcga     1380
gatcgagggc gagggcgagg gccgccccta cgagggccac aacaccgtga agctgaaggt     1440
gaccaagggc ggccccctgc ccttcgcctg gacatcctg tccccccagt tccagtacgg     1500
ctccaaggtg tacgtgaagc accccgccga catccccgac tacaagaagc tgtccttccc     1560
cgagggcttc aagtgggagc gcgtgatgaa cttcgaggac ggcggcgtgg cgaccgtgac     1620
ccaggactcc tccctgcagg acggctgctt catctacaag gtgaagttca tcggcgtgaa     1680 cttccccctcc gacggccccg tgatgcagaa gaagaccatg ggctgggagg cctccaccga     1740
gcgcctgtac ccccgcgacg gcgtgctgaa gggcgagacc cacaaggccc tgaagctgaa     1800
ggacggcggc cactacctgg tggagttcaa gtccatctac atggccaaga gcccgtgca     1860 gctgcccggc tactactacg tggacgccaa gctggacatc acctcccaca acgaggacta     1920
caccatcgtg gagcagtacg agcgcaccga gggccgccac cacctgttcc tgtgagtcga     1980
ccccgaagac attaaactac ggttctttaa gtagatccgt gtctgaagtt taggttcaat     2040
ttaaacctac gagattgaca ttctcgactg atcttgattg atcggtaagt cttttgtaat     2100 ttaatttttct ttttgattt atttttaaatt gttatctgtt tctgtgtata gactgtttga     2160
gatcggcgtt tggccgactc attgtcttac catagggggaa cggactttgt tgtgttgtt     2220 atttttatttg tattttatta aaattctcaa cgatctgaaa aagcctcgcg gctaagagat     2280 tgttggggggg tgagtaagta cttttaaagt gatgatggtt acaaaggcaa aaggggtaaa     2340
acccctcgcc tacgtaagcg ttattacgcc cgtctgtact tatatcagta cactgacgag     2400
tccctaaagg acgaaacggg aggaattctg caggagtggg gaggcacgat ggccgctttg     2460
gtcgatcgac gggatcgatc ctgctttaat gagatatgcg agacgcctat gatcgcatga     2520
tatttgcttt caattctgtt gtgcac                                           2546
```

<210> SEQ ID NO 9
<211> LENGTH: 4104
<212> TYPE: DNA
<213> ORGANISM: Artificial sequence
<220> FEATURE:
<223> OTHER INFORMATION: nucleotide sequence of Cas9

<400> SEQUENCE: 9

```
atggacaaga agtactccat tgggctcgat atcggcacaa acagcgtcgg ctgggccgtc       60
attacggacg agtacaaggt gccgagcaaa aaattcaaag ttctgggcaa taccgatcgc      120
cacagcataa agaagaacct cattggcgcc ctcctgttcg actccgggga gacggccgaa      180
```

```
gccacgcggc tcaaaagaac agcacggcgc agatataccc gcagaaagaa tcggatctgc    240
tacctgcagg agatctttag taatgagatg gctaaggtgg atgactcttt cttccatagg    300
ctggaggagt cctttttggt ggaggaggat aaaaagcacg agcgccaccc aatctttggc    360
aatatcgtgg acgaggtggc gtaccatgaa aagtacccaa ccatatatca tctgaggaag    420
aagcttgtag acagtactga taaggctgac ttgcggttga tctatctcgc gctggcgcat    480
atgatcaaat ttcggggaca cttcctcatc gaggggacc tgaacccaga caacagcgat     540
gtcgacaaac tctttatcca actggttcag acttacaatc agcttttcga agagaacccg    600
atcaacgcat ccgagttga cgccaaagca atcctgagcg ctaggctgtc caatcccgg     660 cggctcgaaa acctcatcgc acagctccct ggggagaaga agaacggcct gtttggtaat    720
cttatcgccc tgtcactcgg gctgacccc aactttaaat ctaacttcga cctggccgaa    780
gatgccaagc ttcaactgag caaagacacc tacgatgatg atctcgacaa tctgctggcc    840
cagatcggcg accagtacgc agacctttt ttggcggcaa agaacctgtc agacgccatt     900
ctgctgagtg atattctgcg agtgaacacg gagatcacca agctccgct gagcgctagt     960 atgatcaagc gctatgatga gcaccaccaa gacttgactt tgctgaaggc ccttgtcaga   1020
cagcaactgc ctgagaagta caaggaaatt ttcttcgatc agtctaaaaa tggctacgcc   1080
ggatacattg acgcggagc aagccaggag gaattttaca aatttattaa gcccatcttg     1140 gaaaaatgg acggcaccga ggagctgctg gtaaagctta acagagaaga tctgttgcgc    1200
aaacagcgca ctttcgacaa tggaagcatc ccccaccaga ttcacctggg cgaactgcac    1260
gctatcctca ggcggcaaga ggatttctac ccctttttga aagataacag ggaaaagatt    1320
gagaaaatcc tcacatttcg gatacctac tatgtaggcc ccctcgcccg ggaaattcc     1380 agattcgcgt ggatgactcg caatcagaa gagaccatca ctccctggaa cttcgaggaa    1440
gtcgtggata agggggcctc tgcccagtcc ttcatcgaaa ggatgactaa ctttgataaa   1500
aatctgccta acgaaaaggt gcttcctaaa cactctctgc tgtacgagta cttcacagtt    1560
tataacgagc tcaccaaggt caaatacgtc acagaaggga tgagaaagcc agcattcctg   1620
tctggagagc agaagaaagc tatcgtggac ctcctcttca agacgaaccg gaaagttacc   1680
gtgaaacagc tcaaagaaga ctatttcaaa aagattgaat gtttcgactc tgttgaaatc   1740
agcggagtgg aggatcgctt caacgcatcc ctgggaacgt atcacgatct cctgaaaatc   1800
attaaagaca aggacttcct ggacaatgag gagaacgagg acattcttga ggacattgtc   1860 ctcacccta cgttgtttga agataggag atgattgaag aacgcttgaa aacttacgct     1920
catctcttcg acgacaaagt catgaaacag ctcaagaggc gccgatatac aggatggggg   1980
cggctgtcaa gaaaactgat caatgggatc cgagacaagc agagtggaaa gacaatcctg   2040 gatttttctta gtccgatgg atttgccaac cggaacttca tgcagttgat ccatgatgac   2100
tctctcacct ttaaggagga catccagaaa gcacaagttt ctggccaggg ggacagtctt   2160
cacgagcaca tcgctaatct tgcaggtagc ccagctatca aaaagggaat actgcagacc   2220
gttaaggtcg tggatgaact cgtcaaagta atgggaaggc ataagcccga gaatatcgtt   2280
atcgagatgg cccgagagaa ccaaactacc cagaagggac agaagaacag tagggaaagg   2340
atgaagagga ttgaagaggg tataaaagaa ctggggtccc aaatccttaa ggaacaccca   2400
gttgaaaaca cccagcttca gaatgagaag ctctacctgt actacctgca gaacggcagg   2460
gacatgtacg tggatcagga actggacatc aatcggctct ccgactacga cgtggatcat   2520
```

```
atcgtgcccc agtcttttct caaagatgat tctattgata ataaagtgtt gacaagatcc   2580
gataaaaata gagggaagag tgataacgtc ccctcagaag aagttgtcaa gaaaatgaaa   2640
aattattggc ggcagctgct gaacgccaaa ctgatcacac aacggaagtt cgataatctg   2700
actaaggctg aacgaggtgg cctgtctgag ttggataaag ccggcttcat caaaaggcag   2760
cttgttgaga cacgccagat caccaagcac gtggcccaaa ttctcgattc acgcatgaac   2820
accaagtacg atgaaaatga caaactgatt cgagaggtga agttattac tctgaagtct   2880
aagctggtct cagatttcag aaaggacttt cagtttata aggtgagaga gatcaacaat   2940
taccaccatg cgcatgatgc ctacctgaat gcagtggtag gcactgcact tatcaaaaaa   3000
tatcccaagc ttgaatctga atttgtttac ggagactata agtgtacga tgttaggaaa   3060
atgatcgcaa agtctgagca ggaaataggc aaggccaccg ctaagtactt cttttacagc   3120
aatattatga atttttcaa gaccgagatt acactggcca atggagagat tcggaagcga   3180
ccacttatcg aaacaaacgg agaaacagga gaaatcgtgt gggacaaggg tagggatttc   3240
gcgacagtcc ggaaggtcct gtccatgccg caggtgaaca tcgttaaaaa gaccgaagta   3300
cagaccggag gcttctccaa ggaaagtatc ctcccgaaaa ggaacagcga caagctgatc   3360
gcacgcaaaa aagattggga ccccaagaaa tacggcggat tcgattctcc tacagtcgct   3420
tacagtgtac tggttgtggc caaagtggag aaagggaagt ctaaaaaact caaaagcgtc   3480
aaggaactgc tgggcatcac aatcatggag cgatcaagct tcgaaaaaaa ccccatcgac   3540
tttctcgagg cgaaaggata taagaggtc aaaaagacc tcatcattaa gcttcccaag   3600
tactctctct tgagcttga aaacggccgg aaacgaatgc tcgctagtgc gggcgagctg   3660
cagaaaggta acgagctggc actgccctct aaatacgtta atttcttgta tctggccagc   3720
cactatgaaa agctcaaagg gtctcccgaa gataatgagc agaagcagct gttcgtggaa   3780
caacacaaac actaccttga tgagatcatc gagcaaataa gcgaattctc caaaagagtg   3840
atcctcgccg acgctaacct cgataaggtg ctttctgctt acaataagca cagggataag   3900
cccatcaggg agcaggcaga aaacattatc cacttgttta ctctgaccaa cttgggcgcg   3960
cctgcagcct tcaagtactt cgacaccacc atagacagaa agcggtacac ctctacaaag   4020
gaggtcctgg acgccacact gattcatcag tcaattacgg ggctctatga aacaagaatc   4080
gacctctctc agctcggtgg agac                                          4104
```

<210> SEQ ID NO 10
<211> LENGTH: 1368
<212> TYPE: PRT
<213> ORGANISM: Artificial sequence
<220> FEATURE:
<223> OTHER INFORMATION: Cas9 AA sequence

<400> SEQUENCE: 10

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

-continued

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
        100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser

-continued

```
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
        690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
        770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
```

-continued

```
Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320
```

```
Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
ctatccttcg caagacccTt cc                                          22

<210> SEQ ID NO 12
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 12
gtctgccagt tcagttcgtt gttc                                        24

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
agacaatcgg ctgctctgat                                             20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
ggccattttc caccatgata                                             20

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
gctttgcttg agaaaagctc tc                                          22

<210> SEQ ID NO 16
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 16
```
acataacaaa ttcctttgca agc          23

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
ctatccttcg caagaccctt cc          22

<210> SEQ ID NO 18
<211> LENGTH: 2147
<212> TYPE: DNA
<213> ORGANISM: Artificial sequence
<220> FEATURE:
<223> OTHER INFORMATION: nucleotide sequence of pTRV CP 2b QQR-sgRNA 2spP-DsRed

<400> SEQUENCE: 18
cattgcacct atggtgttgc cctggctggg gtatgtcagt gatcgcagta gaatgtacta          60
attgacaagt tggagaatac ggtagaacgt ccttatccaa cacagccttt atccctctcc         120
ctgacgaggt ttttgtcagt gtaatatttc tttttgaact atccagctta gtaccgtacg         180
ggaaagtgac tggtgtgctt atctttgaaa tgttactttg ggtttcggtt ctttaggtta         240
gtaagaaagc acttgtcttc tcatacaaag gaaaacctga gacgtatcgc ttacgaaagt         300
agcaatgaaa gaaggtggt ggttttaatc gctaccgcaa aaacgatggg gtcgttttaa         360
ttaacttctc ctacgcaagc gtctaaacgg acgttggggt tttgctagtt tctttagaga         420
aaactagcta agtctttaat gttatcatta gagatggcat aaatataata cttgtgtctg         480
ctgataagat catttaatt tggacgatta gacttgttga actacaggtt actgaatcac         540
ttgcgctaat caacaagctt aaaagcttgt taacgaggta attcttcccc tcaggaggtt         600
ttagagctag aaatagcaag ttaaaataag gctagtccgt tatcaacttg aaaaagtggc         660
accgagtcgg tgcttttttt ctcgagggat ttaaggacgt gaactctgtt gagatctctg         720
tgaaattcag agggtgggtg ataccatatt cactgatgcc attagcgaca tctaaatagg         780
gctaattgtg actaatttga gggaatttcc tttaccattg acgtcagtgt cgttggtagc         840
atttgagttt cgtaactata acggtcctaa ggtagcgaac atcttgttct ggggtttcac         900
actatcttta gagaaagtgt taagttaatt aagttatctt aattaagagc ataattatac         960
tgatttgtct ctcgttgata gagtctatca ttctgttact aaaaatttga caactcggtt        1020
tgctgaccta ctggttactg tatcacttac ccgagttaac gagatggcct cctccgagaa        1080
cgtcatcacc gagttcatgc gcttcaaggt gcgcatggag ggcaccgtga acggccacga        1140
gttcgagatc gagggcgagg gcgagggccg cccctacgag ggcacaaca ccgtgaagct        1200 gaaggtgacc aagggcggcc ccctgccctt cgcctgggac atcctgtccc ccagttcca        1260 gtacggctcc aaggtgtacg tgaagcaccc cgccgacatc cccgactaca agaagctgtc        1320
cttccccgag ggcttcaagt gggagcgcgt gatgaacttc gaggacggcg gcgtggcgac        1380
cgtgacccag gactcctccc tgcaggacgg ctgcttcatc tacaaggtga agttcatcgg        1440
cgtgaacttc ccctccgacg gccccgtgat gcagaagaag accatgggct gggaggcctc        1500
caccgagcgc ctgtaccccc gcgacggcgt gctgaagggc gagacccaca aggccctgaa        1560
gctgaaggac ggcggccact acctggtgga gttcaagtcc atctacatgg ccaagaagcc        1620

-continued

| | |
|---|---|
| cgtgcagctg cccggctact actacgtgga cgccaagctg acatcacct cccacaacga | 1680 |
| ggactacacc atcgtggagc agtacgagcg caccgagggc cgccaccacc tgttcctgtg | 1740 |
| agtcgaccgg gcatgtcccg aagacattaa actacggttc tttaagtaga tccgtgtctg | 1800 |
| aagttttagg ttcaatttaa acctacgaga ttgacattct cgactgatct tgattgatcg | 1860 |
| gtaagtcttt tgtaatttaa ttttcttttt gattttattt taaattgtta tctgtttctg | 1920 |
| tgtatagact gtttgagatc ggcgtttggc cgactcattg tcttaccata ggggaacgga | 1980 |
| ctttgtttgt gttgttattt tatttgtatt ttattaaaat tctcaacgat ctgaaaaagc | 2040 |
| ctcgcggcta agagattgtt gggggtgag taagtacttt taaagtgatg atggttacaa | 2100 |
| aggcaaaagg ggtaaaaccc ctcgcctacg taagcgttat tacgccc | 2147 |

<210> SEQ ID NO 19
<211> LENGTH: 14400
<212> TYPE: DNA
<213> ORGANISM: Artificial sequence
<220> FEATURE:
<223> OTHER INFORMATION: nucleotide sequence of pK7WGF2-hCas9

<400> SEQUENCE: 19

| | |
|---|---|
| atggacaaga agtactccat tgggctcgat atcggcacaa acagcgtcgg ctgggccgtc | 60 |
| attacggacg agtacaaggt gccgagcaaa aaattcaaag ttctgggcaa taccgatcgc | 120 |
| cacagcataa agaagaacct cattggcgcc ctcctgttcg actccgggga cggccgaa | 180 |
| gccacgcggc tcaaaagaac agcacggcgc agatataccc gcagaaagaa tcggatctgc | 240 |
| tacctgcagg agatctttag taatgagatg gctaaggtgg atgactcttt cttccatagg | 300 |
| ctggaggagt cctttttggt ggaggaggat aaaaagcacg agcgccaccc aatctttggc | 360 |
| aatatcgtgg acgaggtggc gtaccatgaa aagtacccaa ccatatatca tctgaggaag | 420 |
| aagcttgtag acagtactga taaggctgac ttgcggttga tctatctcgc gctggcgcat | 480 |
| atgatcaaat ttcggggaca cttcctcatc gagggggacc tgaacccaga caacagcgat | 540 |
| gtcgacaaac tctttatcca actggttcag acttacaatc agcttttcga agagaacccg | 600 |
| atcaacgcat ccgagttga cgccaaagca atcctgagcg ctaggctgtc caaatcccgg | 660 |
| cggctcgaaa acctcatcgc acagctccct ggggagaaga gaacggcct gtttggtaat | 720 |
| cttatcgccc tgtcactcgg gctgaccccc aactttaaat ctaacttcga cctggccgaa | 780 |
| gatgccaagc ttcaactgag caaagacacc tacgatgatg atctcgacaa tctgctggcc | 840 |
| cagatcggcg accagtacgc agaccttttt ttggcggcaa agaacctgtc agacgccatt | 900 |
| ctgctgagtg atattctgcg agtgaacacg gagatcacca agctccgct gagcgctagt | 960 |
| atgatcaagc gctatgatga gcaccaccaa gacttgactt tgctgaaggc ccttgtcaga | 1020 |
| cagcaactgc ctgagaagta caaggaaatt ttcttcgatc agtctaaaaa tggctacgcc | 1080 |
| ggatacattg acggcggagc aagccaggag gaattttaca aatttattaa gcccatcttg | 1140 |
| gaaaaaatgg acggcaccga ggagctgctg gtaaagctta acagaagaa tctgttgcgc | 1200 |
| aaacagcgca ctttcgacaa tggaagcatc ccccaccaga ttcacctggg cgaactgcac | 1260 |
| gctatcctca gcggcaaga ggatttctac ccctttttga agataacag ggaaaagatt | 1320 |
| gagaaaatcc tcacatttcg gataccctac tatgtaggcc ccctcgcccg ggaaaattcc | 1380 |
| agattgcgt ggatgactcg caaatcagaa gagaccatca ctccctggaa cttcgaggaa | 1440 |
| gtcgtggata ggggggcctc tgcccagtcc ttcatcgaaa ggatgactaa cttttgataaa | 1500 |
| aatctgccta acgaaaaggt gcttcctaaa cactctctgc tgtacgagta cttcacagtt | 1560 |

```
tataacgagc tcaccaaggt caaatacgtc acagaaggga tgagaaagcc agcattcctg   1620
tctggagagc agaagaaagc tatcgtggac ctcctcttca agacgaaccg gaaagttacc   1680
gtgaaacagc tcaaagaaga ctatttcaaa aagattgaat gtttcgactc tgttgaaatc   1740
agcggagtgg aggatcgctt caacgcatcc ctgggaacgt atcacgatct cctgaaaatc   1800
attaaagaca aggacttcct ggacaatgag gagaacgagg acattcttga ggacattgtc   1860
ctcaccctta cgttgtttga agatagggag atgattgaag aacgcttgaa aacttacgct   1920
catctcttcg acgacaaagt catgaaacag ctcaagaggc gccgatatac aggatggggg   1980
cggctgtcaa gaaaactgat caatgggatc cgagacaagc agagtggaaa gacaatcctg   2040
gattttctta agtccgatgg atttgccaac cggaacttca tgcagttgat ccatgatgac   2100
tctctcacct ttaaggagga catccagaaa gcacaagttt ctggccaggg ggacagtctt   2160
cacgagcaca tcgctaatct tgcaggtagc ccagctatca aaaagggaat actgcagacc   2220
gttaaggtcg tggatgaact cgtcaaagta atgggaaggc ataagcccga gaatatcgtt   2280
atcgagatgg cccgagagaa ccaaactacc cagaagggac agaagaacag tagggaaagg   2340
atgaagagga ttgaagaggg tataaaagaa ctggggtccc aaatccttaa ggaacaccca   2400
gttgaaaaca cccagcttca gaatgagaag ctctacctgt actacctgca gaacggcagg   2460
gacatgtacg tggatcagga actggacatc aatcggctct ccgactacga cgtggatcat   2520
atcgtgcccc agtctttttct caaagatgat tctattgata taaagtgtt gacaagatcc   2580 gataaaaata gagggaagag tgataacgtc ccctcagaag aagttgtcaa gaaaatgaaa   2640
aattattggc ggcagctgct gaacgccaaa ctgatcacac aacggaagtt cgataatctg   2700
actaaggctg aacgaggtgg cctgtctgag ttggataaag ccggcttcat caaaaggcag   2760
cttgttgaga cacgccagat caccaagcac gtggcccaaa ttctcgattc acgcatgaac   2820
accaagtacg atgaaaatga caaactgatt cgagaggtga agttattac tctgaagtct   2880 aagctggtct cagatttcag aaaggacttt cagtttttata aggtgagaga gatcaacaat   2940
taccaccatg cgcatgatgc ctacctgaat gcagtggtag gcactgcact tatcaaaaaa   3000
tatcccaagc ttgaatctga atttgtttac ggagactata agtgtacga tgttaggaaa   3060 atgatcgcaa agtctgagca ggaaataggc aaggccaccg ctaagtactt cttttacagc   3120
aatattatga atttttttcaa gaccgagatt acactggcca atggagagat tcggaagcga   3180
ccacttatcg aaacaaacgg agaaacagga gaaatcgtgt gggacaaggg tagggatttc   3240
gcgacagtcc ggaaggtcct gtccatgccg caggtgaaca tcgttaaaaa gaccgaagta   3300
cagaccggag gcttctccaa ggaaagtatc ctcccgaaaa ggaacagcga caagctgatc   3360
gcacgcaaaa aagattggga ccccaagaaa tacggcggat cgattctcc tacagtcgct   3420 tacagtgtac tggttgtggc caaagtggag aaagggaagt ctaaaaaact caaaagcgtc   3480
aaggaactgc tgggcatcac aatcatggag cgatcaagct tcgaaaaaaa ccccatcgac   3540
tttctcgagg cgaaaggata taagaggtc aaaaaagacc tcatcattaa gcttcccaag   3600
tactctctct ttgagcttga aaacggccgg aaacgaatgc tcgctagtgc gggcgagctg   3660
cagaaaggta acgagctggc actgcccctct aaatacgtta atttcttgta tctgccagcc   3720
cactatgaaa agctcaaagg gtctcccgaa gataatgagc agaagcagct gttcgtggaa   3780
caacacaaac actaccttga tgagatcatc gagcaaataa gcgaattctc caaaagagtg   3840
atcctcgccg acgctaacct cgataaggtg ctttctgctt acaataagca cagggataag   3900
```

```
cccatcaggg agcaggcaga aaacattatc cacttgttta ctctgaccaa cttgggcgcg   3960
cctgcagcct tcaagtactt cgacaccacc atagacagaa agcggtacac ctctacaaag   4020
gaggtcctgg acgccacact gattcatcag tcaattacgg ggctctatga aacaagaatc   4080
gacctctctc agctcggtgg agacagcagg gctgacccca agaagaagag gaaggtgtga   4140
agggtgggcg cgccgaccca gctttcttgt acaaagtggt gatatcccgc ggccatgcta   4200
gagtccgcaa aaatcaccag tctctctcta caaatctatc tctctctatt tttctccaga   4260
ataatgtgtg agtagttccc agataaggga attagggttc ttatagggtt tcgctcatgt   4320
gttgagcata taagaaaccc ttagtatgta tttgtatttg taaaatactt ctatcaataa   4380
aatttctaat tcctaaaacc aaaatccagt gacctgcagg catgcgacgt cgggccctct   4440
agaggatccc cgggtaccgc gaattatcga tcatgagcgg agaattaagg gagtcacgtt   4500
atgacccccg ccgatgacgc gggacaagcc gtttttacgtt tggaactgac agaaccgcaa   4560
cgttgaagga gccactgagc cgcgggtttc tggagtttaa tgagctaagc acatacgtca   4620
gaaaccatta ttgcgcgttc aaaagtcgcc taaggtcact atcagctagc aaatatttct   4680
tgtcaaaaat gctccactga cgttccataa attcccctcg gtatccaatt agagtctcat   4740
attcactctc aactcgatcg aggcatgatt gaacaagatg gattgcacgc aggttctccg   4800
gccgcttggg tggagaggct attcggctat gactgggcac aacagacaat cggctgctct   4860
gatgccgccg tgttccggct gtcagcgcag gggcgcccgg ttcttttttgt caagaccgac   4920
ctgtccggtg ccctgaatga actccaagac gaggcagcgc ggctatcgtg gctggccacg   4980
acgggcgttc cttgcgcagc tgtgctcgac gttgtcactg aagcgggaag ggactggctg   5040
ctattgggcg aagtgccggg gcaggatctc ctgtcatctc accttgctcc tgccgagaaa   5100
gtatccatca tggctgatgc aatgcggcgg ctgcatacgc ttgatccggc tacctgccca   5160
ttcgaccacc aagcgaaaca tcgcatcgag cgagcacgta ctcggatgga agccggtctt   5220
gtcgatcagg atgatctgga cgaagagcat caggggctcg cgccagccga actgttcgcc   5280
aggctcaagg cgcggatgcc cgacggcgag gatctcgtcg tgacccacgg cgatgcctgc   5340
ttgccgaata tcatggtgga aaatggccgc ttttctggat tcatcgactg tggccggctg   5400
ggtgtggcgg accgctatca ggacatagcg ttggctaccc gtgatattgc tgaagagctt   5460
ggcggcgaat gggctgaccg cttcctcgtg ctttacggta tcgccgctcc cgattcgcag   5520
cgcatcgcct tctatcgcct tcttgacgag ttcttctgag cgggactctg gggttcggac   5580
tctagctaga gtcaagcaga tcgttcaaac atttggcaat aaagtttctt aagattgaat   5640
cctgttgccg gtcttgcgat gattatcata taatttctgt tgaattacgt taagcatgta   5700
ataattaaca tgtaatgcat gacgttattt atgagatggg ttttttatgat tagagtcccg   5760
caattataca tttaatacgc gatagaaaac aaaatatagc gcgcaaacta ggataaatta   5820
tcgcgcgcgg tgtcatctat gttactagat cgaccggcat gcaagctgat aattcaattc   5880
ggcgttaatt cagtacatta aaaacgtccg caatgtgtta ttaagttgtc taagcgtcaa   5940
tttgtttaca ccacaatata tcctgccacc agccagccaa cagctccccg accggcagct   6000
cggcacaaaa tcaccactcg atacaggcag cccatcagtc cgggacggcg tcagcgggag   6060
agccgttgta aggcggcaga ctttgctcat gttaccgatg ctattcggaa gaacggcaac   6120
taagctgccg gtttgaaac acggatgatc tcgcggaggg tagcatgttg attgtaacga   6180
tgacagagcg ttgctgcctg tgatcaattc gggcacgaac ccagtggaca taagcctcgt   6240
tcggttcgta agctgtaatg caagtagcgt aactgccgtc acgcaactgg tccagaacct   6300
```

```
tgaccgaacg cagcggtggt aacggcgcag tggcggtttt catggcttct tgttatgaca   6360 tgttttttg gggtacagtc tatgcctcgg gcatccaagc agcaagcgcg ttacgccgtg   6420
ggtcgatgtt tgatgttatg agcagcaac gatgttacgc agcagggcag tcgccctaaa   6480
acaaagttaa acatcatggg ggaagcgtg atcgccgaag tatcgactca actatcagag   6540
gtagttggcg tcatcgagcg ccatctcgaa ccgacgttgc tggccgtaca tttgtacggc   6600
tccgcagtgg atggcggcct gaagccacac agtgatattg atttgctggt tacggtgacc   6660
gtaaggcttg atgaaacaac gcggcgagct ttgatcaacg accttttgga aacttcggct   6720 tccccctggag agagcgagat tctccgcgct gtagaagtca ccattgttgt gcacgacgac   6780
atcattccgt ggcgttatcc agctaagcgc gaactgcaat ttggagaatg cagcgcaat   6840 gacattcttg caggtatctt cgagccagcc acgatcgaca ttgatctggc tatcttgctg   6900
acaaaagcaa gagaacatag cgttgccttg gtaggtccag cggcggagga actctttgat   6960
ccggttcctg aacaggatct atttgaggcg ctaaatgaaa ccttaacgct atggaactcg   7020
ccgcccgact gggctggcga tgagcgaaat gtagtgctta cgttgtcccg catttggtac   7080
agcgcagtaa ccggcaaaat cgcgccgaag gatgtcgctg ccgactgggc aatggagcgc   7140
ctgccggccc agtatcagcc cgtcatactt gaagctagac aggcttatct tggacaagaa   7200
gaagatcgct tggcctcgcg cgcagatcag ttggaagaat ttgtccacta cgtgaaaggc   7260
gagatcacca aggtagtcgg caaataatgt ctagctagaa attcgttcaa gccgacgccg   7320
cttcgccggc gttaactcaa gcgattagat gcactaagca cataattgct cacagccaaa   7380
ctatcaggtc aagtctgctt ttattatttt taagcgtgca taataagccc tacacaaatt   7440
gggagatata tcatgcatga ccaaaatccc ttaacgtgag ttttcgttcc actgagcgtc   7500
agaccccgta gaaaagatca aaggatcttc ttgagatcct ttttttctgc gcgtaatctg   7560
ctgcttgcaa acaaaaaaac caccgctacc agcggtggtt tgtttgccgg atcaagagct   7620
accaactctt tttccgaagg taactggctt cagcagagcg cagataccaa atactgtcct   7680
tctagtgtag ccgtagttag gccaccactt caagaactct gtagcaccgc ctacatacct   7740
cgctctgcta atcctgttac cagtggctgc tgccagtggc gataagtcgt gtcttaccgg   7800
gttggactca agacgatagt taccggataa ggcgcagcgg tcgggctgaa cggggggttc   7860
gtgcacacag cccagcttgg agcgaacgac ctacaccgaa ctgagatacc tacagcgtga   7920
gctatgagaa agcgccacgc ttcccgaagg gagaaaggcg gacaggtatc cggtaagcgg   7980
cagggtcgga acaggagagc gcacgaggga gcttccaggg ggaaacgcct ggtatcttta   8040
tagtcctgtc gggtttcgcc acctctgact tgagcgtcga ttttgtgat gctcgtcagg   8100 ggggcggagc ctatgaaaaa acgccagcaa cgcggccttt ttacggttcc tggccttttg   8160
ctggcctttt gctcacatgt tctttcctgc gttatcccct gattctgtgg ataaccgtat   8220
taccgccttt gagtgagctg ataccgctcg ccgcagccga acgaccgagc gcagcgagtc   8280
agtgagcgag gaagcggaag agcgcctgat gcggtatttt ctccttacgc atctgtgcgg   8340
tatttcacac cgcatatggt gcactctcag tacaatctgc tctgatgccg catagttaag   8400
ccagtataca ctccgctatc gctacgtgac tgggtcatgg ctgcgccccg acacccgcca   8460
acacccgctg acgcgccctg acgggcttgt ctgctcccgg catccgctta cagacaagct   8520
gtgaccgtct ccgggagctg catgtgtcag aggttttcac cgtcatcacc gaaacgcgcg   8580
aggcagggtg ccttgatgtg ggcgccggcg gtcgagtggc gacggcgcgg cttgtccgcg   8640
```

```
ccctggtaga ttgcctggcc gtaggccagc cattttttgag cggccagcgg ccgcgatagg    8700
ccgacgcgaa gcggcgggc gtagggagcg cagcgaccga agggtaggcg ctttttgcag     8760
ctcttcggct gtgcgctggc cagacagtta tgcacaggcc aggcgggttt taagagtttt    8820
aataagtttt aaagagtttt aggcggaaaa atcgcctttt ttctctttta tatcagtcac    8880
ttacatgtgt gaccggttcc caatgtacgg ctttgggttc ccaatgtacg ggttccggtt    8940
cccaatgtac ggctttgggt tcccaatgta cgtgctatcc acaggaaaga gacctttttcg   9000 acctttttcc cctgctaggg caatttgccc tagcatctgc tccgtacatt aggaaccggc    9060
ggatgcttcg ccctcgatca ggttgcggta gcgcatgact aggatcgggc cagcctgccc    9120
cgcctcctcc ttcaaatcgt actccggcag gtcatttgac ccgatcagct tgcgcacggt    9180
gaaacagaac ttcttgaact ctccggcgct gccactgcgt tcgtagatcg tcttgaacaa    9240
ccatctggct tctgccttgc ctgcggcgcg gcgtgccagg cggtagagaa aacggccgat   9300
gccgggatcg atcaaaaagt aatcggggtg aaccgtcagc acgtccgggt tcttgccttc    9360
tgtgatctcg cggtacatcc aatcagctag ctcgatctcg atgtactccg gccgcccggt    9420
ttcgctcttt acgatcttgt agcggctaat caaggcttca ccctcggata ccgtcaccag    9480
gcggccgttc ttggccttct tcgtacgctg catggcaacg tgcgtggtgt ttaaccgaat    9540
gcaggtttct accaggtcgt cttttctgctt tccgccatcg gctcgccggc agaacttgag    9600
tacgtccgca acgtgtggac ggaacacgcg gccgggcttg tctcccttcc cttcccggta    9660
tcggttcatg gattcggtta gatgggaaac cgccatcagt accaggtcgt aatcccacac    9720
actggccatg ccgccggcc ctgcggaaac ctctacgtgc ccgtctggaa gctcgtagcg     9780
gatcacctcg ccagctcgtc ggtcacgctt cgacagacgg aaaacggcca cgtccatgat    9840
gctgcgacta tcgcgggtgc ccacgtcata gagcatcgga acgaaaaaat ctggttgctc    9900
gtcgcccttg gcggcttcc taatcgacgg cgcaccggct gccggcggtt gccgggattc     9960
tttgcggatt cgatcagcgg ccgcttgcca cgattcaccg gggcgtgctt ctgcctcgat   10020
gcgttgccgc tgggcggcct gcgcggcctt caacttctcc accaggtcat cacccagcgc   10080
cgcgccgatt tgtaccgggc cggatggttt gcgaccgtca cgccgattcc tcgggcttgg   10140
gggttccagt gccattgcag ggccggcaga caacccagcc gcttacgcct ggccaaccgc   10200
ccgttcctcc acacatgggg cattccacgg cgtcggtgcc tggttgttct tgattttcca   10260
tgccgcctcc tttagccgct aaaattcatc tactcattta ttcatttgct catttactct    10320
ggtagctgcg cgatgtattc agatagcagc tcggtaatgg tcttgccttg gcgtaccgcg   10380
tacatcttca gcttggtgtg atcctccgcc ggcaactgaa agttgacccg cttcatggct   10440
ggcgtgtctg ccaggctggc caacgttgca gccttgctgc tgcgtgcgct cggacggccg   10500
gcacttagcg tgtttgtgct tttgctcatt ttctctttac ctcattaact caaatgagtt   10560
ttgatttaat ttcagcggcc agcgcctgga cctcgcgggc agcgtcgccc tcgggttctg   10620
attcaagaac ggttgtgccg gcggcggcag tgcctgggta gctcacgcgc tgcgtgatac   10680
gggactcaag aatgggcagc tcgtacccgg ccagcgcctc ggcaacctca ccgccgatgc   10740
gcgtgccttt gatcgcccgc gacacgacaa aggccgcttg tagccttcca tccgtgacct   10800 caatcgctg cttaaccagc tccaccaggt cggcggtggc ccatatgtcg taagggcttg    10860
gctgcaccgg aatcagcacg aagtcggctg ccttgatcgc ggacacagcc aagtccgccg   10920
cctggggcgc tccgtcgatc actacgaagt cgcgccggcc gatggccttc acgtcgcggt   10980
caatcgtcgg gcggtcgatg ccgacaacgg ttagcggttg atcttcccgc acggccgccc   11040
```

```
aatcgcgggc actgccctgg ggatcggaat cgactaacag aacatcggcc ccggcgagtt    11100
gcagggcgcg ggctagatgg gttgcgatgg tcgtcttgcc tgacccgcct ttctggttaa    11160
gtacagcgat aaccttcatg cgttcccctt gcgtatttgt ttatttactc atcgcatcat    11220
atacgcagcg accgcatgac gcaagctgtt ttactcaaat acacatcacc tttttagacg    11280
gcggcgctcg gtttcttcag cggccaagct ggccggccag gccgccagct tggcatcaga    11340
caaaccggcc aggatttcat gcagccgcac ggttgagacg tgcgcgggcg gctcgaacac    11400
gtacccggcc gcgatcatct ccgcctcgat ctcttcggta atgaaaaacg gttcgtcctg    11460
gccgtcctgg tgcggtttca tgcttgttcc tcttggcgtt cattctcggc ggccgccagg    11520
gcgtcggcct cggtcaatgc gtcctcacgg aaggcaccgc gccgcctggc ctcggtgggc    11580
gtcacttcct cgctgcgctc aagtgcgcgg tacagggtcg agcgatgcac gccaagcagt    11640
gcagccgcct ctttcacggt gcggccttcc tggtcgatca gctcgcgggc gtgcgcgatc    11700
tgtgccgggg tgagggtagg gcgggggcca aacttcacgc ctcgggcctt ggcggcctcg    11760
cgcccgctcc gggtgcggtc gatgattagg gaacgctcga actcggcaat gccggcgaac    11820
acggtcaaca ccatgcggcc ggccggcgtg gtggtgtcgg cccacggctc tgccaggcta    11880
cgcaggcccg cgccggcctc ctggatgcgc tcggcaatgt ccagtaggtc gcgggtgctg    11940
cgggccaggc ggtctagcct ggtcactgtc acaacgtcgc cagggcgtag gtggtcaagc    12000
atcctggcca gctccgggcg gtcgcgcctg gtgccggtga tcttctcgga aaacagcttg    12060
gtgcagccgg ccgcgtgcag ttcggcccgt tggttggtca agtcctggtc gtcggtgctg    12120
acgcgggcat agcccagcag gccagcggcg gcgctcttgt tcatggcgta atgtctccgg    12180
ttctagtcgc aagtattcta ctttatgcga ctaaaacacg cgacaagaaa acgccaggaa    12240
aagggcaggg cggcagcctg tcgcgtaact taggacttgt gcgacatgtc gttttcagaa    12300
gacggctgca ctgaacgtca gaagccgact gcactatagc agcggagggg ttggatcaaa    12360
gtactttgat cccgagggga accctgtggt tggcatgcac atacaaatgg acgaacggat    12420
aaaccttttc acgcccttt aaatatccgt tattctaata aacgctcttt tctcttaggt    12480
ttacccgcca atatatcctg tcaaacactg atagtttaaa ctgaaggcgg gaaacgacaa    12540
tctgatccaa gctcaagcta agcttgagct ctcccatatg gtcgactaga gccaagctga    12600
tctcctttgc cccggagatc accatggacg actttctcta tctctacgat ctaggaagaa    12660
agttcgacgg agaaggtgac gataccatgt tcaccaccga taatgagaag attagcctct    12720
tcaatttcag aaagaatgct gacccacaga tggttagaga ggcctacgcg gcaggtctca    12780
tcaagacgat ctacccgagt aataatctcc aggagatcaa ataccttccc aagaaggtta    12840
aagatgcagt caaaagattc aggactaact gcatcaagaa cacagagaaa gatatatttc    12900
tcaagatcag aagtactatt ccagtatgga cgattcaagg cttgcttcat aaaccaaggc    12960
aagtaataga gattggagtc tctaagaaag tagttcctac tgaatcaaag gccatggagt    13020
caaaaattca gatcgaggat ctaacagaac tcgccgtgaa gactggcgaa cagttcatac    13080
agagtctttt acgactcaat gacaagaaga aaatcttcgt caacatggtg gagcacgaca    13140
ctctcgtcta ctccaagaat atcaaagata cagtctcaga agaccaaagg ctattgaga    13200 cttttcaaca aagggtaata tcgggaaacc tcctcggatt ccattgccca gctatctgtc    13260
acttcatcaa aaggacagta gaaaggaag gtggcaccta caaatgccat cattgcgata    13320
aaggaaaggc tatcgttcaa gatgcctctg ccgacagtgg tcccaaagat ggacccccac    13380
```

```
ccacgaggag catcgtggaa aaagaagacg ttccaaccac gtcttcaaag caagtggatt      13440
gatgtgatat ctccactgac gtaagggatg acgcacaatc ccactatcct tcgcaagacc      13500
cttcctctat ataaggaagt tcatttcatt tggagaggac tccggtattt ttacaacaat      13560
accacaacaa aacaaacaac aaacaacatt acaatttact attctagtcg acctgcaggc      13620
ggccgcacta gtatggtgag caagggcgag gagctgttca ccggggtggt gcccatcctg      13680
gtcgagctgg acggcgacgt aaacggccac aagttcagcg tgtccggcga gggcgagggc      13740
gatgccacct acggcaagct gaccctgaag ttcatctgca ccaccggcaa gctgcccgtg      13800
ccctggccca ccctcgtgac caccctgacc tacggcgtgc agtgcttcag ccgctacccc      13860
gaccacatga agcagcacga cttcttcaag tccgccatgc ccgaaggcta cgtccaggag      13920
cgcaccatct tcttcaagga cgacggcaac tacaagaccc gcgccgaggt gaagttcgag      13980
ggcgacaccc tggtgaaccg catcgagctg aagggcatcg acttcaagga ggacggcaac      14040
atcctggggc acaagctgga gtacaactac aacagccaca acgtctatat catggccgac      14100
aagcagaaga acggcatcaa ggtgaacttc aagatccgcc acaacatcga ggacggcagc      14160
gtgcagctcg ccgaccacta ccagcagaac ccccatcg gcgacggccc cgtgctgctg      14220
cccgacaacc actacctgag cacccagtcc gccctgagca agacccccaa cgagaagcgc      14280
gatcacatgg tcctgctgga gttcgtgacc gccgccggga tcactctcgg catggacgag      14340
ctgtacaaga atatcacaag tttgtacaaa aaagcaggct ccgcggccgc ccccttcacc      14400
```

<210> SEQ ID NO 20
<211> LENGTH: 2756
<212> TYPE: DNA
<213> ORGANISM: Artificial sequence
<220> FEATURE:
<223> OTHER INFORMATION: nucleotide sequence of pTRV  2b ribo-DsRed-ribo

<400> SEQUENCE: 20

```
gatccggcgc gccataaaac attgcaccta tggtgttgcc ctggctgggg tatgtcagtg        60
atcgcagtag aatgtactaa ttgacaagtt ggagaatacg gtagaacgtc cttatccaac       120
acagccttta tccctctccc tgacgaggtt tttgtcagtg taatatttct ttttgaacta       180
tccagcttag taccgtacgg gaaagtgact ggtgtgctta tctttgaaat gttactttgg       240
gtttcggttc tttaggttag taagaaagca cttgtcttct catacaaagg aaaacctgag       300
acgtatcgct tacgaaagta gcaatgaaag aaaggtggtg gttttaatcg ctaccgcaaa       360
aacgatgggg tcgttttaat taacttctcc tacgcaagcg tctaaacgga cgttggggtt       420
ttgctagttt cttttagagaa aactagctaa gtctttaatg ttatcattag agatggcata       480
aatataatac ttgtgtctgc tgataagatc attttaattt ggacgattag acttgttgaa       540
ctacaggtta ctgaatcact tgcgctaatc aacaagctta tgggagatat gtacgatgaa       600
tcatttgaca gtcgggcgg tcctgctgac ttgatgacg attcttgggt ggaatcagtt       660
tcgtggaaag atctgttgaa gaagttacac agcataaaat ttgcactaca gtctggtaga       720
gatgagatca ctgggttact agcggcactg aatagacagt gtccttattc accatatgag       780
cagtttccag ataagaaggt gtatttcctt ttagactcac gggctaacag tgctcttggt       840
gtgattcaga acgcttcagc gttcaagaga cgagctgatg agaagaatgc agtggcgggt       900
gttacaaata ttcctgcgaa tccaaacaca acgttacga cgaaccaagg gagtactact       960
actaccaagg cgaacactgg ctcgactttg aagaagact tgtacactta ttacaaattc      1020
gatgatgcct ctacagcttt ccacaaatct ctaacttcgt tagagaacat ggagttgaag      1080
```

```
agttattacc gaaggaactt tgagaaagta ttcgggatta agtttggtgg agcagctgct    1140
agttcatctg caccgcctcc agcgagtgga ggtccgatac gtcctaatcc ctagggattt    1200
aaggacgtga actctgttga gatctctgtg aaattcagag ggtgggtgat accatattca    1260
ctgatgccat tagcgacatc taaatagggc taattgtgac taatttgagg gaatttcctt    1320
taccattgac gtcagtgtcg ttggtagcat ttgagtttcg taactataac ggtcctaagg    1380
tagcgaacat cttgttctgg ggtttcacac tatctttaga gaaagtgtta agttaattaa    1440
gttatcttaa ttaagagcat aattatactg atttgtctct cgttgataga gtctatcatt    1500
ctgttactaa aaatttgaca actcggtttg ctgacctact ggttactgta tcacttaccc    1560
gagttaacga gggccatctg atgagtccgt gaggacgaaa cgagtaagct cgtcatggcc    1620
tcctccgaga acgtcatcac cgagttcatg cgcttcaagg tgcgcatgga gggcaccgtg    1680
aacggccacg agttcgagat cgagggcgag ggcgagggcc gcccctacga gggccacaac    1740
accgtgaagc tgaaggtgac caagggcggc cccctgccct tcgcctggga catcctgtcc    1800
ccccagttcc agtacggctc caaggtgtac gtgaagcacc ccgccgacat ccccgactac    1860
aagaagctgt ccttccccga gggcttcaag tgggagcgcg tgatgaactt cgaggacggc    1920
ggcgtggcga ccgtgaccca ggactcctcc ctgcaggacg gctgcttcat ctacaaggtg    1980
aagttcatcg gcgtgaactt cccctccgac ggccccgtga tgcagaagaa gaccatgggc    2040
tgggaggcct ccaccgagcg cctgtacccc cgcgacggcg tgctgaaggg cgagacccac    2100
aaggccctga gctgaagga cggcggccac tacctggtgg agttcaagtc catctacatg    2160
gccaagaagc ccgtgcagct gcccggctac tactacgtgg acgccaagct ggacatcacc    2220
tcccacaacg aggactacac catcgtggag cagtacgagc gcaccgaggg ccgccaccac    2280
ctgttcctgt gaggccggca tggtcccagc ctcctcgctg gcgccggctg ggcaacatgc    2340
ttcggcatgg cgaatgggac gtcgaccccg aagacattaa actacggttc tttaagtaga    2400
tccgtgtctg aagtttaggt tcaatttaaa cctacgagat tgacattctc gactgatctt    2460
gattgatcgg taagtctttt gtaatttaat tttcttttg attttatttt aaattgttat    2520
ctgtttctgt gtatagactg tttgagatcg gcgtttggcc gactcattgt cttaccatag    2580
gggaacggac tttgtttgtg ttgttatttt atttgtattt tattaaaatt ctcaacgatc    2640
tgaaaaagcc tcgcggctaa gagattgttg gggggtgagt aagtacttt aaagtgatga    2700 tggttacaaa ggcaaagggg gtaaaacccc tcgcctacgt aagcgttatt acgccc       2756
```

<210> SEQ ID NO 21
<211> LENGTH: 214
<212> TYPE: DNA
<213> ORGANISM: Artificial sequence
<220> FEATURE:
<223> OTHER INFORMATION: nucleotide sequence of RGR1RGR1

<400> SEQUENCE: 21

```
ggccatctga tgagtccgtg aggacgaaac gagtaagctc gtcgctgtca gcgcaggggc      60
gccgttttag agctagaaat agcaagttaa aataaggcta gtccgttatc aacttgaaaa    120
agtggcaccg agtcggtgct ttttttggcc ggcatggtcc cagcctcctc gctggcgccg    180
gctgggcaac atgcttcggc atggcgaatg ggac                                 214
```

<210> SEQ ID NO 22
<211> LENGTH: 214
<212> TYPE: DNA

```
<213> ORGANISM: Artificial sequence
<220> FEATURE:
<223> OTHER INFORMATION: nucleotide sequence of RGR2

<400> SEQUENCE: 22
ggccatctga tgagtccgtg aggacgaaac gagtaagctc gtcgccgtta atttgagagt      60
ccagttttag agctagaaat agcaagttaa ataaggcta gtccgttatc aacttgaaaa      120
agtggcaccg agtcggtgct ttttttggcc ggcatggtcc cagcctcctc gctggcgccg    180
gctgggcaac atgcttcggc atggcgaatg ggac                                  214

<210> SEQ ID NO 23
<211> LENGTH: 202
<212> TYPE: DNA
<213> ORGANISM: Artificial sequence
<220> FEATURE:
<223> OTHER INFORMATION: nucleotide sequence of CP subgenomic promoter

<400> SEQUENCE: 23
cgttttaatt aacttctcct acgcaagcgt ctaaacggac gttggggttt tgctagtttc     60
tttagagaaa actagctaag tctttaatgt tatcattaga gatggcataa atataatact   120
tgtgtctgct gataagatca ttttaatttg gacgattaga cttgttgaac tacaggttac   180
tgaatcactt gcgctaatca ac                                              202

<210> SEQ ID NO 24
<211> LENGTH: 253
<212> TYPE: DNA
<213> ORGANISM: Artificial sequence
<220> FEATURE:
<223> OTHER INFORMATION: nucleotide sequence of NOS terminator

<400> SEQUENCE: 24
agtttcttaa gattgaatcc tgttgccggt cttgcgatga ttatcatata atttctgttg    60
aattacgtta agcatgtaat aattaacatg taatgcatga cgttatttat gagatgggtt   120
tttatgatta gagtcccgca attatacatt taatacgcga tagaaaacaa aatatagcgc   180
gcaaactagg ataaattatc gcgcgcggtg tcatctatgt tactagatcg ggaattaaac   240
tatcagtgtt tga                                                        253

<210> SEQ ID NO 25
<211> LENGTH: 70
<212> TYPE: DNA
<213> ORGANISM: Artificial sequence
<220> FEATURE:
<223> OTHER INFORMATION: nucleotide sequence of omega enhancer

<400> SEQUENCE: 25
gtatttttac aacaattacc aacaacaaca acaacagac aacattacaa ttactattta     60
caattacaat                                                             70

<210> SEQ ID NO 26
<211> LENGTH: 24
<212> TYPE: DNA
<213> ORGANISM: Artificial sequence
<220> FEATURE:
<223> OTHER INFORMATION: nucleotide sequence of qqr

<400> SEQUENCE: 26
ttcttcccct cctgagggga agaa                                            24
```

<210> SEQ ID NO 27
<211> LENGTH: 1065
<212> TYPE: DNA
<213> ORGANISM: Artificial sequence
<220> FEATURE:
<223> OTHER INFORMATION: nucleotide sequence of full length 2b

<400> SEQUENCE: 27

```
atgcacgaat tacttaggaa gtggcttgac gacactaatg tgttattgtt agataatggt        60
ttggtggtca aggtacgtag tagagtccca catattcgca cgtatgaagt aattggaaag       120
ttgtcagttt ttgataattc actgggagat gatacgctgt tgagggaaa gtagagaac         180
gtatttgttt ttatgttcag gcggttcttg tgtgtcaaca agatggaca ttgttactca        240
aggaagcacg atgagcttta ttattacgga cgagtggact tagattctgt gagtaaggtt       300
acctcagggt acgagaaact ctttattcac agagaacttt atatcttaac agatttaatt       360
gagagagtga gtaagttctt taacttagct caggatgtgg tagaagcaag ttttgagtat       420
gccaaggttg aagagaggtt aggtcacgtc agaaacgtgt tgcaactggc gggtggaaaa       480
tccacgaatg ccgatttgac aattaagatt tctgacgatg tcgaacaact gcttggaaaa       540
cgtggtggat tcttgaaggt tgtgaacggt atcttgagca agaatggtag tgacgtagtc       600
actaacgaca atgagcttat tcatgcaatt aaccaaaatc tggtaccaga taaagtcatg       660
tctgtgtcga acgtaatgaa agagactggg ttttctgcagt ttccaaagtt tttatctaag       720
ttggaaggac aggtaccgaa aggaacaaaa tttctagaca aacacgttcc tgattttact       780
tggatacaag ctcttgaaga aagagtgaat attcggagag gagaatcggg acttcagact       840
ctattagctg atatcgttcc gaggaatgct attgctgctc agaaattgac aatgctaggt       900
tacatcgagt atcacgacta tgtggtgatc gtctgtcagt ctggagtatt tagtgacgat       960
tgggcgacat gtagaatgct ttgggcagca ctatctagtg ctcaactata tacctatgtt      1020
gacgccagta gaatcggtcc aatcgtttac ggttggttat tgtga                      1065
```

<210> SEQ ID NO 28
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 28

```
gtctgccagt tcagttcgtt gttc                                               24
```

<210> SEQ ID NO 29
<211> LENGTH: 73
<212> TYPE: DNA
<213> ORGANISM: Artificial sequence
<220> FEATURE:
<223> OTHER INFORMATION: nucleotide sequence of the target site detected
      in the N. benthamiana target genes NptII

<400> SEQUENCE: 29

```
atgccgccgt gttccggctg tcagcgcagg ggcgcccggt tctttttgtc aagaccgacc        60
tgtccggtgc cct                                                           73
```

<210> SEQ ID NO 30
<211> LENGTH: 65
<212> TYPE: DNA
<213> ORGANISM: Artificial sequence
<220> FEATURE:
<223> OTHER INFORMATION: nucleotide sequence of the target site detected in the N. benthamiana target genes NptII with -8bp indel.

<400> SEQUENCE: 30
atgccgccgt gttccggctg tcagcgcccg gttctttttg tcaagaccga cctgtccggt    60
gccct    65

<210> SEQ ID NO 31
<211> LENGTH: 65
<212> TYPE: DNA
<213> ORGANISM: Artificial sequence
<220> FEATURE:
<223> OTHER INFORMATION: nucleotide sequence of the target site detected
      in the N. benthamiana target genes NptII with -8bp indel.

<400> SEQUENCE: 31
atgccgccgt gttccggctg tcagcgcacg gttctttttg tcaagaccga cctgtccggt    60
gccct    65

<210> SEQ ID NO 32
<211> LENGTH: 71
<212> TYPE: DNA
<213> ORGANISM: Artificial sequence
<220> FEATURE:
<223> OTHER INFORMATION: nucleotide sequence of the target site detected
      in the N. benthamiana target genes NptII with -2bp indel.

<400> SEQUENCE: 32
atgccgccgt gttccggctg tcagcgcagg ggcccggttc tttttgtcaa gaccgacctg    60
tccggtgccc t    71

<210> SEQ ID NO 33
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes NptII with +1bp indel.

<400> SEQUENCE: 33
atgccgccgt gttccggctg tcagcgcagg ggctgcccgg ttctttttgt caagaccgac    60
ctgtccggtg ccct    74

<210> SEQ ID NO 34
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes NptII with +1bp indel.

<400> SEQUENCE: 34
atgccgccgt gttccggctg tcagcgcagg ggctgcccgg ttctttttgt caagaccgac    60
ctgtccggtg ccct    74

<210> SEQ ID NO 35
<211> LENGTH: 63
<212> TYPE: DNA
<213> ORGANISM: Artificial sequence
<220> FEATURE:
<223> OTHER INFORMATION: nucleotide sequence of the target site detected
      in the N. benthamiana target genes NptII with -10bp indel.

<400> SEQUENCE: 35

```
atgccgccgt gttccggctg tccgcccggt tcttttttgtc aagaccgacc tgtccggtgc      60
cct                                                                    63

<210> SEQ ID NO 36
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes NptII with +1bp indel.

<400> SEQUENCE: 36
atgccgccgt gttccggctg tcagcgcagg ggctgcccgg ttcttttgt caagaccgac       60 ctgtccggtg ccct                                                        74

<210> SEQ ID NO 37
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes NptII with +1bp indel.

<400> SEQUENCE: 37
atgccgccgt gttccggctg tcagcgcagg ggcagcccgg ttcttttgt caagaccgac       60 ctgtccggtg ccct                                                        74

<210> SEQ ID NO 38
<211> LENGTH: 72
<212> TYPE: DNA
<213> ORGANISM: Artificial sequence
<220> FEATURE:
<223> OTHER INFORMATION: nucleotide sequence of the target site detected
      in the N. benthamiana target genes NptII with -1bp indel.

<400> SEQUENCE: 38
atgccgccgt gttccggctg tcagcgcagg gggcccggtt cttttgtca agaccgacct       60 gtccggtgcc ct                                                          72

<210> SEQ ID NO 39
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes NptII with +1bp indel.

<400> SEQUENCE: 39
atgccgccgt gttccggctg tcagcgcagg ggcagcccgg ttcttttgt caagaccgac       60 ctgtccggtg ccct                                                        74

<210> SEQ ID NO 40
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes NptII with +1bp indel.

<400> SEQUENCE: 40
atgccgccgt gttccggctg tcagcgcagg ggccgcccgg ttcttttgt caagaccgac       60 ctgtccggtg ccct                                                        74
```

<210> SEQ ID NO 41
<211> LENGTH: 65
<212> TYPE: DNA
<213> ORGANISM: Artificial sequence
<220> FEATURE:
<223> OTHER INFORMATION: nucleotide sequence of the target site detected
      in the N. benthamiana target genes NptII with -8bp indel.

<400> SEQUENCE: 41
atgccgccgt gttccggctg tcagcgcccg gttcttttg tcaagaccga cctgtccggt      60
gccct                                                                  65

<210> SEQ ID NO 42
<211> LENGTH: 73
<212> TYPE: DNA
<213> ORGANISM: Artificial sequence
<220> FEATURE:
<223> OTHER INFORMATION: nucleotide sequence of the target site detected
      in the N. benthamiana target genes PDS

<400> SEQUENCE: 42
taaaatgccc caaattggac ttgtttctgc cgttaatttg agagtccaag gtaattcagc      60
ttatctttgg agc                                                         73

<210> SEQ ID NO 43
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes PDS with +1bp indel.

<400> SEQUENCE: 43
taaaatgccc caaattggac ttgtttctgc cgttaatttg agagttccaa ggtaattcag      60
cttatctttg gagc                                                        74

<210> SEQ ID NO 44
<211> LENGTH: 74
<212> TYPE: DNA
<213> ORGANISM: Artificial sequence
<220> FEATURE:
<223> OTHER INFORMATION: nucleotide sequence of the target site detected
      in the N. benthamiana target genes PDS with +1bp indel.

<400> SEQUENCE: 44
taaaatgccc caaattggac ttgtttctgc cgttaatttg agagttccaa ggtaattcag      60
cttatctttg gagc                                                        74

<210> SEQ ID NO 45
<211> LENGTH: 70
<212> TYPE: DNA
<213> ORGANISM: Artificial sequence
<220> FEATURE:
<223> OTHER INFORMATION: nucleotide sequence of the target site detected
      in the N. benthamiana target genes PDS with -3bp indel.

<400> SEQUENCE: 45
taaaatgccc caaattggac ttgtttctgc cgttaatttg agccaaggta attcagctta      60
tctttggagc                                                             70

<210> SEQ ID NO 46
<211> LENGTH: 73
<212> TYPE: DNA

<213> ORGANISM: Artificial sequence
<220> FEATURE:
<223> OTHER INFORMATION: nucleotide sequence of a fragment of the mGUS gene, targeted by the pTRV2 -QQR-sgRNA

<400> SEQUENCE: 46

```
ctgcagtcga cggtaccatg ttcttcccct cctgagggga agaattacgt cctgtagaaa    60
ccccaacccg tga                                                       73
```

<210> SEQ ID NO 47
<211> LENGTH: 69
<212> TYPE: DNA
<213> ORGANISM: Artificial sequence
<220> FEATURE:
<223> OTHER INFORMATION: nucleotide sequence of a fragment of the mGUS gene, targeted by the pTRV2 -QQR-sgRNA with -4bp indel.

<400> SEQUENCE: 47

```
ctgcagtcga cggtaccatg ttcttcccct cggggaagaa ttacgtcctg tagaaacccc    60
aacccgtga                                                            69
```

<210> SEQ ID NO 48
<211> LENGTH: 73
<212> TYPE: DNA
<213> ORGANISM: Artificial sequence
<220> FEATURE:
<223> OTHER INFORMATION: nucleotide sequence of a fragment of the mGUS gene, targeted by the pTRV2 -QQR-sgRNA with +1bp indel.

<400> SEQUENCE: 48

```
ctgcagtcga cggtaccatg ttcttcccct ccagagggga agaattacgt cctgtagaaa    60
ccccaacccg tga                                                       73
```

<210> SEQ ID NO 49
<211> LENGTH: 1593
<212> TYPE: DNA
<213> ORGANISM: Artificial sequence
<220> FEATURE:
<223> OTHER INFORMATION: nucleotide sequence of TRV RNA2-CP-sgNptII-k-sgNptII-i

<400> SEQUENCE: 49

```
cattgcacct atggtgttgc cctggctggg gtatgtcagt gatcgcagta gaatgtacta    60
attgacaagt tggagaatac ggtagaacgt ccttatccaa cacagccttt atccctctcc   120
ctgacgaggt ttttgtcagt gtaatatttc tttttgaact atccagctta gtaccgtacg   180
ggaaagtgac tggtgtgctt atctttgaaa tgttactttg ggtttcggtt ctttaggtta   240
gtaagaaagc acttgtcttc tcatacaaag gaaaacctga gacgtatcgc ttacgaaagt   300
agcaatgaaa gaaaggtggt ggttttaatc gctaccgcaa aaacgatggg gtcgttttaa   360
ttaacttctc ctacgcaagc gtctaaacgg acgttggggt tttgctagtt tctttagaga   420
aaactagcta agtctttaat gttatcatta gagatggcat aaatataata cttgtgtctg   480
ctgataagat cattttaatt tggacgatta gacttgttga actacaggtt actgaatcac   540
ttgcgctaat caacaagctt aaaagcttgt taacgaggct gtcagcgcag gggcgccgtt   600
ttagagctag aaatagcaag ttaaataag gctagtccgt tatcaacttg aaaaagtggc   660
accgagtcgg tgcttttttt ctcgagggat ttaaggacgt gaactctgtt gagatctctg   720
tgaaattcag agggtgggtg ataccatatt cactgatgcc attagcgaca tctaaatagg   780
gctaattgtg actaatttga gggaatttcc tttaccattg acgtcagtgt cgttggtagc   840
```

```
atttgagttt cgtaactata acggtcctaa ggtagcgaac atcttgttct ggggtttcac      900
actatcttta gagaaagtgt taagttaatt aagttatctt aattaagagc ataattatac      960
tgatttgtct ctcgttgata gagtctatca ttctgttact aaaaatttga caactcggtt     1020
tgctgaccta ctggttactg tatcacttac ccgagttaac gaggctcgac gttgtcactg     1080
aaggttttag agctagaaat agcaagttaa aataaggcta gtccgttatc aacttgaaaa     1140
agtggcaccg agtcggtgct ttttttctcg agcccgggta gggataacag ggtaatgtcg     1200
accccgaaga cattaaacta cggttcttta agtagatccg tgtctgaagt tttaggttca     1260
atttaaacct acgagattga cattctcgac tgatcttgat tgatcggtaa gtcttttgta     1320
atttaatttt cttttttgatt ttattttaaa ttgttatctg tttctgtgta tagactgttt     1380
gagatcggcg tttggccgac tcattgtctt accataggg aacggacttt gtttgtgttg      1440
ttattttatt tgtattttat taaaattctc aacgatctga aaaagcctcg cggctaagag     1500
attgttgggg ggtgagtaag tacttttaaa gtgatgatgg ttacaaaggc aaaagggta      1560
aaaccccctcg cctacgtaag cgttattacg ccc                                 1593
```

<210> SEQ ID NO 50
<211> LENGTH: 2308
<212> TYPE: DNA
<213> ORGANISM: Artificial sequence
<220> FEATURE:
<223> OTHER INFORMATION: nucleotide sequence of TRV RNA2-CP-sgNptII-i-
      sgNptII-kDsRed2

<400> SEQUENCE: 50

```
cattgcacct atggtgttgc cctggctggg gtatgtcagt gatcgcagta gaatgtacta       60
attgacaagt tggagaatac ggtagaacgt ccttatccaa cacagccttt atccctctcc      120
ctgacgaggt ttttgtcagt gtaatatttc ttttttgaact atccagctta gtaccgtacg     180
ggaaagtgac tggtgtgctt atctttgaaa tgttactttg ggtttcggtt ctttaggtta     240
gtaagaaagc acttgtcttc tcatacaaag gaaaacctga gacgtatcgc ttacgaaagt     300
agcaatgaaa gaaaggtggt ggttttaatc gctaccgcaa aaacgatggg gtcgttttaa     360
ttaacttctc ctacgcaagc gtctaaacgg acgttggggt tttgctagtt tcttagaga     420
aaactagcta agtcttttaat gttatcatta gagatggcat aaatataata cttgtgtctg     480
ctgataagat catttaaatt tggacgatta gacttgttga actacaggtt actgaatcac     540
ttgcgctaat caacaagctg taaagcttgt taacgaggct cgacgttgtc actgaaggtt     600
ttagagctag aaatagcaag ttaaaataag gctagtccgt tatcaacttg aaaaagtggc     660
accgagtcgg tgctttttt tctcgagttttt tcagcaagat ctcgaggacg tcagtgtcgt     720
tggtagcatt tgagtttcgg ctgtcagcgc aggggcgccg ttttagagct agaaatagca     780
agttaaaata aggctagtcc gttatcaact tgaaaaagtg gcaccgagtc ggtgcttttt     840
ttcctaagga tttaaggacg tgaactctgt tgagatctct gtgaaattca gagggtgggt     900
gataccatat tcactgatgc cattagcgac atctaaatag gctaattgt gactaatttg     960
agggaatttc ctttaccatt gacgtcagtg tcgttggtag catttgagtt tcgtaactat    1020
aacggtccta aggtagcgaa catcttgttc tggggtttca cactatcttt agagaaagtg    1080
ttaagttaat taagttatct taattaagag cataattata ctgatttgtc tctcgttgat    1140
agagtctatc attctgttac taaaaatttg acaactcggt tgctgaccta ctggttact    1200
gtatcactta cccgagttaa cgagatggcc tcctccgaga acgtcatcac cgagttcatg    1260
```

```
cgcttcaagg tgcgcatgga gggcaccgtg aacggccacg agttcgagat cgagggcgag    1320
ggcgagggcc gccCCtacga gggccacaac accgtgaagc tgaaggtgac caagggcggc    1380
cccctgccct tcgcctggga catcctgtcc ccccagttcc agtacggctc caaggtgtac    1440
gtgaagcacc ccgccgacat ccccgactac aagaagctgt ccttccccga gggcttcaag    1500
tgggagcgcg tgatgaactt cgaggacggc ggcgtggcga ccgtgaccca ggactcctcc    1560
ctgcaggacg gctgcttcat ctacaaggtg aagttcatcg gcgtgaactt ccctccgac     1620 ggccccgtga tgcagaagaa gaccatgggc tgggaggcct ccaccgagcg cctgtacccc    1680 cgcgacggc tgctgaaggg cgagacccac aaggccctga gctgaagga cggcggccac     1740 tacctggtgg agttcaagtc catctacatg gccaagaagc ccgtgcagct gcccggctac    1800
tactacgtgg acgccaagct ggacatcacc tcccacaacg aggactacac catcgtggag    1860
cagtacgagc gcaccgaggg ccgccaccac ctgttcctgt gagtcgaccg gcatgtccc    1920 gaagacatta aactacggtt ctttaagtag atccgtgtct gaagttttag gttcaattta    1980
aacctacgag attgacattc tcgactgatc ttgattgatc ggtaagtctt ttgtaattta    2040
attttctttt tgattttatt ttaaattgtt atctgtttct gtgtatagac tgtttgagat    2100
cggcgtttgg ccgactcatt gtcttaccat aggggaacgg actttgtttg tgttgttatt    2160
ttatttgtat tttattaaaa ttctcaacga tctgaaaaag cctcgcggct aagagattgt    2220 tgggggtga gtaagtactt ttaaagtgat gatggttaca aaggcaaaag gggtaaaacc     2280
cctcgcctac gtaagcgtta ttacgccc                                       2308
```

<210> SEQ ID NO 51
<211> LENGTH: 2237
<212> TYPE: DNA
<213> ORGANISM: Artificial sequence
<220> FEATURE:
<223> OTHER INFORMATION: nucleotide sequence of TRV RNA2-CP-sgNptII-i-
      sgNptII-kDsRed2

<400> SEQUENCE: 51

```
cattgcacct atggtgttgc cctggctggg gtatgtcagt gatcgcagta gaatgtacta     60
attgacaagt tggagaatac ggtagaacgt ccttatccaa cacagccttt atccctctcc    120
ctgacgaggt ttttgtcagt gtaatatttc ttttgaact atccagctta gtaccgtacg    180
ggaaagtgac tggtgtgctt atctttgaaa tgttactttg ggtttcggtt ctttaggtta    240
gtaagaaagc acttgtcttc tcatacaaag gaaaacctga gacgtatcgc ttacgaaagt    300
agcaatgaaa gaaggtggt ggttttaatc gctaccgcaa aaacgatggg gtcgttttaa    360
ttaacttctc ctacgcaagc gtctaaacgg acgttggggt tttgctagtt tctttagaga    420
aaactagcta agtctttaat gttatcatta gagatgcat aaatataata cttgtgtctg     480
ctgataagat cattttaatt tggacgatta gacttgttga actacaggtt actgaatcac    540
ttgcgctaat caacaagctg taaagcttgt taacgaggct cgacgttgtc actgaaggtt    600
ttagagctag aaatagcaag ttaaaataag gctagtccgt tatcaacttg aaaaagtggc    660
accgagtcgg tgctttttttt ctcgagggat ttaaggacgt gaactctgtt gagatctctg    720
tgaaattcag agggtgggtg ataccatatt cactgatgcc attagcgaca tctaaatagg    780
gctaattgtg actaatttga gggaattcc tttaccattg acgtcagtgt cgttggtagc    840
atttgagttt cggctgtcag cgcagggcg ccgtttaga gctagaaata gcaagttaaa    900
ataaggctag tccgttatca acttgaaaaa gtggcaccga gtcggtgctt ttttttcctaa    960
```

```
ggtagcgaac atcttgttct ggggtttcac actatcttta gagaaagtgt taagttaatt   1020
aagttatctt aattaagagc ataattatac tgatttgtct ctcgttgata gagtctatca   1080
ttctgttact aaaaatttga caactcggtt tgctgaccta ctggttactg tatcacttac   1140
ccgagttaac gagatggcct cctccgagaa cgtcatcacc gagttcatgc gcttcaaggt   1200
gcgcatggag ggcaccgtga acggccacga gttcgagatc gagggcgagg gcgagggccg   1260
cccctacgag ggccacaaca ccgtgaagct gaaggtgacc aagggcggcc ccctgccctt   1320
cgcctgggac atcctgtccc cccagttcca gtacggctcc aaggtgtacg tgaagcaccc   1380
cgccgacatc cccgactaca agaagctgtc cttccccgag ggcttcaagt gggagcgcgt   1440
gatgaacttc gaggacggcg gcgtggcgac cgtgacccag gactcctccc tgcaggacgg   1500
ctgcttcatc tacaaggtga agttcatcgg cgtgaacttc ccctccgacg gccccgtgat   1560
gcagaagaag accatgggct gggaggcctc caccgagcgc ctgtaccccc gcgacggcgt   1620
gctgaagggc gagacccaca aggccctgaa gctgaaggac ggcggccact acctggtgga   1680
gttcaagtcc atctacatgg ccaagaagcc cgtgcagctg cccggctact actacgtgga   1740
cgccaagctg gacatcacct cccacaacga ggactacacc atcgtggagc agtacgagcg   1800
caccgagggc cgccaccacc tgttcctgtg agtcgaccgg gcatgtcccg aagacattaa   1860
actacggttc tttaagtaga tccgtgtctg aagttttagg ttcaatttaa acctacgaga   1920
ttgacattct cgactgatct tgattgatcg gtaagtcttt tgtaatttaa ttttcttttt   1980
gattttattt taaattgtta tctgtttctg tgtatagact gtttgagatc ggcgtttggc   2040
cgactcattg tcttaccata ggggaacgga ctttgtttgt gttgttattt tatttgtatt   2100
ttattaaaat tctcaacgat ctgaaaaagc ctcgcggcta agagattgtt ggggggtgag   2160
taagtacttt taaagtgatg atggttacaa aggcaaaagg ggtaaaaccc ctcgcctacg   2220
taagcgttat tacgccc                                                  2237

<210> SEQ ID NO 52
<211> LENGTH: 2053
<212> TYPE: DNA
<213> ORGANISM: Artificial sequence
<220> FEATURE:
<223> OTHER INFORMATION: nucleotide sequence of TRV RNA2-CP-sgNptII-i-
      sgNptII-kDsRed2

<400> SEQUENCE: 52
cataaaacat tgcacctatg gtgttgccct ggctggggta tgtcagtgat cgcagtagaa     60
tgtactaatt gacaagttgg agaatacggt agaacgtcct tatccaacac agcctttatc    120
cctctccctg acgaggtttt tgtcagtgta atatttcttt ttgaactatc cagcttagta    180
ccgtacggga aagtgactgg tgtgcttatc tttgaaatgt tactttgggt ttcggttctt    240
taggttagta agaaagcact tgtcttctca tacaaaggaa aacctgagac gtatcgctta    300
cgaaagtagc aatgaaagaa aggtggtggt tttaatcgct accgcaaaaa cgatgggggtc   360 gtttttaatta acttctccta cgcaagcgtc taaacggacg ttgggggtttt gctagtttct   420 ttagagaaaa ctagctaagt ctttaatgtt atcattagag atggcataaa tataatactt    480
gtgtctgctg ataagatcat tttaatttgg acgattagac ttgttgaact acaggttact    540
gaatcacttg cgctaatcaa caagctgtaa agcttgttaa cgaggctcga cgttgtcact    600
gaaggtttta gagctagaaa tagcaagtta aaataaggct agtccgttat caacttgaaa    660
aagtggcacc gagtcggtgc tttttttctc gagggattta aggacgtgaa ctctgttgag    720
```

```
atctctgtga aattcagagg gtgggtgata ccatattcac tgatgccatt agcgacatct    780
aaatagggct aattgtgact aatttgaggg aatttccttt accattgacg tcagtgtcgt    840
tggtagcatt tgagtttcgg ctgtcagcgc aggggcgccg ttttagagct agaaatagca    900
agttaaaata aggctagtcc gttatcaact tgaaaaagtg caccgagtc ggtgcttttt     960 ttcctaagga tggcctcctc cgagaacgtc atcaccgagt tcatgcgctt caaggtgcgc   1020
atggagggca ccgtgaacgg ccacgagttc gagatcgagg gcgagggcga gggccgcccc   1080
tacgagggcc acaacaccgt gaagctgaag gtgaccaagg gcggcccct gcccttcgcc    1140 tgggacatcc tgtccccca gttccagtac ggctccaagg tgtacgtgaa gcaccccgcc    1200
gacatccccg actacaagaa gctgtccttc cccgagggct tcaagtggga gcgcgtgatg   1260
aacttcgagg acggcggcgt ggcgaccgtg acccaggact cctccctgca ggacggctgc   1320
ttcatctaca aggtgaagtt catcggcgtg aacttcccct ccgacggccc cgtgatgcag   1380
aagaagacca tgggctggga ggcctccacc gagcgcctgt accccgcga cggcgtgctg   1440 aagggcgaga cccacaaggc cctgaagctg aaggacggcg ccactacct ggtggagttc    1500 aagtccatct acatggccaa gaagcccgtg cagctgcccg gctactacta cgtggacgcc   1560
aagctggaca tcacctccca caacgaggac tacaccatcg tggagcagta cgagcgcacc   1620
gagggccgcc accacctgtt cctgtgagtc gaccgggcat gtcccgaaga cattaaacta   1680
cggttcttta agtagatccg tgtctgaagt tttaggttca atttaaacct acgagattga   1740
cattctcgac tgatcttgat tgatcggtaa gtcttttgta atttaattttt ctttttgatt   1800 ttatttaaaa ttgttatctg tttctgtgta tagactgttt gagatcggcg tttggccgac   1860
tcattgtctt accataggg aacggactttt gtttgtgttg ttatttttatt tgtattttat   1920 taaaattctc aacgatctga aaaagcctcg cggctaagag attgttgggg ggtgagtaag   1980
tacttttaaa gtgatgatgg ttacaaaggc aaaagggta aaaccccctcg cctacgtaag    2040 cgttattacg ccc                                                       2053

<210> SEQ ID NO 53
<211> LENGTH: 103
<212> TYPE: DNA
<213> ORGANISM: Artificial sequence
<220> FEATURE:
<223> OTHER INFORMATION: nucleotide sequence of nptII(i)-sgRNA

<400> SEQUENCE: 53
gctcgacgtt gtcactgaag gttttagagc tagaaatagc aagttaaaat aaggctagtc    60
cgttatcaac ttgaaaaagt ggcaccgagt cggtgctttt ttt                      103

<210> SEQ ID NO 54
<211> LENGTH: 5414
<212> TYPE: DNA
<213> ORGANISM: Artificial sequence
<220> FEATURE:
<223> OTHER INFORMATION: nucleotide sequence of a T-DNA with mGUS and
      nptII cassettes

<400> SEQUENCE: 54
gtttacccgc caatatatcc tgtcaaacac tgatagttta aactgaaggc gggaaacgac    60
aatctgatcc aagctcaagc taagcttagg cctgtcgacg cccgggcggt accgcgatcg   120
ctcgcgacct gcaggcataa agccgtcagt gtccgcataa agaaccaccc ataataccca   180
taatagctgt ttgccaaccg gtcaacatgt ggagcacgac acacttgtct actccaaaaa   240
```

```
tatcaaagat acagtctcag aagaccaaag ggcaattgag acttttcaac aaagggtaat      300
atccggaaac ctcctcggat tccattgccc agctatctgt cactttattg tgaagatagt      360
ggaaaaggaa ggtggctcct acaaatgcca tcattgcgat aaaggaaagg ccatcgttga      420
agatgcctct gccgacagtg gtcccaaaga tggaccccca cccacgagga gcatcgtgga      480
aaaagaagac gttccaacca cgtcttcaaa gcaagtggat tgatgtgata acatggtgga      540
gcacgacaca cttgtctact ccaaaaatat caaagataca gtctcagaag accaaagggc      600
aattgagact tttcaacaaa gggtaatatc cggaaacctc ctcggattcc attgcccagc      660
tatctgtcac tttattgtga agatagtgga aaggaaggt ggctcctaca aatgccatca      720
ttgcgataaa ggaaaggcca tcgttgaaga tgcctctgcc gacagtggtc caaagatgg      780 acccccaccc acgaggagca tcgtggaaaa agaagacgtt ccaaccacgt cttcaaagca      840
agtggattga tgtgatatct ccactgacgt aagggatgac gcacaatccc actatccttc      900
gcaagaccct tcctctatat aaggaagttc atttcatttg gagaggacgt cgagagttct      960
caacacaaca tatacaaaac aaacgaatct caagcaatca agcattctac ttctattgca     1020
gcaatttaaa tcatttcttt taaagcaaaa gcaattttct gaaaattttc accatttacg     1080
aacgatagag atctcgagct caagcttcga attctgcagt cgacggtacc atgttcttcc     1140
cctcctgagg ggaagaatta cgtcctgtag aaacccaac ccgtgaaatc aaaaaactcg     1200
acggcctgtg ggcattcagt ctggatcgcg aaaactgtgg aattgatcag cgttggtggg     1260
aaagcgcgtt acaagaaagc cgggcaattg ctgtgccagg cagttttaac gatcagttcg     1320
ccgatgcaga tattcgtaat tatgcgggca acgtctggta tcagcgcgaa gtctttatac     1380
cgaaaggttg gcaggccag cgtatcgtgc tgcgtttcga tgcggtcact cattacggca     1440
aagtgtgggt caataatcag gaagtgatgg agcatcaggg cggctatacg ccatttgaag     1500
ccgatgtcac gccgtatgtt attgccggga aaagtgtacg tatcaccgtt tgtgtgaaca     1560
acgaactgaa ctggcagact atcccgccgg gaatggtgat taccgacgaa aacggcaaga     1620
aaaagcagtc ttacttccat gatttcttta actatgccgg aatccatcgc agcgtaatgc     1680
tctacaccac gccgaacacc tgggtggacg atatcaccgt ggtgacgcat gtcgcgcaag     1740
actgtaacca cgcgtctgtt gactggcagg tggtggccaa tggtgatgtc agcgttgaac     1800
tgcgtgatgc ggatcaacag gtggttgcaa ctggacaagg cactagcggg actttgcaag     1860
tggtgaatcc gcacctctgg caaccgggtg aaggttatct ctatgaactg tgcgtcacag     1920
ccaaaagcca gacagagtgt gatatctacc cgcttcgcgt cggcatccgg tcagtggcag     1980
tgaagggcca acagttcctg attaaccaca accgttcta ctttactggc tttggtcgtc     2040
atgaagatgc ggacttacgt ggcaaaggat tcgataacgt gctgatggtg cacgaccacg     2100
cattaatgga ctggattggg gccaactcct accgtacctc gcattaccct tacgctgaag     2160
agatgctcga ctgggcagat gaacatggca tcgtggtgat tgatgaaact gctgctgtcg     2220
gctttaacct ctctttaggc attggtttcg aagcgggcaa caagccgaaa gaactgtaca     2280
gcgaagaggc agtcaacggg gaaactcagc aagcgcactt acaggcgatt aaagagctga     2340
tagcgcgtga caaaaaccac ccaagcgtgg tgatgtggag tattgccaac gaaccggata     2400
cccgtccgca agtgcacggg aatatttcgc cactggcgga agcaacgcgt aaactcgacc     2460
cgacgcgtcc gatcacctgc gtcaatgtaa tgttctgcga cgctcacacc gataccatca     2520
gcgatctctt tgatgtgctg tgcctgaacc gttattacgg atggtatgtc caaagcggcg     2580
```

```
atttggaaac ggcagagaag gtactggaaa aagaacttct ggcctggcag agaaactgc   2640
atcagccgat tatcatcacc gaatacggcg tggatacgtt agccgggctg cactcaatgt   2700
acaccgacat gtggagtgaa gagtatcagt gtgcatggct ggatatgtat caccgcgtct   2760
ttgatcgcgt cagcgccgtc gtcggtgaac aggtatggaa tttcgccgat tttgcgacct   2820
cgcaaggcat attgcgcgtt ggcggtaaca agaaagggat cttcactcgc gaccgcaaac   2880
cgaagtcggc ggcttttctg ctgcaaaaac gctggactgg catgaacttc ggtgaaaaac   2940
cgcagcaggg aggcaaacaa tgaggatcca cctgatctag agtccgcaaa aatcaccagt   3000
ctctctctac aaatctatct ctctctattt ttctccagaa taatgtgtga gtagttccca   3060
gataagggaa ttagggttct tatagggttt cgctcatgtg ttgagcatat aagaaaccct   3120
tagtatgtat ttgtatttgt aaaatacttc tatcaataaa atttctaatt cctaaaacca   3180
aaatccagtg acgcggccgc acccataata cccataatag ctgtttgcca tcgctacctt   3240
aggaccgtta tagttaatta ccctgttatc cctattaatt aagagctcgc taccttaaga   3300
gaggatatcg gcgcgccacc gggctgaaag cgacgttgga tgttaacatc tacaaattgc   3360
cttttcttat cgaccatgta cgtaagcgct tacgtttttg gtggacccct gaggaaactg   3420
gtagctgttg tgggcctgtg gtctcaagat ggatcattaa tttccacctt cacctacgat   3480
gggggcatc gcaccggtga gtaatattgt acggctaaga gcgaatttgg cctgtaagat   3540
ccttttacc gacaactcat ccacattgat ggtaggcaga aagttaaagg attatcgcaa   3600
gtcaatactt gcccattcat tgatctattt aaaggtgtgg cctcaaggat aatcgccaaa   3660
ccattatatt tgcaatctac caatccggac tcagatctcg agctcaagct tcgaattctg   3720
cagtcgacat gattgaacaa gatggattgc acgcaggttc tccggccgct tgggtggaga   3780
ggctattcgg ctatgactgg gcacaacaga caatcggctg ctctgatgcc gccgtgttcc   3840
ggctgtcagc gcaggggcgc ccggttcttt ttgtcaagac cgacctgtcc ggtgccctga   3900
atgaactgca ggacgaggca gcgcggctat cgtggctggc cacgacgggc gttccttgcg   3960
cagctgtgct cgacgttgtc actgaagcgg gaagggactg gctgctattg ggcgaagtgc   4020
cggggcagga tctcctgtca tctcaccttg ctcctgccga aaagtatcc atcatggctg   4080
atgcaatgcg gcggctgcat acgcttgatc cggctacctg cccattcgac caccaagcga   4140
aacatcgcat cgagcgagca cgtactcgga tggaagccgg tcttgtcgat caggatgatc   4200
tggacgaaga gcatcagggg ctcgcgccag ccgaactgtt cgccaggctc aaggcgcgca   4260
tgcccgacgg cgatgatctc gtcgtgaccc atggcgatgc ctgcttgccg aatatcatgg   4320
tggaaaatgg ccgcttttct ggattcatcg actgtggccg gctgggtgtg gcggaccgct   4380
atcaggacat agcgttggct acccgtgata ttgctgaaga gcttggcggc gaatgggctg   4440
accgcttcct cgtgctttac ggtatcgccg ctcccgattc gcagcgcatc gccttctatc   4500
gccttcttga cgagttcttc tgaggatcca cctagtctag aactagtccc tagagtcctg   4560
ctttaatgag atatgcgaga cgcctatgat cgcatgatat ttgctttcaa ttctgttgtg   4620
cacgttgtaa aaaacctgag catgtgtagc tcagatcctt accgccggtt tcggttcatt   4680
ctaatgaata tatcacccgt tactatcgta tttttatgaa taatattctc cgttcaattt   4740
actgattgta ccctactact tatatgtaca atattaaaat gaaaacaata tattgtgctg   4800
aataggttta tagcgacatc tatgatagag cgccacaata acaaacaatt gcgttttatt   4860
attacaaatc caatttttaaa aaagcggca gaaccggtca aacctaaaag actgattaca   4920
taaatcttat tcaaatttca aaagtgcccc aggggctagt atctacgaca caccgagcgg   4980
```

```
cgaactaata acgctcactg aagggaactc cggttccccg ccggcgcgca tgggtgagat    5040
tccttgaagt tgagtattgg ccgtccgctc taccgaaagt tacgggcacc attcaacccg    5100
gtccagcacg gcggccgggt aaccgacttg ctgccccgag aattatgcag catttttttg    5160
gtgtatgtgg gccccaaatg aagtgcaggt caaaccttga cagtgacgac aaatcgttgg    5220
gcgggtccag ggcgaatttt gcgacaacat gtcgaggctc agcaggagcg gccgcggcgc    5280
gcctctagaa tttaaatgga tcctacgtac tcgaggaatt caattcggcg ttaattcagt    5340
acattaaaaa cgtccgcaat gtgttattaa gttgtctaag cgtcaatttg tttacaccac    5400
aatatatcct gcca                                                      5414

<210> SEQ ID NO 55
<211> LENGTH: 525
<212> TYPE: DNA
<213> ORGANISM: Artificial sequence
<220> FEATURE:
<223> OTHER INFORMATION: Partial nucleotide sequence of nptII gene

<400> SEQUENCE: 55
agacaatcgg ctgctctgat gccgccgtgt tccggctgtc agcgcagggg cgcccggttc      60
tttttgtcaa gaccgacctg tccggtgccc tgaatgaact gcaggacgag gcagcgcggc     120
tatcgtggct ggccacgacg ggcgttcctt gcgcagctgt gctcgacgtt gtcactgaag     180
cgggaaggga ctggctgcta ttgggcgaag tgccggggca ggatctcctg tcatctcacc     240
ttgctcctgc cgagaaagta tccatcatgg ctgatgcaat gcggcggctg catacgcttg     300
atccggctac ctgcccattc gaccaccaag cgaaacatcg catcgagcga gcacgtactc     360
ggatggaagc cggtcttgtc gatcaggatg atctggacga agagcatcag ggctcgcgc      420 cagccgaact gttcgccagg ctcaaggcgc gcatgcccga cggcgaggat ctcgtcgtga     480
cccatggcga tgcctgcttg ccgaatatca tggtggaaaa tggcc                     525

<210> SEQ ID NO 56
<211> LENGTH: 20
<212> TYPE: DNA
<213> ORGANISM: Artificial sequence
<220> FEATURE:
<223> OTHER INFORMATION: nptII 80F primer

<400> SEQUENCE: 56
agacaatcgg ctgctctgat                                                  20

<210> SEQ ID NO 57
<211> LENGTH: 20
<212> TYPE: DNA
<213> ORGANISM: Artificial sequence
<220> FEATURE:
<223> OTHER INFORMATION: nptII 604R primer

<400> SEQUENCE: 57
ggccattttc caccatgata                                                  20

<210> SEQ ID NO 58
<211> LENGTH: 390
<212> TYPE: DNA
<213> ORGANISM: Artificial sequence
<220> FEATURE:
<223> OTHER INFORMATION: Partial nucleotide sequence of nptII gene

<400> SEQUENCE: 58
```

```
agacaatcgg ctgctctgat gccgccgtgt tccggctgtc agcgcagggg cgcccggttc    60
tttttgtcaa gaccgacctg tccggtgccc tgaatgaact gcaggacgag gcagcgcggc   120
tatcgtggct ggccacgacg ggcgttcctt gcgcagctgt gctcgacgtt gtcactgaag   180
cgggaaggga ctggctgcta ttgggcgaag tgcgggggca ggatctcctg tcatctcacc   240
ttgctcctgc cgagaaagta tccatcatgg ctgatgcaat gcggcggctg catacgcttg   300
atccggctac ctgcccattc gaccaccaag cgaaacatcg catcgagcga gcacgtactc   360
ggatggaagc cggtcttgtc gatcaggatg                                    390
```

<210> SEQ ID NO 59
<211> LENGTH: 20
<212> TYPE: DNA
<213> ORGANISM: Artificial sequence
<220> FEATURE:
<223> OTHER INFORMATION: nptII 470R primer

<400> SEQUENCE: 59

```
tcatcctgat cgacaagacc                                                20
```

<210> SEQ ID NO 60
<211> LENGTH: 264
<212> TYPE: DNA
<213> ORGANISM: Artificial sequence
<220> FEATURE:
<223> OTHER INFORMATION: Partial nucleotide sequence of nptII gene with
      126bp deletion

<400> SEQUENCE: 60

```
agacaatcgg ctgctctgat gccgccgtgt tccggctgtc agcgcagggg caagcgggaa    60
gggactggct gctattgggc gaagtgccgg ggcaggatct cctgtcatct caccttgctc   120
ctgccgagaa agtatccatc atggctgatg caatgcggcg gctgcatacg cttgatccgg   180
ctacctgccc attcgaccac caagcgaaac atcgcatcga gcgagcacgt actcggatgg   240
aagccggtct tgtcgatcag gatg                                          264
```

<210> SEQ ID NO 61
<211> LENGTH: 252
<212> TYPE: DNA
<213> ORGANISM: Artificial sequence
<220> FEATURE:
<223> OTHER INFORMATION: Partial nucleotide sequence of nptII gene with
      138bp deletion

<400> SEQUENCE: 61

```
agacaatcgg ctgctctgat gccgccgtgt tccggctgta agcgggaagg gactggctgc    60
tattgggcga agtgccgggg caggatctcc tgtcatctca ccttgctcct gccgagaaag   120
tatccatcat ggctgatgca atgcggcggc tgcatacgct tgatccggct acctgcccat   180
tcgaccacca agcgaaacat cgcatcgagc gagcacgtac tcggatggaa gccggtcttg   240
tcgatcagga tg                                                       252
```

<210> SEQ ID NO 62
<211> LENGTH: 251
<212> TYPE: DNA
<213> ORGANISM: Artificial sequence
<220> FEATURE:
<223> OTHER INFORMATION: Partial nucleotide sequence of nptII gene with
      139bp deletion

<400> SEQUENCE: 62

```
gacaatcggc tgctctgatg ccgccgtgtt ccggctgtaa gcgggaaggg actggctgct      60
attgggcgaa gtgccggggc aggatctcct gtcatctcac cttgctcctg ccagaaaagt     120
atccatcatg gctgatgcaa tgcggcggct gcatacgctt gatccggcta cctgcccatt     180
cgaccaccaa gcgaaacatc gcatcgagcg agcacgtact cggatggaag ccggtcttgt     240
cgatcaggat g                                                          251

<210> SEQ ID NO 63
<211> LENGTH: 245
<212> TYPE: DNA
<213> ORGANISM: Artificial sequence
<220> FEATURE:
<223> OTHER INFORMATION: Partial nucleotide sequence of nptII gene with
      145bp deletion

<400> SEQUENCE: 63
agacaatcgg ctgctctgat gccgccgtgt tcaagcggga agggactggc tgctattggg      60
cgaagtgccg gggcaggatc tcctgtcatc tcaccttgct cctgccgaga agtatccat     120 catggctgat gcaatgcggc ggctgcatac gcttgatccg gctacctgcc cattcgacca    180
ccaagcgaaa catcgcatcg agcgagcacg tactcggatg gaagccggtc ttgtcgatca    240
ggatg                                                                 245

<210> SEQ ID NO 64
<211> LENGTH: 240
<212> TYPE: DNA
<213> ORGANISM: Artificial sequence
<220> FEATURE:
<223> OTHER INFORMATION: Partial nucleotide sequence of nptII gene with
      150bp deletion

<400> SEQUENCE: 64
agacaatcgg ctgctctgat gccgccgaag cgggaaggga ctggctgcta ttgggcgaag      60
tgccggggca ggatctcctg tcatctcacc ttgctcctgc cgagaaagta tccatcatgg    120
ctgatgcaat gcggcggctg catacgcttg atccggctac ctgcccattc gaccaccaag    180
cgaaacatcg catcgagcga gcacgtactc ggatggaagc cggtcttgtc gatcaggatg    240

<210> SEQ ID NO 65
<211> LENGTH: 116
<212> TYPE: DNA
<213> ORGANISM: Artificial sequence
<220> FEATURE:
<223> OTHER INFORMATION: Partial nucleotide sequence of mGUS gene with
      4bp deletion

<400> SEQUENCE: 65
accatttacg aacgatagag atctcgagct caagcttcga attctgcagt cgacggtacc      60
atgttcttcc cctcggggaa gaattacgtc ctgtagaaac cccaacccgt gaaatc        116

<210> SEQ ID NO 66
<211> LENGTH: 109
<212> TYPE: DNA
<213> ORGANISM: Artificial sequence
<220> FEATURE:
<223> OTHER INFORMATION: Partial nucleotide sequence of mGUS gene with
      11bp deletion

<400> SEQUENCE: 66
accatttacg aacgatagag atctcgagct caagcttcga attctgcagt cgacggtacc      60
atgttcttcc cctcctttac gtcctgtaga aaccccaacc cgtgaaatc                109
```

<210> SEQ ID NO 67
<211> LENGTH: 2147
<212> TYPE: DNA
<213> ORGANISM: Artificial sequence
<220> FEATURE:
<223> OTHER INFORMATION: nucleotide sequence of TRV
      RNA2-CP-sgNptII-k2sgP-DsRed2

<400> SEQUENCE: 67

| | | | | | |
|---|---|---|---|---|---|
| cattgcacct | atggtgttgc | cctggctggg | gtatgtcagt | gatcgcagta | gaatgtacta | 60 |
| attgacaagt | tggagaatac | ggtagaacgt | ccttatccaa | cacagccttt | atccctctcc | 120 |
| ctgacgaggt | ttttgtcagt | gtaatatttc | tttttgaact | atccagctta | gtaccgtacg | 180 |
| ggaaagtgac | tggtgtgctt | atctttgaaa | tgttactttg | ggtttcggtt | ctttaggtta | 240 |
| gtaagaaagc | acttgtcttc | tcatacaaag | gaaaacctga | gacgtatcgc | ttacgaaagt | 300 |
| agcaatgaaa | gaaaggtggt | ggttttaatc | gctaccgcaa | aaacgatggg | gtcgttttaa | 360 |
| ttaacttctc | ctacgcaagc | gtctaaacgg | acgttggggt | tttgctagtt | tctttagaga | 420 |
| aaactagcta | agtctttaat | gttatcatta | gagatggcat | aaatataata | cttgtgtctg | 480 |
| ctgataagat | cattttaatt | tggacgatta | gacttgttga | actacaggtt | actgaatcac | 540 |
| ttgcgctaat | caacaagctt | aaaagcttgt | taacgaggct | gtcagcgcag | gggcgccgtt | 600 |
| ttagagctag | aaatagcaag | ttaaataag | gctagtccgt | tatcaacttg | aaaaagtggc | 660 |
| accgagtcgg | tgcttttttt | ctcgagggat | ttaaggacgt | gaactctgtt | gagatctctg | 720 |
| tgaaattcag | agggtgggtg | ataccatatt | cactgatgcc | attagcgaca | tctaaatagg | 780 |
| gctaattgtg | actaatttga | gggaatttcc | tttaccattg | acgtcagtgt | cgttggtagc | 840 |
| atttgagttt | cgtaactata | acggtcctaa | ggtagcgaac | atcttgttct | ggggtttcac | 900 |
| actatctttta | gagaaagtgt | taagttaatt | aagttatctt | aattaagagc | ataattatac | 960 |
| tgatttgtct | ctcgttgata | gagtctatca | ttctgttact | aaaaatttga | caactcggtt | 1020 |
| tgctgaccta | ctggttactg | tatcacttac | ccgagttaac | gagatggcct | cctccgagaa | 1080 |
| cgtcatcacc | gagttcatgc | gcttcaaggt | gcgcatggag | ggcaccgtga | acggccacga | 1140 |
| gttcgagatc | gagggcgagg | gcgagggccg | cccctacgag | ggccacaaca | ccgtgaagct | 1200 |
| gaaggtgacc | aagggcggcc | ccctgccctt | cgcctgggac | atcctgtccc | cccagttcca | 1260 |
| gtacggctcc | aaggtgtacg | tgaagcaccc | cgccgacatc | cccgactaca | agaagctgtc | 1320 |
| cttccccgag | ggcttcaagt | gggagcgcgt | gatgaacttc | gaggacggcg | gcgtggcgac | 1380 |
| cgtgacccag | gactcctccc | tgcaggacgg | ctgcttcatc | tacaaggtga | agttcatcgg | 1440 |
| cgtgaacttc | ccctccgacg | gccccgtgat | gcagaagaag | accatgggct | gggaggcctc | 1500 |
| caccgagcgc | ctgtaccccc | gcgacggcgt | gctgaagggc | gagacccaca | aggccctgaa | 1560 |
| gctgaaggac | ggcggccact | acctggtgga | gttcaagtcc | atctacatgg | ccaagaagcc | 1620 |
| cgtgcagctg | cccggctact | actacgtgga | cgccaagctg | gacatcacct | cccacaacga | 1680 |
| ggactacacc | atcgtggagc | agtacgagcg | caccgagggc | cgccaccacc | tgttcctgtg | 1740 |
| agtcgaccgg | gcatgtcccg | aagacattaa | actacggttc | tttaagtaga | tccgtgtctg | 1800 |
| aagttttagg | ttcaatttaa | acctacgaga | ttgacattct | cgactgatct | tgattgatcg | 1860 |
| gtaagtcttt | tgtaatttaa | ttttcttttt | gattttattt | taaattgtta | tctgtttctg | 1920 |
| tgtatagact | gtttgagatc | ggcgtttggc | cgactcattg | tcttaccata | ggggaacgga | 1980 |
| ctttgtttgt | gttgttattt | tatttgtatt | ttattaaaat | tctcaacgat | ctgaaaaagc | 2040 |

-continued ctcgcggcta agagattgtt gggggggtgag taagtacttt taaagtgatg atggttacaa    2100
aggcaaaagg ggtaaaaccc ctcgcctacg taagcgttat tacgccc    2147

<210> SEQ ID NO 68
<211> LENGTH: 21
<212> TYPE: DNA
<213> ORGANISM: Artificial sequence
<220> FEATURE:
<223> OTHER INFORMATION: mutated QQR target sequence in Tobacco lines 3E,3F,3G

<400> SEQUENCE: 68
ttcttcccct cagggaaga a    21

<210> SEQ ID NO 69
<211> LENGTH: 23
<212> TYPE: DNA
<213> ORGANISM: Artificial sequence
<220> FEATURE:
<223> OTHER INFORMATION: mutated QQR target sequence in Tobacco lines 5C

<400> SEQUENCE: 69
ttcttcccct ctgaggggaa gaa    23

<210> SEQ ID NO 70
<211> LENGTH: 23
<212> TYPE: DNA
<213> ORGANISM: Artificial sequence
<220> FEATURE:
<223> OTHER INFORMATION: mutated QQR target sequence in Tobacco lines 5F

<400> SEQUENCE: 70
ttcttcccct ctgaggggaa gaa    23

<210> SEQ ID NO 71
<211> LENGTH: 23
<212> TYPE: DNA
<213> ORGANISM: Artificial sequence
<220> FEATURE:
<223> OTHER INFORMATION: mutated QQR target sequence in Tobacco lines 5H

<400> SEQUENCE: 71
ttcttcccct ctgaggggaa gaa    23

<210> SEQ ID NO 72
<211> LENGTH: 20
<212> TYPE: DNA
<213> ORGANISM: Artificial sequence
<220> FEATURE:
<223> OTHER INFORMATION: mutated QQR target sequence in Tobacco lines 6A

<400> SEQUENCE: 72
ttcttcccct cggggaagaa    20

<210> SEQ ID NO 73
<211> LENGTH: 25
<212> TYPE: DNA
<213> ORGANISM: Artificial sequence
<220> FEATURE:
<223> OTHER INFORMATION: mutated QQR target sequence in Tobacco lines 7B

<400> SEQUENCE: 73
ttcttcccct ctctgagggg aagaa    25

<210> SEQ ID NO 74
<211> LENGTH: 14
<212> TYPE: DNA
<213> ORGANISM: Artificial sequence
<220> FEATURE:
<223> OTHER INFORMATION: mutated QQR target sequence in Tobacco lines 8A

<400> SEQUENCE: 74
ttcttcccct ccgt                                                         14

<210> SEQ ID NO 75
<211> LENGTH: 2314
<212> TYPE: DNA
<213> ORGANISM: Artificial sequence
<220> FEATURE:
<223> OTHER INFORMATION: nucleotide sequence of TRV with two guide RNA
      for the endogenic TOM3 and TOM1 (Capital letters) petunia genes

<400> SEQUENCE: 75
ataaaacatt gcacctatgg tgttgccctg gctggggtat gtcagtgatc gcagtagaat        60
gtactaattg caagttgga gaatacggta gaacgtcctt atccaacaca gcctttatcc       120
ctctccctga cgaggttttt gtcagtgtaa tatttctttt tgaactatcc agcttagtac      180
cgtacgggaa agtgactggt gtgcttatct ttgaaatgtt actttgggtt tcggttcttt      240
aggttagtaa gaaagcactt gtcttctcat acaaaggaaa acctgagacg tatcgcttac      300
gaaagtagca atgaaagaaa ggtggtggtt ttaatcgcta ccgcaaaaac gatgggtcg       360 ttttaattaa cttctcctac gcaagcgtct aaacggacgt tggggttttg ctagtttctt      420
tagagaaaac tagctaagtc tttaatgtta tcattagaga tggcataaat ataatacttg      480
tgtctgctga taagatcatt ttaatttgga cgattagact tgttgaacta caggttactg      540
aatcacttgc gctaatcaac aagcttgtta acgagtagtt gtgatgccta acctcgtttt      600
agagctagaa atagcaagtt aaaataaggc tagtccgtta tcaacttgaa aaagtggcac      660
cgagtcggtg ctttttttct cgagggattt aaggacgtga actctgttga gatcttctag      720
aaagattaaa agcttgttaa cgagagtgtt tatcttccat cctagtttta gagctagaaa      780
tagcaagtta aaataaggct agtccgttat caacttgaaa aagtggcacc gagtcggtgc      840
tttttttctc gagggattta aggacgtgaa ctctgttgag atctctgtga aattcagagg      900
gtgggtgata ccatattcac tgatgccatt agcgacatct aaatagggct aattgtgact      960
aatttgaggg aatttccttt accattgacg tcagtgtcgt tggtagcatt tgagtttcgt     1020
aactataacg gtcctaaggt agcgaacatc ttgttctggg gtttcacact atctttagag     1080
aaagtgttaa gttaattaag ttatcttaat taagagcata attatactga tttgtctctc     1140
gttgatagag tctatcattc tgttactaaa aatttgacaa ctcggtttgc tgacctactg     1200
gttactgtat cacttacccg agttaacgag atggcctcct ccgagaacgt catcaccgag     1260
ttcatgcgct tcaaggtgcg catggagggc accgtgaacg gccacgagtt cgagatcgag     1320
ggcgagggcg agggccgccc ctacgagggc cacaacaccg tgaagctgaa ggtgaccaag     1380
ggcggccccc tgcccttcgc ctgggacatc ctgtcccccc agttccagta cggctccaag     1440
gtgtacgtga agcaccccgc cgacatcccc gactacaaga gctgtccttt ccccgagggc     1500
ttcaagtggg agcgcgtgat gaacttcgag gacggcggcg tggcgaccgt gacccaggac     1560
tcctccctgc aggacggctg cttcatctac aaggtgaagt tcatcggcgt gaacttcccc     1620
tccgacggcc ccgtgatgca gaagaagacc atgggctggg aggcctccac cgagcgcctg     1680 taccccgcg acggcgtgct gaagggcgag acccacaagg ccctgaagct gaaggacggc     1740

```
ggccactacc tggtggagtt caagtccatc tacatggcca agaagcccgt gcagctgccc    1800
ggctactact acgtggacgc caagctggac atcacctccc acaacgagga ctacaccatc    1860
gtggagcagt acgagcgcac cgagggccgc caccacctgt tcctgtgagt cgaccgggca    1920
tgtcccgaag acattaaact acggttcttt aagtagatcc gtgtctgaag ttttaggttc    1980
aatttaaacc tacgagattg acattctcga ctgatcttga ttgatcggta agtcttttgt    2040
aatttaattt tcttttgat tttatttaa attgttatct gtttctgtgt atagactgtt      2100
tgagatcggc gtttggccga ctcattgtct taccataggg aacggactt tgtttgtgtt     2160 gttatttat ttgtatttta ttaaaattct caacgatctg aaaaagcctc gcggctaaga     2220
gattgttggg gggtgagtaa gtacttttaa agtgatgatg gttacaaagg caaaaggggt    2280 aaaaccctc gcctacgtaa gcgttattac gccc                                 2314
```

```
<210> SEQ ID NO 76
<211> LENGTH: 25
<212> TYPE: DNA
<213> ORGANISM: Artificial sequence
<220> FEATURE:
<223> OTHER INFORMATION: TOM1 Forward 110F primer

<400> SEQUENCE: 76
tcaactaata aggatcgagt tgagg                                          25

<210> SEQ ID NO 77
<211> LENGTH: 21
<212> TYPE: DNA
<213> ORGANISM: Artificial sequence
<220> FEATURE:
<223> OTHER INFORMATION: TOM1 Reverse 783R primer

<400> SEQUENCE: 77
aacatggcca gacattattg c                                              21

<210> SEQ ID NO 78
<211> LENGTH: 20
<212> TYPE: DNA
<213> ORGANISM: Artificial sequence
<220> FEATURE:
<223> OTHER INFORMATION: TOM3 Forward 623F primer

<400> SEQUENCE: 78
tatttgccca cccacttgtt                                                20

<210> SEQ ID NO 79
<211> LENGTH: 23
<212> TYPE: DNA
<213> ORGANISM: Artificial sequence
<220> FEATURE:
<223> OTHER INFORMATION: TOM3 Reverse 411R primer

<400> SEQUENCE: 79
cgtgcctggt agtatatctc agc                                            23

<210> SEQ ID NO 80
<211> LENGTH: 20
<212> TYPE: DNA
<213> ORGANISM: Artificial sequence
<220> FEATURE:
<223> OTHER INFORMATION: nucleotide sequence of TOM1 target site

<400> SEQUENCE: 80
```
agtgtttatc ttccatccta                                              20

<210> SEQ ID NO 81
<211> LENGTH: 20
<212> TYPE: DNA
<213> ORGANISM: Artificial sequence
<220> FEATURE:
<223> OTHER INFORMATION: nucleotide sequence of TOM3 target site

<400> SEQUENCE: 81
tagttgtgat gcctaacctc                                              20

<210> SEQ ID NO 82
<211> LENGTH: 55
<212> TYPE: DNA
<213> ORGANISM: Artificial sequence
<220> FEATURE:
<223> OTHER INFORMATION: mutate TOM1 target site - 1base deletion in
      plant 3769-4

<400> SEQUENCE: 82
aattgtcttt ggatttcaca aacaagtgtt tatcttccat ctaaggtatg ttctt        55

<210> SEQ ID NO 83
<211> LENGTH: 57
<212> TYPE: DNA
<213> ORGANISM: Artificial sequence
<220> FEATURE:
<223> OTHER INFORMATION: mutate TOM1 target site - 1base insertion found
      in plant 3769-27

<400> SEQUENCE: 83
aattgtcttt ggatttcaca aacaagtgtt tatcttccat cactaaggta tgttctt     57

<210> SEQ ID NO 84
<211> LENGTH: 46
<212> TYPE: DNA
<213> ORGANISM: Artificial sequence
<220> FEATURE:
<223> OTHER INFORMATION: mutate TOM1 target site  10 base deletion found
      in plant 3769-41

<400> SEQUENCE: 84
aattgtcttt ggatttcaca aacaagtgtt tataaggtat gttctt                 46

<210> SEQ ID NO 85
<211> LENGTH: 45
<212> TYPE: DNA
<213> ORGANISM: Artificial sequence
<220> FEATURE:
<223> OTHER INFORMATION: mutate TOM1 target site  11 base deletion found
      in plant 3769-43

<400> SEQUENCE: 85
aattgtcttt ggatttcaca aacaagtgtt tataggtatg ttctt                  45

<210> SEQ ID NO 86
<211> LENGTH: 59
<212> TYPE: DNA
<213> ORGANISM: Artificial sequence
<220> FEATURE:
<223> OTHER INFORMATION: mutate TOM3 target site  7 base deletion found
      in plant 3742-66

<400> SEQUENCE: 86
cgtcgggatg ttcagaagtt gcatcctgac atcacaacta tcttgatgtc cggttgtca   59

<210> SEQ ID NO 87
<211> LENGTH: 65
<212> TYPE: DNA
<213> ORGANISM: Artificial sequence
<220> FEATURE:
<223> OTHER INFORMATION: mutate TOM3 target site  1 base deletion found
      in plant 3769-4

<400> SEQUENCE: 87
cgtcgggatg ttcagaagtt gcatcctgag ttaggcatca caactatctt gatgtccggt    60
tgtca                                                                65

<210> SEQ ID NO 88
<211> LENGTH: 67
<212> TYPE: DNA
<213> ORGANISM: Artificial sequence
<220> FEATURE:
<223> OTHER INFORMATION: mutate TOM3 target site  1 base insertion found
      in plant 3769-9

<400> SEQUENCE: 88
cgtcgggatg ttcagaagtt gcatcctgag agttaggcat cacaactatc ttgatgtccg    60
gttgtca                                                              67

<210> SEQ ID NO 89
<211> LENGTH: 63
<212> TYPE: DNA
<213> ORGANISM: Artificial sequence
<220> FEATURE:
<223> OTHER INFORMATION: mutate TOM3 target site  3 base deletion found
      in plant 3769-1

<400> SEQUENCE: 89
cgtcgggatg ttcagaagtt gcatcctgag aggcatcaca actatcttga tgtccggttg    60
tca                                                                  63

<210> SEQ ID NO 90
<211> LENGTH: 60
<212> TYPE: DNA
<213> ORGANISM: Artificial sequence
<220> FEATURE:
<223> OTHER INFORMATION: mutate TOM3 target site  6 base deletion found
      in plant 3769-3

<400> SEQUENCE: 90
cgtcgggatg ttcagaagtt gcatcctgag catcacaact atcttgatgt ccggttgtca    60

<210> SEQ ID NO 91
<211> LENGTH: 60
<212> TYPE: DNA
<213> ORGANISM: Artificial sequence
<220> FEATURE:
<223> OTHER INFORMATION: mutate TOM3 target site  8 base deletion and 2
      base insertion found in plant 3769-6

<400> SEQUENCE: 91
cgtcgggatg ttcagaagtt gcatcctgag cgtcacgact atcttgatgt ccggttgtca    60

<210> SEQ ID NO 92
<211> LENGTH: 67
<212> TYPE: DNA
<213> ORGANISM: Artificial sequence
<220> FEATURE:
<223> OTHER INFORMATION: mutate TOM3 target site  1 base deletion found
      in plant 3769-9

<400> SEQUENCE: 92

```
cgtcgggatg ttcagaagtt gcatcctgag agttaggcat cacaactatc ttgatgtccg    60
gttgtca                                                              67
```

<210> SEQ ID NO 93
<211> LENGTH: 57
<212> TYPE: DNA
<213> ORGANISM: Artificial sequence
<220> FEATURE:
<223> OTHER INFORMATION: mutate TOM1 target site - 1base insertion found
      in plant 3769-27

<400> SEQUENCE: 93

```
aattgtcttt ggatttcaca aacaagtgtt tatcttccat ctctaaggta tgttctt       57
```

<210> SEQ ID NO 94
<211> LENGTH: 825
<212> TYPE: DNA
<213> ORGANISM: Artificial sequence
<220> FEATURE:
<223> OTHER INFORMATION: TOM1 Petunia hybrida Coding sequence (taken
      from literature).

<400> SEQUENCE: 94

```
atgagtatga ccaactggtg ggatgagatc gatgaatcag ttgattggca agatgggatt    60
ttctactctc tttgtgcttc ttatgctctt gtctcagctg ttgcccttat tcaactaata   120
aggatcgagt tgagggtacc cgagtatggt tggacaacac aaaaggtttt ccatctgatg   180
aactttattg taaatggagt tcgtgcaatt gtctttggat ttcacaaaca agtgtttatc   240
ttccatccta aggttcttac tctgacaata ttggacctac cagggctcct tttcttctca   300
acatttacac tccttgttct attctgggct gaaatatatc accaggctag gagtttacca   360
acagataagc tcagaatttc ctatatttcg ataaatgctg caatgtactt cattcaggcc   420
tgtatctggg tttacatctg gctcaacgac aatagcactg tggaattcat gggaagata   480 tttatagcag ttgtatcctt tattgcagcg ttgggctttc tgctctatgg cggaaggtta   540
tttctcatgc tgcggcgctt tcctattgag tctaaaggga ggagaaagaa gcttcatgag   600
gttggatctg tgactgccat atgtttcacc tgtttcctca ttagatgctt tgtggttgtt   660
ttatccgctt ttgattcaga cgcatctctt gatgtcttgg atcatcccct tctgaatctg   720
atatactacc tgctggtaga aatacttcct tcagcccttg tactgtacat cttacgaaag   780
ttgcctccaa aaagagtatc tgcacaatac cacccaatca gttaa                   825
```

<210> SEQ ID NO 95
<211> LENGTH: 871
<212> TYPE: DNA
<213> ORGANISM: Artificial sequence
<220> FEATURE:
<223> OTHER INFORMATION: TOM3 Petunia hybrida Coding sequence (taken
      from literature).

<400> SEQUENCE: 95

```
atggggcggg cagagatggt ggtaggcccg tcgtccacgg cggtgacgta tcagctgata    60
agttggtggg aagaggtgaa cagatcacgc gcttggcaag accgtatatt ccacgtcctt   120
gctatccttt acggcattgt cgccgccgtt gtctcttgttc aattaatacg cattcaaatg   180
agagttcctg aatatggttg gaccactcaa aaagtcttcc acttcctcaa tttcttggtg   240
aatggggttc gctcgctagt gtttgtattt cgtcgggatg ttcagaagtt gcatcctgag   300
```

```
attgtccagc atatcttgct tgatatgcca agtcttgcat tcttcacaac ttatgctctg    360
ctagtattat tctgggctga gatatactac caggcacgcg ctgtatccac ggatgggctt    420
agacccagtt tcttcacaat caatggagtg gtttatgcta ttcagattat attatggctg    480
ataatatggt ggaaacctat tcgagtactc gtcattttat ctaagatgtt ctttgcaggt    540
gtatctctat ttgctgcgtt ggggtttctc ctctatggtg gaaggctttt tcttatgtta    600
caacggtttc ctgtggaatc aaaagggaga cgtaagaagc tacaggaggt tggctatgtc    660
acaacaatat gttttcatg cttcctcatt agatgcgtta tgatgtgctt caatgcattt    720
gataaagctg cagatcttga tgttttggat catccaattt tgaatttgat atattacctg    780
ttagtggaga tactaccttc ttcacttgtc cttttattt tgaggaagtt acctccaaag    840
cgagggatca cacagtacca ccctattcgc t                                   871
```

<210> SEQ ID NO 96
<211> LENGTH: 713
<212> TYPE: DNA
<213> ORGANISM: Artificial sequence
<220> FEATURE:
<223> OTHER INFORMATION: Synthetic sequence

<400> SEQUENCE: 96

```
ctcgaggacg tcagtgtcgt tggtagcatt tgagtttcgg ctgtcagcgc aggggcgccg     60
ttttagagct agaaatagca agttaaaata aggctagtcc gttatcaact tgaaaaagtg    120
gcaccgagtc ggtgcttttt ttcctaagga tttaaggacg tgaactctgt tgagatctac    180
atcttgttct ggggtttcac actatcttta gagaaagtgt taagttaatt aagttatctt    240
aattaagagc ataattatac tgatttgtct ctcgttgata gagtctatca ttctgttact    300
aaaaatttga caactcggtt tgctgaccta ctggttactg tatcacttac ccgagttaac    360
gagcctaagg atggcctcct ccgagaacgt catcaccgag ttcatgcgct tcaaggtgcg    420
catggagggc accgtgaacg gccacgagtt cgagatcgag ggcgagggcg agggccgccc    480
ctacgagggc cacaacaccg tgaagctgaa ggtgaccaag gcggcccccc tgcccttcgc    540
ctgggacatc ctgtcccccc agttccagta cggctccaag gtgtacgtga agcacccccgc    600 cgacatcccc gactacaaga agctgtcctt ccccgagggc ttcaagtggg agcgcgtgat    660
gaacttcgag gacggcggcg tggcgaccgt gacccaggac tcctccctgc agg           713
```

<210> SEQ ID NO 97
<211> LENGTH: 54
<212> TYPE: DNA
<213> ORGANISM: Artificial sequence
<220> FEATURE:
<223> OTHER INFORMATION: nucleotide sequence of the target site detected
      in the N. benthamiana target gene NptII with -2bp indel.

<400> SEQUENCE: 97

```
tgctctgatg ccgccgtgtt ccggctgtca gcgcaggggc ccggttcttt ttgt            54
```

<210> SEQ ID NO 98
<211> LENGTH: 48
<212> TYPE: DNA
<213> ORGANISM: Artificial sequence
<220> FEATURE:
<223> OTHER INFORMATION: nucleotide sequence of the target site detected
      in the N. benthamiana target gene NptII with -8bp indel.

<400> SEQUENCE: 98
tgctctgatg ccgccgtgtt ccggctgtca gcgcccggtt cttttttgt         48

<210> SEQ ID NO 99
<211> LENGTH: 20
<212> TYPE: DNA
<213> ORGANISM: Artificial sequence
<220> FEATURE:
<223> OTHER INFORMATION: nucleotide sequence of the target site detected
      in the N. benthamiana target gene NptII with -36bp indel.

<400> SEQUENCE: 99
tgctctgatg ttctttttgt                                          20

<210> SEQ ID NO 100
<211> LENGTH: 49
<212> TYPE: DNA
<213> ORGANISM: Artificial sequence
<220> FEATURE:
<223> OTHER INFORMATION: nucleotide sequence of the target site detected
      in the N. benthamiana target gene NptII with -8bp+1bp indel.

<400> SEQUENCE: 100
tgctctgatg ccgccgtgtt ccggctgtca gcgcgccggt tcttttttgt         49

<210> SEQ ID NO 101
<211> LENGTH: 57
<212> TYPE: DNA
<213> ORGANISM: Artificial sequence
<220> FEATURE:
<223> OTHER INFORMATION: nucleotide sequence of the target site detected
      in the N. benthamiana target gene NptII with +1bp indel.

<400> SEQUENCE: 101
tgctctgatg ccgccgtgtt ccggctgtca gcgcaggggc cgcccggttc ttttttgt  57

<210> SEQ ID NO 102
<211> LENGTH: 57
<212> TYPE: DNA
<213> ORGANISM: Artificial sequence
<220> FEATURE:
<223> OTHER INFORMATION: nucleotide sequence of the target site detected
      in the N. benthamiana target gene NptII with +1bp indel.

<400> SEQUENCE: 102
tgctctgatg ccgccgtgtt ccggctgtca gcgcaggggc agcccggttc ttttttgt  57

<210> SEQ ID NO 103
<211> LENGTH: 53
<212> TYPE: DNA
<213> ORGANISM: Artificial sequence
<220> FEATURE:
<223> OTHER INFORMATION: nucleotide sequence of the target site detected
      in the N. benthamiana target gene NptII with -3bp indel.

<400> SEQUENCE: 103
tgctctgatg ccgccgtgtt ccggctgtca gcgcagggcc cggttctttt tgt       53

<210> SEQ ID NO 104
<211> LENGTH: 48
<212> TYPE: DNA
<213> ORGANISM: Artificial sequence
<220> FEATURE:
<223> OTHER INFORMATION: nucleotide sequence of the target site detected
      in the N. benthamiana target gene NptII with -8bp indel.

<400> SEQUENCE: 104
tgctctgatg ccgccgtgtt ccggctgtca gcgcagggtt cttttttgt            48

```
<210> SEQ ID NO 105
<211> LENGTH: 57
<212> TYPE: DNA
<213> ORGANISM: Artificial sequence
<220> FEATURE:
<223> OTHER INFORMATION: nucleotide sequence of the target site detected
      in the N. benthamiana target gene NptII with +1bp indel.

<400> SEQUENCE: 105
tgctctgatg ccgccgtgtt ccggctgtca gcgcaggggc tgcccggttc tttttgt        57

<210> SEQ ID NO 106
<211> LENGTH: 50
<212> TYPE: DNA
<213> ORGANISM: Artificial sequence
<220> FEATURE:
<223> OTHER INFORMATION: nucleotide sequence of the target site detected
      in the N. benthamiana target gene NptII with -6bp indel.

<400> SEQUENCE: 106
tgctctgatg ccgccgtgtt ccggctgtca gcgcgcccgg ttcttttgt                  50

<210> SEQ ID NO 107
<211> LENGTH: 48
<212> TYPE: DNA
<213> ORGANISM: Artificial sequence
<220> FEATURE:
<223> OTHER INFORMATION: nucleotide sequence of the target site detected
      in the N. benthamiana target gene NptII with -8bp indel.
<220> FEATURE:
<221> NAME/KEY: misc_feature
<222> LOCATION: (39)..(39)
<223> OTHER INFORMATION: n is a, c, g, or t

<400> SEQUENCE: 107
tgctctgatg ccgccgtgtt ccggctgtca gcgcagggnt cttttgt                    48

<210> SEQ ID NO 108
<211> LENGTH: 73
<212> TYPE: DNA
<213> ORGANISM: Artificial sequence
<220> FEATURE:
<223> OTHER INFORMATION: Complementary strand of nucleotide sequence of
      a fragment of the mgus gene, targeted by the pTRV2 QQR sgRNA

<400> SEQUENCE: 108
tcacgggttg gggtttctac aggacgtaat tcttcccctc aggaggggaa gaacatggta     60
ccgtcgactg cag                                                        73

<210> SEQ ID NO 109
<211> LENGTH: 52
<212> TYPE: DNA
<213> ORGANISM: Artificial sequence
<220> FEATURE:
<223> OTHER INFORMATION: Partial nucleotide sequence of nptII gene

<400> SEQUENCE: 109
ctgatgccgc cgtgttccgg ctgtcagcgc agggcgccc ggttctttttt gt             52

<210> SEQ ID NO 110
<211> LENGTH: 74
<212> TYPE: DNA
<213> ORGANISM: Artificial sequence
<220> FEATURE:
<223> OTHER INFORMATION: Partial nucleotide sequence of nptII gene
```

-continued

<400> SEQUENCE: 110
cagacaatcg gctgctctga tgccgccgtg ttccggctgt cagcgcaggg gcgcccggtt    60 cttttttgtca agac    74

<210> SEQ ID NO 111
<211> LENGTH: 74
<212> TYPE: DNA
<213> ORGANISM: Artificial sequence
<220> FEATURE:
<223> OTHER INFORMATION: Partial nucleotide sequence of nptII gene

<400> SEQUENCE: 111
gggcgttcct tgcgcagctg tgctcgacgt tgtcactgaa gcgggaaggg actggctgct    60
attgggcgaa gtgc    74

<210> SEQ ID NO 112
<211> LENGTH: 56
<212> TYPE: DNA
<213> ORGANISM: Artificial sequence
<220> FEATURE:
<223> OTHER INFORMATION: Partial TOM1 Petunia hybrida Coding sequence

<400> SEQUENCE: 112
aattgtcttt ggatttcaca aacaagtgtt tatcttccat cctaaggtat gttctt    56

<210> SEQ ID NO 113
<211> LENGTH: 56
<212> TYPE: DNA
<213> ORGANISM: Artificial sequence
<220> FEATURE:
<223> OTHER INFORMATION: Partial TOM1 Petunia hybrida Coding sequence
      (complementary strand)

<400> SEQUENCE: 113
ttaacagaaa cctaaagtgt tgttcacaa atagaaggta ggattccata caagaa    56

<210> SEQ ID NO 114
<211> LENGTH: 70
<212> TYPE: DNA
<213> ORGANISM: Artificial sequence
<220> FEATURE:
<223> OTHER INFORMATION: Partial TOM3 Petunia hybrida Coding sequence

<400> SEQUENCE: 114
tatttcgtcg ggatgttcag aagttgcatc ctgaggttag gcatcacaac tatcttgatg    60
tccggttgtc    70

<210> SEQ ID NO 115
<211> LENGTH: 70
<212> TYPE: DNA
<213> ORGANISM: Artificial sequence
<220> FEATURE:
<223> OTHER INFORMATION: Partial TOM3 Petunia hybrida Coding sequence
      (complementary strand)

<400> SEQUENCE: 115
ataaagcagc cctacaagtc ttcaacgtag gactccaatc cgtagtgttg atagaactac    60
aggccaacag    70

<210> SEQ ID NO 116
<211> LENGTH: 120
<212> TYPE: DNA
<213> ORGANISM: Artificial sequence

```
-continued

<220> FEATURE:
<223> OTHER INFORMATION: Fragment of the mGUS construct

<400> SEQUENCE: 116
accatttacg aacgatagag atctcgagct caagcttcga attctgcagt cgacggtacc      60
atgttcttcc cctcctgagg ggaagaatta cgtcctgtag aaaccccaac ccgtgaaatc     120
```